United States Patent [19]

Omura et al.

[11] Patent Number: 5,008,249

[45] Date of Patent: * Apr. 16, 1991

[54] THERAPEUTIC METHOD OF STIMULATING DIGESTIVE TRACT CONTRACTILE MOTION IN MAMMALS

[75] Inventors: Satoshi Omura, Tokyo; Zen Itoh, Maebashi, both of Japan

[73] Assignee: Kitasato Kenkyusho, Tokyo, Japan

[*] Notice: The portion of the term of this patent subsequent to Jun. 30, 2004 has been disclaimed.

[21] Appl. No.: 899,985

[22] Filed: Aug. 25, 1986

[30] Foreign Application Priority Data

Aug. 31, 1985 [JP] Japan ............................ 60-190958
Feb. 28, 1986 [JP] Japan ............................ 61-41413
May 31, 1986 [JP] Japan ............................ 61-124739

[51] Int. Cl.$^5$ ............................................. A61K 31/70
[52] U.S. Cl. ........................................ 514/29; 536/7.2; 536/7.3; 536/7.4
[58] Field of Search ........................... 536/7.2; 519/29

[56] References Cited

U.S. PATENT DOCUMENTS 3,884,904  5/1975  Jones et al. ........................ 536/7.2
4,677,097  6/1987  Omura et al. ...................... 514/29

FOREIGN PATENT DOCUMENTS 0969176  6/1975  Canada ............................... 536/7.2

OTHER PUBLICATIONS

Omura et al., J. Med. Chem., 1987, 30, 1941-1943.
Zen Itoh et al., Antimicrobial Agents and Chemotherapy, vol. 26, No. 6, pp. 863-869 (1984).
R. K. Clark, Jr. et al., Antibiotics and Chemotherapy, vol. 7, pp. 483-489 (1957).
V. C. Stephens et al., Antibiotics Annual, pp. 346-353 (1958-1959).

Edwin H. Flynn et al., Journal of the American Chemical Society, vol. 77, pp. 3104-3106 (1955).
P. Kurath et al., Experientia, vol. 27, p. 362 (1971).
P. H. Jones et al., Journal of Medicinal Chemistry, vol. 15, pp. 631-638 (1972).
J. Tadanier et al., Journal of Organic Chemistry, vol. 39, pp. 2495-2501 (1974).
S. Morimoto et al., The Journal of Antibiotics, vol. 37, pp. 187-189 (1984).

Primary Examiner—Johnnie R. Brown
Assistant Examiner—Elli Peselev
Attorney, Agent, or Firm—David G. Conlin; Ernest V. Linek

[57] ABSTRACT

Disclosed are digestive tract contractile motion stimulants containing compounds, or salts thereof, represented by the following general formula:

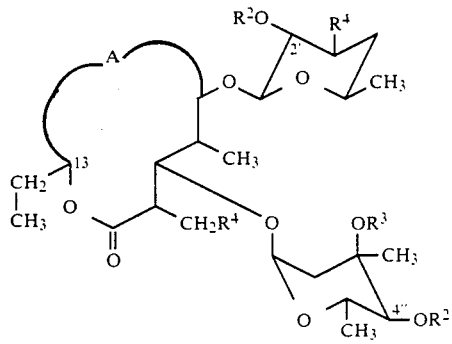

The compounds described above have an excellent effect of stimulating the gastrointestinal contractile motion, and the preparation of the present invention containing these compounds can be advantageously used as digestive tract contractile motion stimulants.

14 Claims, No Drawings

THERAPEUTIC METHOD OF STIMULATING DIGESTIVE TRACT CONTRACTILE MOTION IN MAMMALS

The present invention relates to a stimulant for contractile motion of the digestive tract of mammals.

PRIOR ART

The digestive tract consists of the stomach, the duodenum, the small intestine, etc., and plays an important role in the digestion of food taken from the mouth. The contructile motion of the digestive tract is essential in order to perform the digestion smoothly. In a healthy man, the autonomous nerve system and digestive tract hormones function effectively to induce contraction of the digestive tract not only immediately after the intake of foods but also in a state where the digestive tract is empty, when such contraction has been considered absent. The movement in such empty digestive tract is transmitted from the stomach to the duodenum and to the small intestine, and plays an important role for cleaning the digestive tract, thus preparing for next intake of foods (Z. Itoh, "Iden", 33, 29, 1979).

A stimulant for contraction of the digestive tract is expected to induce a normal movement of the digestive tract, in a human with weakened function of the digestive tract, thereby a healthy body being maintained.

Motilin is already known as a digestive tract hormone for stimulating the contraction of the digestive tract. This substance is a peptide, consisting of 22 amino acids and extracted by J. C. Brown in 1966 from the mucous membrane of a pig duodenum (J. C. Brown et al., Gastroenterology, 50, 333, 1966), and is already synthesized chemically (E. Wunsch et al., Zeitschrift fur Naturfoisch, 28C, 235, 1973).

PROBLEM TO BE RESOLVED BY THE PRESENT INVENTION

However the supply of motilin by extraction from natural substance or by chemical synthesis is not sufficient, and has not been possible in a large amount.

MEANS FOR SOLVING THE PROBLEM

In the course of a survey for providing a substance capable of stimulating the contraction of the digestive tract and adapted for a large supply, the present inventors have synthesized various derivatives from antibiotic erythromycin A, B, C, D and F and have found that said derivatives have a strong stimulating effect on the contraction of the digestive tract.

Based on this finding, the present inventors have made intensive efforts and have reached the present invention.

The present invention provides:

A digestive tract contractile motion stimulant containing a compound, or a salt thereof, represented by the general formula:

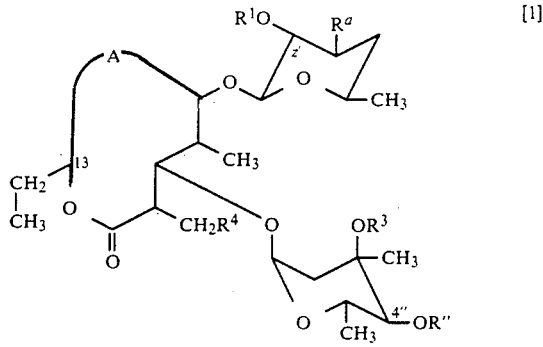

wherein $R^1$ stands for a hydrogen atom or an acyl radical which may be substituted; $R^2$ stands for a hydrogen atom, an acyl or alkyl radical which may be substituted; $R^3$ stands for a hydrogen atom or a methyl radical; $R^4$ stands for a hydrogen atom or a hydroxy radical; $R^a$ stands for the formula $$-N\begin{matrix}R^b\\R^c\end{matrix}$$

wherein $R^b$ stands for a hydrogen atom, a lower alkyl or cycloalkyl radical, $R^c$ stands for a hydrogen atom, a lower alkyl, cycloalkyl, lower alkenyl or lower alkynyl radical which may be substituted, or $R^b$ and $R^c$ form a cyclic alkylamino radical together with the adjacent nitrogen atom) or the formula $$N^+\begin{matrix}R^d\\-R^e\\R^f\end{matrix}X^-$$

(wherein $R^d$ stands for a lower alkyl radical, each of $R^e$ and $R^f$, which may be the same or different, stands for a lower alkyl, cycloalkyl, lower alkenyl or lower alkynyl radical which may be substituted, or $R^e$ and $R^d$ form a cyclic alkylamino radical together with the adjacent nitrogen atom, and $X^-$ stands for an anion); and when $R^a$ is the formula $$-N\begin{matrix}R^b\\R_c\end{matrix}, \quad A$$

stands for the formula:

$$\text{(structure with } R^{11}, R^{12}, CH_3, Z_{12}\text{)}$$

wherein, Z stands for the formula

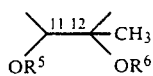

(wherein $R^5$ stands for a hydrogen atom, an acyl or alkyl radical which may be substituted, and $R^6$ stands for a hydrogen atom, an acyl radical of a lower carboxylic acid or an alkyl radical which may be substituted by an alkylthio radical), the formula

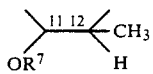

(wherein $R^7$ stands for a hydrogen atom, an acyl or alkyl radical which may be substituted),

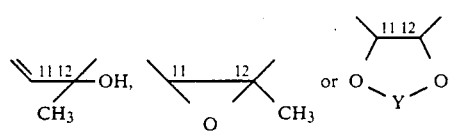

(wherein Y stands for the formula B—$R^8$ wherein $R^8$ stands for an alkyl or aryl radical,

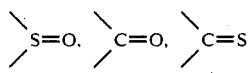

or the formula

wherein each of $R^9$ and $R^{10}$, which may be the same or different, stands for a hydrogen atom or an alkyl radical, or constitutes a cyclic alkyl radical with the adjacent carbon atom, or either of $R^9$ and $R^{10}$ is a hydrogen atom, an alkyl radical or an aryl radical while the other is a dialkylamino radical), $R^{11}$ and $R^{12}$ both stand for hydrogen atoms or both taken together form a chemical bond, or the formula:

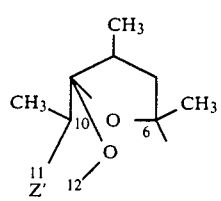

wherein Z' stands for the formula

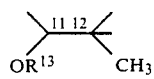

(wherein $R^{13}$ stands for a hydrogen atom, an acyl or alkyl radical which may be substituted), or when $R^a$ is the formula

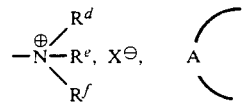

stands for the formula:

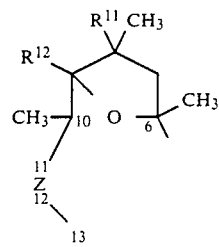

wherein $R^{11}$, $R^{12}$ and Z have the same meanings as defined above, the formula:

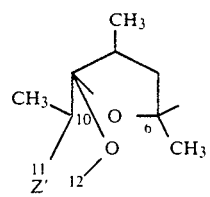

wherein Z' has the same meaning as defined above, or the formula:

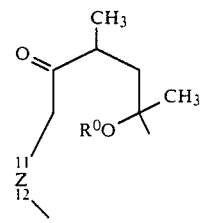

wherein Z has the same meaning as defined above, and $R^0$ stands for a hydrogen atom or low alkyl; with proviso that each of $R^1$, $R^2$, $R^4$, $R^5$, and $R^6$ is not a hydrogen atom at the same time, when $R^a$ is a dimethylamino radical, both of $R^{11}$ and $R^{12}$ taken together form a chemical bond and $R^3$ is a methyl radical; and each of $R^1$, $R^2$, $R^4$ and $R^{13}$ is not a hydrogen atom at the same time, when $R^a$ is a dimethylamino radical and $R^3$ is a methyl radical.

DESCRIPTION OF THE PREFERRED EMBODIMENTS

The acyl radical represented by $R^1$ in the foregoing formula can be a carboxylic acyl, a sulfonic acyl, a phosphorous acyl or a phosphoric acyl.

The acyl radical represented by $R^2$, $R^5$ or $R^7$ in the foregoing formula can be a carboxylic acyl or a sufonic acyl.

The carboxylic acyl is an acyl radical derived from a carboxylic acid, which can be a monocarboxylic or polycarboxylic acid, and a saturated or unsaturated carboxylic acid.

As the monocarboxylic acyl radical, a saturated or unsaturated acyl radical containing 1 to 20 carbon atoms (such as formyl, acetyl, propionyl, butyryl, isobutyryl, valeryl, isovaleryl, hexanoyl, pivaloyl, lauroyl, myristoyl, palmitoyl, stearoyl, acryloyl, propioloyl, methacryloyl etc.) or an aryl carboxylic acyl radical are preferred. The aryl carboxylic acid include benzene carboxylic acid, naphthalene carboxylic acid and the like.

As the polycarboxylic acyl radical, a dicarboxylic acyl radical, which can be a saturated or unsaturated acyl radical containing 2 to 6 carbon atoms, which may optionally be esterified, such as oxalo, carboxyacetyl, 3-carboxypropionyl, cis-3-carboxyacryloyl, trans-3-carboxyacryloyl, cis-3-methyl-3-carboxyacryloyl, etc, are preferred.

The sulfonic acyl is an acyl radical derived from a sulfonic acid, represented for example by the general formula $R^{14}SO_2-$ wherein $R^{14}$ stands for an alkyl, aryl or aralkyl radical. The alkyl radical preferably contains for example 1 to 6 carbon atoms, and may be linear or branched. Examples of the alkyl radicals are methyl, ethyl, propyl, isopropyl, butyl, isobutyl, sec-butyl, tert-butyl, n-pentyl and n-hexyl. Examples of the aryl radical include phenyl and naphthyl. The aryl radical may have a substituent and examples of said substituent include a lower alkyl radical (such as methyl), a lower alkoxy radical (such as methoxy), a halogen atom (such as fluorine, chlorine, and bromine), a nitro radical, a carboxy radical, etc.

An example of said aralkyl is 2-phenethyl.

The phosphrous acyl is an acyl radical derived from phosphorous acid, represented, for example, by the general formula

wherein $R^{15}$ stands for a hydrogen atom, an alkyl, aryl or aralkyl radical. The alkyl radical preferably contains for example, 1 to 6 carbon atoms and can be linear or branched. Examples of the alkyl radicals include methyl, ethyl, propyl, isopropyl, butyl, isobutyl, sec-butyl, tert-butyl, n-pentyl and n-hexyl. Examples of the aryl radical include phenyl, tolyl and naphthyl.

The aralkyl radical can be an aryl alkyl radical, wherein the aryl can be the above-mentioned aryl, while the alkyl preferably contains 1 to 3 carbon atoms, and there can be mentioned, for example, methyl, ethyl or propyl.

The phosphoric acyl is an acyl radical derived from phosphoric acid, represented, for example, by a general formula $(R^{16}O)_2PO-$ wherein $R^{16}$ has the same meaning as $R^{15}$. The substituent in the acyl radical which may be substituted, represented by $R^1$, $R^2$, $R^5$ and $R^7$, can be, for example, a halogen atom, an alkoxy or alkylthio radical.

Examples of the halogen atoms are chlorine, bromine, fluorine and iodine.

As the alkoxy radical, there can be mentioned radicals containing 1 to 4 carbon atoms, such as methoxy, ethoxy, propoxy and butoxy.

As the alkylthio radical, there can be metioned radicals containing, 1 to 4 carbon atoms, such as, methylthio, ethylthio, propylthio, isopropylthio, butylthio, isobutylthio, sec-butylthio and tert-butylthio.

The lower carboxylic acyl radical represented by $R^6$ in the foregoing formula can be a monocarboxylic acyl or polycarboxylic acyl radical containing 1 to 6 carbon atoms, such as, formyl, acetyl, propionyl, butyryl, isobutyryl, valeryl, isovaleryl, hexanoyl, oxalo, carboxyacetyl or 3-carboxypropionyl.

In the foregoing formula, the alkyl radical in the alkyl radical which may be substituted, represented by $R^0$, $R^2$, $R^5$ or $R^7$, preferably contains 1 to 3 carbon atoms, and can be linear or branched. Examples of the alkyl radicals include methyl, ethyl, propyl and isopropyl. The substituent is preferably an alkoxy radical containing 1 to 3 carbon atoms or an alkoxyalkoxy radical containing 2 to 6 carbon atoms, and examples of the alkoxy radicals include methoxy, ethoxy and propoxy, while examples of the alkoxyalkoxy radicals include methoxyethoxy, methoxypropoxy, methoxybutoxy, methoxypentyloxy, ethoxyethoxy, ethoxypropoxy, ethoxybutoxy and propoxypropoxy.

In the foregoing formula, the alkyl radical which is represented by $R^6$ and may have an alkylthio substituent can be methyl. The alkylthio as the substituent may include a radical represented by the general formula

wherein $R^{17}$ is a lower alkyl radical. The lower alkyl radical preferably contains 1 to 3 carbon atoms, such as methyl, ethyl or propyl.

In the foregoing formula, the alkyl radical represented by $R^8$ may contain 1 to 6 carbon atoms, preferably 1 to 3 carbon atoms, and examples thereof include methyl, ethyl and propyl.

In the foregoing formula, the aryl radical represented by $R^8$ is, for example, phenyl, tolyl or naphthyl.

In the foregoing formula, the alkyl radical containing 1 to 6 carbon atoms, represented by $R^9$ and $R^{10}$, can be linear or branched, and examples thereof include methyl, ethyl, propyl, isopropyl, butyl, isobutyl, sec-butyl, tert-butyl, n-pentyl and n-hexyl. Among these preferred is a linear or branched radical containing 1 to 3 carbon atoms, such as methyl, ethyl, propyl or isopropyl.

In the foregoing formula, the carbon chain represented by $R^9$ and $R^{10}$ for forming a cyclic alkyl together with the carbon atom in the acetal bond may have 4 to 5 carbon atoms, including tetramethylene, pentamethylene, etc.

In the foregoing formula, the aryl radical represented by $R^9$ and $R^{10}$ is, for example, phenyl, tolyl or naphthyl.

In the foregoing formula, the dialkylamino radical represented by $R^9$ and $R^{10}$ is represented by the general formula $-N(R^{18})_2$, wherein $R^{18}$ stands for a lower alkyl radical The lower alkyl radical may contain 1 to 3 carbon atoms, such as methyl, ethyl or propyl.

In the foregoing formula, the lower alkyl radical represented by $R^b$ or $R^d$ contains preferably 1 to 6 carbon atoms and examples thereof include methyl, ethyl, propyl, isopropyl, butyl, isobutyl, sec-butyl, pentyl, isopentyl and hexyl.

As to $R^a$ in the foregoing formula, the lower alkyl radical represented by $R^e$ or $R^f$ which may have substituents contains preferably 1 to 6 carbon atoms, and examples thereof include methyl, ethyl, propyl, isopropyl, butyl, isobutyl, pentyl and hexyl.

In the foregoing formula, substituted or unsubstituted cycloalkyl represented by $R^b$, $R^e$ or $R^f$ may contain 3 to 7 carbon atoms, and examples thereof include cyclopropyl, cyclobutyl, cyclopentyl, cyclohexyl, cycloheptyl, preferably those having 4 to 6 carbon atoms, namely cyclobutyl, cyclopentyl and cyclohexyl.

The lower alkenyl radical which may be substituted, represented by $R^e$ or $R^f$, contains preferably 2 to 6 carbon atoms, and examples thereof include vinyl, allyl, 2-butenyl, methylallyl, 3-butenyl, 2-pentenyl, 4-pentenyl, and 5-hexenyl.

The lower alkynyl radical which may be substituted, represented by $R^e$ or $R^f$, contains preferebly 2 to 6 carbon atoms, and examples thereof include ethynyl, propargyl, 2-butyn-1-yl, 3-butyn-1-yl, 3-butyn-2-yl, 1-pentyn-3-yl, 3-pentyn-1-yl, 4-pentyn-2-yl, and 3-hexyn-1-yl.

The substituents in the foregoing alkyl, cycloalkyl, alkenyl and alkynyl radicals, each of which may be substituted, include, for example, hydroxy, $C_{3-6}$cycloalkyl, $C_{6-10}$aryl, $C_{1-4}$alkoxy, $C_{1-4}$alkoxy-$C_{2-3}$-alkyl, $C_{3-6}$cycloalkyloxy, $C_{6-10}$aryloxy, $C_{7-12}$aralkyloxy, $C_{1-4}$alkylthio, $C_{3-6}$cycloalkylthio, $C_{6-10}$arylthio, $C_{7-12}$aralkylthio, amino, mono$C_{1-4}$alkylamino, di$C_{1-4}$alkylamino, $C_{3-6}$cycloalkylamino, $C_{6-10}$arylamino, $C_{7-12}$aralkylamino, azido, nitro, halogen, cyano, carboxy, $C_{1-4}$alkoxycarbonyl, $C_{6-10}$aryloxycarbonyl, $C_{3-6}$cycloalkyloxycarbonyl, $C_{7-12}$aralkyloxycarbonyl (CO in these carbonyl groups may be acetalyzed) $C_{1-5}$alkanoyl, formyloxy, $C_{1-4}$alkylsulfinyl, $C_{6-10}$arylsulfinyl, $C_{1-4}$alkylsulfonyl, $C_{6-10}$arylsulfonyl, $C_{1-15}$alkanoyloxy, sulfo, carbamoyl, carbamoyl which may be substituted, carbamoyloxy, carbamoyloxy which may be substituted, formylamino, $C_{1-4}$alkanoylamino, $C_{6-10}$arylcarbonylamino, $C_{1-4}$alkoxycarbonylamino, $C_{7-12}$aralkyloxycarbonylamino, oxo, epoxy, thioxo, sulfonamido, heterocyclic radical, heterocyclic thio, heterocyclic carbonylamino, heterocyclic oxy, heterocyclic amino, $C_{1-4}$alkoxycarboxycarbonyloxy, $C_{1-4}$alkylsulfonyloxy, $C_{6-10}$arylsulfonyloxy, sulfoamino, sulfamoylamino, ureido, and silyloxy.

The alkyl having cycloalkyl, aryl, $C_{1-4}$alkyl and the alkyl having a group containing heterocyclic radical, which may substitute to alkyl, alkenyl, alkynyl or cycloalkyl mentioned above, may have further substituents. Examples of such substituents are hydroxy, $C_{1-4}$alkyl (which may have substituents, and the substituent in this case is the same as the substituents in the alkyl as described above; the radical containing $C_{1-4}$alkyl as hereinafter mentioned may also have the same substituent), $C_{1-4}$alkoxy, $C_{1-4}$alkylthio, amino, $C_{1-4}$alkylamino, di$C_{1-4}$alkylamino, $C_{6-10}$arylamino, azido, nitro, halogen, oxo, cyano, carboxy, $C_{1-4}$alkoxycarbonyl, $C_{6-10}$aryloxycarbonyl, $C_{1-5}$alkanoyl, $C_{1-5}$alkanoyloxy, sulfo, carbamoyl, substituted carbamoyl, carbamoyloxy, $C_{1-4}$alkanoylamino, $C_{1-4}$alkoxycarbonylamino and sulfonamido.

Examples of the substituent in the foregoing aryl and heterocyclic radicals which may substituted include hydroxy, $C_{1-4}$alkyl, $C_{6-10}$aryl, $C_{3-6}$cycloalkyl, halogen, carboxy, sulfo, $C_{1-4}$alkoxy, $C_{1-4}$alkylthio, nitro, $C_{1-4}$alkoxycarbonyl, amino, mono$C_{1-4}$alkylamino, di$C_{1-4}$alkylamino, $C_{1-4}$alkanoylamino, $C_{6-10}$aryloxy, $C_{7-12}$aralkyl, $C_{7-12}$aralkyloxy, $C_{6-10}$arylamino, $C_{7-12}$aralkylamino, cyano, $C_{6-12}$aryloxycarbonyl, $C_{7-12}$aralkyloxycarbonyl, $C_{1-5}$alkanoyl, $C_{1-5}$alkanoyloxy, carbamoyl, carbamoyl which may be substituted, carbamoyloxy, which may be substituted, $C_{1-4}$alkoxycarbonyl- amino and oxo.

The alkyl, the radical containing $C_{1-4}$alkyl or the aryl group which is the substituent in the foregoing aryl and heterocyclic radical which may be substituted may further have substituents, and as the substituents the same substituents as the alkyl and aryl radicals as described above may be included.

The number of the substituents on the foregoing respective radicals is preferably 1 to 3.

These substituents will be described in detail below.

Examples of $C_{1-4}$alkyl radical as the substituent include methyl, ethyl, propyl, isopropyl, butyl, isobutyl, sec-butyl and tert-butyl Examples of $C_{3-6}$cycloalkyl radicals include cyclopropyl, cyclobutyl, cyclopentyl and cyclohexyl Examples of $C_{6-10}$aryl radicals include phenyl and naphtyl.

Examples of $C_{1-4}$alkoxy radical include methoxy, ethoxy, propoxy, isopropoxy, butoxy and tert-butoxy.

Examples of $C_{3-6}$cycloalkyloxy radicals include cyclopropyloxy, cyclopentyloxy and cyclohexyloxy Examples of $C_{6-10}$aryloxy redicals include phenoxy and naphtyloxy.

Examples of $C_{7-12}$aralkyloxy redical include benzyloxy, 2-phenethyloxy and 1-phenethyloxy Examples of $C_{1-4}$alkylthio radicals include methylthio, ethylthio, propylthio and butylthio.

Examples of $C_{3-6}$cycloalkylthio radicals include cyclopropylthio, cyclopentylthio and cyclohexylthio.

Examples of $C_{6-10}$arylthio radical include phenylthio and naphtylthio.

Examples of $C_{7-12}$aralkylthio radicals include benzylthio, 2-phenethylthio and 1-phenethylthio.

Examples of mono$C_{1-4}$alkylamono radicals include methylamino, ethylamino, propylamino, isopropylamino, butylamino, isobutylamino and tert-butylamino.

Examples of di$C_{1-4}$alkylamino radicals include dimethylamino, diethylamino, dipropylamino, dibutylamino, N-methyl-N-ethylamino, N-methyl-n-propylamino and N-methyl-N-butylamino.

Examples of $C_{3-6}$cycloalkylamino radicals include cyclopropylamino, cyclobutylamino, cyclopentylamino and cyclohexylamino.

Examples of $C_{6-10}$arylamino radicals include anilino and the like.

Examples of $C_{7-12}$aralkylamino radicals include benzylamino, 2-phenethylamino and 1-phenethylamino.

Examples of halogen atoms include fluorine, chlorine, bromine and iodine.

Examples of $C_{1-4}$alkoxycarbonyl radicals include methoxycarbonyl, ethoxycarbonyl, propoxycarbonyl, isopropoxycarbonyl, butoxycarbonyl, tert-butoxycarbonyl and isobutoxycarbonyl.

Example of $C_{6-10}$aryloxycarbonyl radicals include phenoxycarbonyl and the like.

Examples of $C_{3-6}$cycloalkyloxycarbonyl radicals include cyclopropyloxycarbonyl, cyclobutyloxycarbonyl, cyclopentyloxycarbonyl and cyclohexyloxycarbonyl.

Examples of $C_{7-12}$aralkyloxycarbonyl radicals include benzyloxycarbonyl, 1-phenetyloxycarbonyl and 2-phenetyloxycarbonyl.

Examples of $C_{1-5}$alkanoyl radicals include formyl, acetyl, propionyl, butyryl and pivaloyl.

Examples of $C_{1-15}$alkanoyloxy radicals include formyloxy, acetoxy, butyryloxy, pivaloyloxy, pentanoyloxy, hexanoyloxy, heptanoyloxy, octanoyloxy, nonanoyloxy, decanoyloxy, undecanoyloxy, dodecanoyloxy, tridecanoyloxy, tetradecanoyloxy and pentadecanoyloxy.

Examples of substituted carbamoyl radicals include N-methylcarbamoyl, N, N-dimethylcarbamoyl, N- ethylcarbamoyl, N,N-diethylcarbamoyl, N-phenylcarbamoyl, pyrrolidinocarbonyl, piperidinocarbonyl, piperazinocarbonyl, morpholinocarbonyl and N-benzylcarbamoyl.

Examples of substituted carbamoyloxy radicals include N-methylcarbamoyloxy, N,N-dimethylcarbamoyloxy, N-ethylcarbamoyloxy, N-benzylcarbamoyloxy, N,N-dibenzylcarbamoyloxy, N-benzylcarbamoyloxy, N,N-dibenzylcarbamoyloxy and N-phenylcarbamoyloxy.

Examples of $C_{1-4}$alkanoylamino radicals include formylamino, acetamido, propionamido and butyrylamino.

Example of $C_{6-10}$arylcarbonylamino radicals include benzamido and the like.

Examples of $C_1$ alkoxycarbonylamino radicals include methoxycarbonylamino, ethoxycarbonylamino, butoxycarbonylamino and tert-butoxycarbonylamino.

Examples of $C_{7-12}$ aralkyloxycarbonylamino radical include benzyloxycarbonylamino, 4-methoxybenzyloxycarbonylamino, 4-nitrobenzyloxycarbonylamino and 4-chlorobenzyloxycarbonylamino.

Examples of sulfonamido radicals include methanesulfonylamino, ethanesulfonylamino, butanesulfonylamino, benzenesulfonylamino, toluenesulfonylamino, naphtalenesulfonylamino, trifuluoromethanesulfonylamino, 2-chloroethanesulfonylamino and 2,2,2-trifuluoromethanesulfonylamino.

Heterocyclic radicals include cyclic groups containing 1 to 5 nitrogen atoms, oxygen atoms, sulfur atoms and examples thereof are pyrrolidinyl, pyrrolyl, pyrazolyl, imidazolyl, furyl, thienyl, oxazolyl, isooxazolyl, isothiazolyl, thiazolyl, piperidinyl, pyridyl, pyridazinyl, pyrazinyl, piperadinyl, pyrimidinyl, pyranyl, tetrahydropyranyl, tetrahydrofuryl, indolyl, quinolyl, 1,3,4-oxadiazolyl, thieno[2,3-d]pyridyl, 1,2,3-thiadiazolyl, 1,3,4-thiadiazolyl, 1,2,3-triazolyl, 1,2,4-triazolyl, 1,3,4-triazolyl, tetrazolyl, 1,3-dioxoranyl, tetrazolo[1,5b-]pyridazinyl, benzothiazolyl, benzooxazolyl, benzoimidazoryl, benzothienyl and morpholinyl.

As a heterocyclic thio, heterocyclic oxy, heterocyclic amino and heterocyclic carbonylamino radicals, there can be mentioned radicals having the above heterocyclic radicals bonded to sulfur atom, oxygen atom, nitrogen atom or carbonylamino radical, respectively.

Examples of $C_{1-4}$alkylsulfonyloxy radicals include methanesulfonyloxy, ethanesulfonyloxy and butanesulfonyloxy.

Examples of $C_{6-10}$arylsulfonyloxy radicals include benzenesulfonyloxy and toluenesulfonyloxy.

Examples of silyloxy radicals include trimethylsilyloxy, t-butyldimethylsilyloxy and t-butyldiphenylsilyloxy.

Examples of $C_{1-4}$alkylsulphynyl radicals include methylsulfinyl, ethylsulfinyl, propylsulfinyl and butylsulfinyl.

Examples of $C_{6-10}$arylsulfinyl radicals include phenylsulfinyl and naphtylsulfinyl.

Examples of $C_{1-4}$alkylsulfonyl radicals include methanesulfonyl, ethanesulfonyl and butanesulfonyl.

Examples of $C_{6-10}$arylsulfonyl radicals include benzenesulfonyl and toluenesulfonyl.

Examples of $C_{1-4}$alkoxycarbonyloxy radicals include methoxycarbonyloxy, ethoxycarbonyloxy and tert-butoxycarbonyloxy.

Further specific examples of the foregoing respective radicals include chloromethyl, bromomethyl, iodomethyl, trifluoromethyl, chloroethyl, bromoethyl, iodoethyl, chloropropyl, hydoroxymethyl, hydroxyethyl, hydroxypropyl, 2-hydroxy-2-phenylethyl, cyclopropylmethyl, cyclobutylmethyl, cyclopentylmethyl, cyclohexylmethyl, 2-cyclohexylethyl, 3-chlorocyclobutylmethyl, benzyl, 4-chlorobenzyl, 4-nitrobenzyl, 4-methoxybenzyl, 2,4-dimethoxybenzyl, 3,4-dimethoxybenzyl, 4-methylbenzyl, 2-ethoxyethyl, 2-(2,2,2-trifuluoroethoxy)ethyl, methoxymethyl, 2,2-dimethoxyethyl, 2,2-diethoxyethyl, cyclopropylmethoxymethyl, cyclobutylmethoxymethyl, 2-cyclopropylmethoxyethyl, 2-cyclobutylmethoxyethyl, 2-benzyloxyethyl, 3-benzyloxypropyl, 2-phenoxyethyl, 2-(2-phenethoxy)ethyl, 3-phenylpropyl, methylthiomethyl, 2-methylthioethyl, 2-phenylthioethyl, 2-benzylthioethyl, 2-butylthioethyl, cyclohexylthiomethyl, 2-(4-pyridylthio)ethyl, aminomethyl, aminoethyl, 2-methylaminoethyl, 2-tert-butylaminoethyl, 2-dimethylaminoethyl, 3-dimethylaminopropyl, 2-cyclohexylaminoethyl, 2-benzylaminoethyl, 2-azidoethyl, nitromethyl, 2-nitroethyl, cyanomethyl, 2-cyanoethyl, 4-cyanobutyl, carboxymethyl, 2-carboxyethyl, ethoxycarbonylmethyl, phenoxycarbonylmethyl, cyclopentyloxycarbonylmethyl, acetylmethyl, benzoylmethyl, 4-chlorobenzoylmethyl, 3-(4-bromobenzoyl)propyl, 3-methoxybenzoylmethyl, 2-formyloxyethyl, 2-methylsulfinylethyl, 2-phenylsulfinylethyl, 2-methylsulfonylethyl, 3-phenylsulfonylpropyl, 2-acetoxyethyl, 4-acetoxybutyl, pivaloyloxymethyl, 3-sulfopropyl, carbamoylmethyl, 3-carbamoylpropyl, pyrrolidinocarbonylmethyl, 2-(N-ethyl-benzylamino)ethyl, 2-(2-oxopyrrolidino)ethyl, 2-formylaminoethyl, 3-formylaminopropyl, 3-trifluoroacetamidopropyl, 2-benzamidoethyl, 3-tert-butoxycarbonylaminopropyl, benzyloxycarbonylaminopropyl, 2,3-epoxypropyl, 2-thioacetamidoethyl, 3-sulfoaminopropyl, 2-(1,3-dioxoran-2-yl)ethyl, 2-,3-, 4-pyridylmethyl, 2-(4-pyridyl)ethyl, 3-(4-pyridyl)propyl, furfulyl, 3-(2-furyl)allyl, 3-(2-furyl)propyl, 2-(2pyranyloxy)ethyl, 2-(3-indolyl)ethyl, 3-(1-indolyl)propyl, 3-(2-benzimidazolyl)propyl, 2-morpholinoethyl, (3-isoxazolyl)methyl, 2-(2-pyridylthio)ethyl, 2-(2-benzthiazolyl)ethyl, 2-(2-pyrimidinylthio)ethyl, 2-(2-aminoethylthio)ethyl, 2-isonicotinoylaminoethyl, 2-thenoylaminoethyl, 2-furoylaminoethyl, 2-(tert-butoxycarbonyloxy)ethyl, 3-(tert-butoxycarbonyloxy)propyl, 2-methylsulfonyloxyethyl, 2-(p-toluenesulfonyloxy)ethyl, 2-(tert-butyldimethylsilyloxy)ethyl, sulfoaminomethyl, 2-(sulfoaminoethyl, ureidomethyl, 2-ureidoethyl, sulfamoylaminomethyl, 2-sulfamoylaminoethyl and (2-methoxyethoxy)methyl.

Examples of more preferable substituents in the lower alkyl, cycloalkyl, lower alkenyl and lower alkynyl radicals which may be substituted include halogen atoms (such as chlorine, bromine, iodine and fluorine), lower alkoxy groups having 1 to 4 carbon atoms (such as methoxy, ethoxy, propoxy, isprooxy, and butoxy), lower alkylthio radicals having 1 to 4 carbon atoms (such as methylthio, ethylthio, propylthio, and butylthio), aryl radicals (such as phenyl, tolyl, naphthyl, etc.), hydroxyl radical, alkoxycarbonyloxy radicals (such as tert-butoxycarbonyloxy), aralkyloxycarbonyloxy radicals (such as benzyloxycarbonyloxy), amino, substituted amino radicals (such as dimethylamino, and diethylamino), heterocyclic radicals (cyclic amino) (such as morpholino, piperidino, pyrrolidino, and 2-oxypyrrolidino), acyloxy radicals having 1 to 3 carbon atoms (such as formyloxy acetoxy and trifluoroacetoxy), acylamino radicals having 1 to 3 carbon atoms (such as acetamido, and trifluofroacetamido), carboxy, lower ($C_{1-4}$) alkoxycarbonyl radicals (such as methoxycarbonyl, ethoxycarbonyl, and butoxycarbonyl), carbamoyl, substituted carbamoyl radicals (such as dimethylcarbamoyl and diethylcarbamoyl), sulfo and others.

In the foregoing formula, as the carbon chain represengted by $R^b$ and $R^c$ or $R^d$ and $R^e$ for forming a nitrogen containing cyclic alkylamino together with the nitrogen atom on the 3'-position, those have 3 to 6 carbon atoms such as trimethylene, tetramethylene, pentamethylene and hexamethylene are included.

In the foregoing formula, examples of the anions represented by $X^-$ include halogen ions (such as iodide ion, bromo ion and chloro ion), sulfate ion, phosphate ion, nitrate ion, methanesulfate ion, p-tolylsulfate ion, benzenesulfate ion, hydroxyl ion and organic carboxylae ion (such as oxalate ion, maleate ion, fumarate ion, succinate ion, citrate ion, lactate ion, trifluoroacetate ion, lactobionate ion, acetate ion, propinate ion and ethylsuccinate ion).

In the compound (1) of the present invention, it is preferable that $R^0$ is a hydrogen atom; $R^1$ is a hydrogen atom or an alkyl carboxylic acyl radical having 1 to 5 carbon atoms; $R^2$ is a hydrogen atom, an alkyl carboxylic acyl radical having 1 to 5 carbon atoms, an alkyl sulfonic acyl radical having 1 to 5 carbon atoms; or an alkylthiomehyl radical having 1 to 5 carbon atoms; $R^3$ is a methyl radical; $R^4$ is a hydrogen atom; Z is the formula

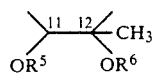

wherein each of $R^5$ and $R^6$ is a hydrogen atom, an alkyl carboxylic acyl radical having 1 to 5 carbon atoms or an alkyl sulfonic acyl radical having 1 to 5 carbon atoms, or $R^5$ and $R^6$ from

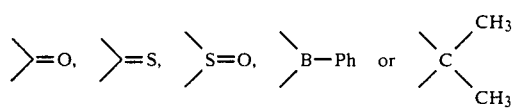

as Y; each of $R^d$ and $R^e$ is an alkyl radical having 1 to 3 carbon atoms, or $R^d$ and $R^e$ form a cyclic alkyl radical; $R^f$ is an unsubstituted or substituted alkyl radical having 1 to 5 carbon atoms, a alkenyl or alkynyl radical having 2 to 6 carbon atoms.

It is further preferable that at least one of $R^5$ and $R^6$ is an alkyl carboxylic acyl or alkylthiomethyl radical, each of which has 1 to 5 carbon atoms, or Y is

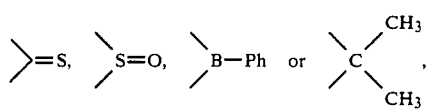

when $R^d$ and $R^e$ are alkyl radicals having 1 to 3 carbon atoms and form a tertiary amino radical as $R^a$, and each of $R^1$ and $R^2$ is an hydrogen atom or an alkyl carboxylic acyl having 1 to 5 carbon atoms. Furthermore, at least one of $R^5$ and $R^6$ is preferably an alkyl carboxylic acyl radical having 1 to 5 carbon atoms, an alkylthiomethyl radical having 1 to 5 carbon atoms or an alkyl sulfonic acyl radical having 1 to 5 carbon atoms, or Y is preferably

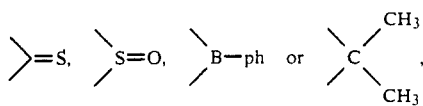

when $R^1$ is a carboxylic acyl radical having 1 to 5 carbon atoms and $R^2$ is a hydrogen atom.

When $R^a$ is a quaternary ammonium salt, it is preferable that both $R^5$ and $R^6$ are hydrogen, or at least one of $R^5$ and $R^6$ is an alkyl acyl radical having 1 to 5 carbon atoms or an alkyl sulfonic acyl radical.

In the compound (1) of the present invention, $R^a$ is preferable to be a quaternary ammonium salt. Particularly, it is preferable that $R^d$ and $R^e$ form together with adjacent nitrogen atom a cyclic alkylamino radical of 5 to 7 members such as pyrrolidine, piperidine, hexamethyleneimine and the like, or both $R^d$ and $R^e$ are alkyl radicals having 1 to 5 carbon atoms and $R^f$ is an alkyl radical having 1 to 5 carbon atoms, an alkenyl or alkynyl radical having 2 to 6 carbon atoms. When they have a substituent, it is particularly preferable to be hydroxy, carboxy, $C_{1-4}$ alkoxycarbonyl, halogen, cyano, $C_{3-5}$cycloalkyl and so on. As X of the quaternary ammonium salt, there are preferably mentioned chlorine, bromine and iodine.

The compound (1) of the present invention can be prepared according to the following method.

A compound which may be protected, represented by the following formula, is reacted with an acylating, alkylating, boronating, carbonating, sulfinylating or ketalizing agent, followed by the removal of protection, if necessary, whereby the compound [1] can be prepared:

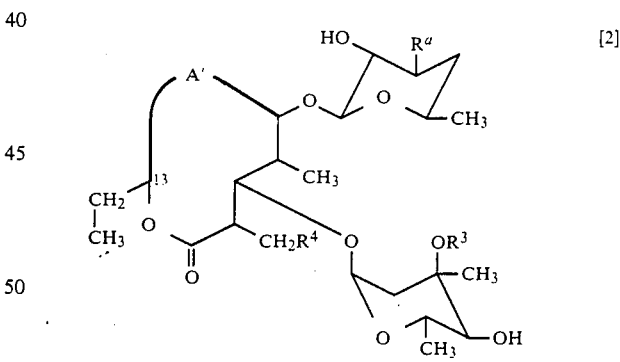

wherein $R^3$ and $R^a$ have the same meanings as defined above, A' represents the formula:

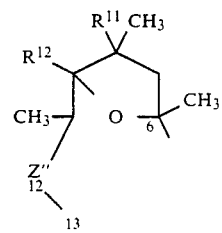

(wherein Z" represent the formula

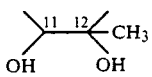

or the formula

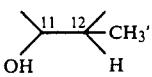

have the same meanings as defined above) or the formula:

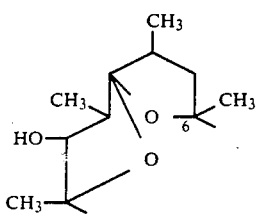

A compound represented by the following formula or its salt:

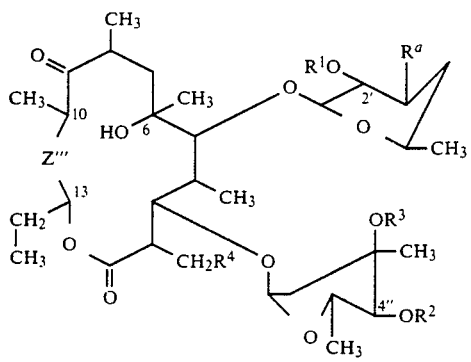

[3]

wherein $R^1$, $R^2$, $R^3$, $R^4$ and $R^a$ have the same meanings, $Z41'$ represents the formula

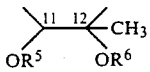

(wherein $R^5$ and $R^6$ have the same meanings as defined above), the formula

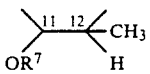

(wherein $R^7$ has the same meaning as defined above) or the formula

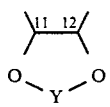

(wherein Y has the same meaning as defined above), is treated under a acydic condition, whereby a compound or its salt, represented by the following formula, can be prepared:

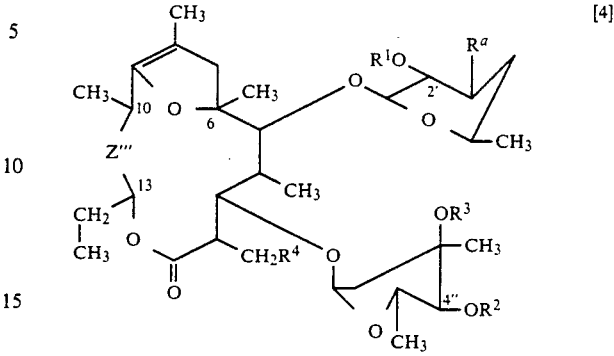

[4]

wherein $R^1$, $R^2$, $R^3$, $R^4$, $R^a$ and $Z'''$ have the same meanings as defined above.

The compound [1] can be prepared by subjecting a compound represented by the following formula to N-alkylation, N-alkenylation or N-alkynylation reaction:

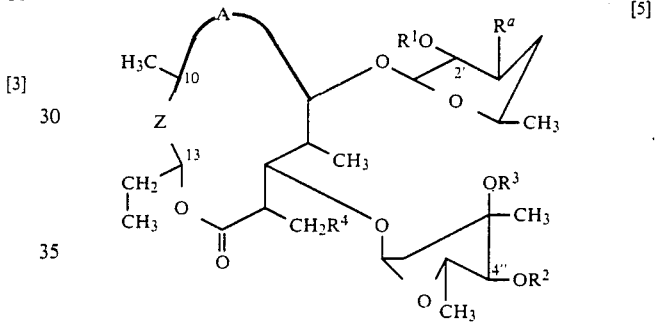

[5]

wherein A, $R^1$, $R^2$, $R^3$ and $R^4$ have the same meanings as defined above, $R^g$ represents $-NH-R^b$ (wherein $R^b$ has the same meaning as defined above) or the formula

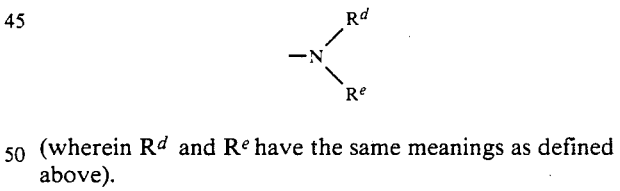

(wherein $R^d$ and $R^e$ have the same meanings as defined above).

The compound [1] can be prepared by subjecting the compound [2] to a already known reaction, namely by reacting with an acylating, alkylating, boronating, carbonating, sulfinylating or ketalyzing agent, followed by the removal of protection, if necessary.

The acylating agent employable in the acylation is a reactive derivative of a carboxylic acid capable of introducing a carboxylic acyl radical, such as an acid halide, an acid anhydride, an amide compound, an active ester or an active thioester. Examples of such reactive derivatives are as follows:

(1) Acid halide

Examples of such acid halides are acid chloride and acid bromide.

(2) Acid anhydride

Examples of such acid anhydrides include mixed anhydrides of monoalkyl carbonic acid, mixed anhydrides of aliphatic carboxylic acids such as acetic acid, pivalic acid, valeric acid, isovaleric acid, trichloroacetic acid etc., mixed anhydrides of aromatic carboxylic acids such as benzoic acid, and symmetric acid anhydrides.

(3) Amide compound

A examples of such amide compounds, there can be used compounds wherein an acyl radical is bonded to a nitrogen atom in a ring, such as a pyrazole, imidazole, 4-substituted imidazole, dimethylpyrazole or benzotriazole.

(4) Active ester

Examples of such active esters include methyl ester, ethyl ester, methoxymethyl ester, propargyl ester, 4-nitrophenyl ester, 2,4-dinitrophenyl ester, trichlorophenyl ester, pentachlorophenyl ester, mesylphenyl ester, and esters with 1-hydroxy-1H-2-pyridone, N-hydroxysuccinimide or N-hydroxyphthalimide.

(5) Active thioester

Examples of such active thioesters include thioesters with heterocyclic thiols such as 2-pyridylthiol or 2-benzothiazolylthiol.

The above-mentioned reactive derivatives are suitably selected according to the kind of the carboxylic acid.

In case a reactive derivative of a polycarboxylic acid is employed as the acylating agent, carboxyl radicals, except one, are preferably protected in the form of esters.

The acylating agent can also be a reactive derivative of a sulfonic acid capable of introducing a sulfonic acyl radical, for example an acid halide such as methane sulfonyl chloride, benzylsulfonyl chloride or paratoluene sulfonyl chloride, or a symmetric acid anhydride such as methane sulfonic anhydride or paratoluene sulfonic anhydride.

In the alkylation, the alkylating agent employable for the alkylation at the 4"- or 11- position can for example be a corresponding alkyl halide (for example chloride, bromide or iodide), and that employable for the alkylation at the 12- position can for example be dimethyl sulfoxide.

Example of the boronating agents employable in the boronation reaction are alkylboric acids (such as ethylboric acid) and arylboric acids (such as phenylboric acid).

Examples of the carbonating agents employable in the carbonation reaction are ethylene carbonate, carbonyl diimidazole and thiocarbonyl diimidazole.

Examples of the sulfinylating agents employable in the sulfinylation reaction is ethylene sulfite.

Examples of the ketalyzing agents employable in the ketalyzation reaction are 2-methoxypropene, 2,2-dimethoxypropane, 1,1-dimethoxycyclohexane, N,N-dimethylformamide dimethylacetal, and N,N-dimethylacetamide dimethylacetal.

In case of employing a reactive derivative of a carboxylic acid as the acylating agent in the acylation reaction, the amount of said acylating agent varies according to the number of acyl radicals to be introduced.

The solvent to be employed in the acylation is not limited as long as it does not react with the acylating agent, but is preferably dichloromethane, ether, pyridine, chloroform or the like. Examples of bases are tertiary amines such as triethylamine, diisopropylethylamine and tribenzylamine, and inorganic salts such as potassium carbonate. The reaction temperature is about 0° C. to 80° C., and the reaction time is about 10 minutes to 2 weeks.

In case of employing a reactive derivative of a sulfonic acid as the acylating agent in the acylation reaction, the amount of the acylating agent varies according to the number of acyl radicals to be introduced.

Examples of the solvents to be employed in the acylation are pyridine, chloroform, ether and dichloromethane. Examples of the bases are tertiary amines such as pyridine, tribenzylamine and diisopropylethylamine. The reaction temperature is about 0° C. to 50° C., and the reaction time is about 10 minutes to 2 days.

The amount of alkylating agent in the alkylation reaction varies according to the number of alkyl radicals to be introduced.

Examples of the solvents to be employed in the alkylation reaction are chloroform, dimethyl sulfoxide, dimethyl formamide, ether and ethanol. The reaction temperature is about 0° C. to 80° C., and the reaction time is about 15 minutes to 1 week. Examples of the base to be employed in the alkylation at the 4"- or 11- position are tertiary amines such as diisopropylethylamine or pyridine, sodium hydride and potassium hydride.

In the boronation reaction, the boronating agent is preferably employed in an equivalent amount or in excess (2 –3 times in molar ratio). Examples of the solvents to be employed in the boronation reaction are benzene, toluene and ether The reaction temperature is about 80° C. to 130° C., and the reaction time is about 1 hour to 5 hours.

In the carbonation reaction, the carbonating agent is preferably employed in a 2–10 times excess amount, in molar ratio, according to the kind thereof. Examples of the solvent to be employed in the carbonation reaction are benzene and toluene. The reaction temperature is about 25° C. to 130° C., and the reaction time is about 30 minutes to 1 days.

In case of employing ethylene carbonate as the carbonating agent in the carbonation reaction, the base to be employed can be an inorganic salt such as potassium carbonate.

In the sulfinylation reaction, the sulfinylating agent is preferably employed in a samll excess (2–3 times in molar ratio). Examples of the solvents to be employed in the sulfinylation are methanol and ethanol. The reaction temperature is about 20° C. to 30° C., and the reaction time is about 2 days to 3 days. The base to be employed in said sulfinylation can be an inorganic salt such as potassium carbonate.

The ketalization reaction should preferably be carried out according to the ketal exchange reaction by using the compound of the corresponding formula

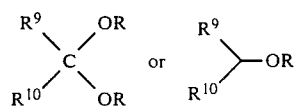

(wherein $R^9$ and $R^{10}$ have the same meanings as defined above, R represents a lower alkyl radical such as methyl, ethyl) as the ketalyzing agent. As the reaction solvent there can be employed halogenated hydrocarbons such as chloroform, ethers such as tetrahydrofuran, and amides such as dimethylformamide, and it is also possible to use the ketalyzing agent itself as the solvent. Although the ketalating agent may be used usually in slight excess (about 2 times mols) to a great excess (about 100 times mols), but the amount is preferably 2 to 4 times excess in the case of the latter ketalyzing agent. As the catalyst, a strong acid salt of pyridine (such as pyridinium chloride), etc., is preferably used. Particularly in the case of the present compound, the combination of the latter ketalyzing agent and pyridineum chloride is preferred. The reaction may be conducted preferably at a temperature of 0° C. to the boiling point of the solvent, more preferably at around room temperature (about 15° C. to 25° C.). The reaction time may be from several hours to 72 hours, usually about 12 to 24 hours.

In the above-mentioned reactions of the compound [2] which may be protected, the order of reactivity of hydroxyl radicals on the 2'-, 4"-, 11- and 12- positions is $2' > > 4'' \geq 11 > > 12$.

In the following there are explained the cases of introducing a carboxylic acyl radical. In case of acylation at the 2'- position only, a chloroform solution of the compound [2] is agitated with an acylating agent in a small excess (about 2 times in molar ratio) and a base in a small excess (about 3 times in molar ratio). The reaction is completed in a short time at room temperature, and the desired compound is obtained by purification by silica gel chromatography.

In case of acylation at the 4"- position only, a compound subjected to the acetylation at the 2'- position as explained above is agitated with an acylating agent and a base in large excess for 15 minutes to overnight at room temperature, then treated in the usual manner and purified by silica gel chromatography to obtain a 2'-0-acetyl-4'-0-acylated compound. The desired compound is obtained by allowing a methanolic solution of the above-mentioned compound to stand for 1 to 2 days at room temperature, and distilling off methanol under a reduced pressure, followed by purification by silica gel chromatography.

In case of acylation at the 11- position only, a 2'-0-acetyl-4"-formylated compound obtained in the above-explained manner is agitated with large excesses of an acylating agent and a base for several hours to several days at room temperature to about 70° C. to obtain a 2'-0-acetyl-4"-formyl-11- acylated compound, which is then heated under reflux for about 3 hours to 3 days in methanol to obtain the desired compound.

In case of acylation at the 12-position only, a 2'-0-acetylated compound obtained in the above-explained manner is agitated overnight with trimethylchlorosilane and tribenzylamine and treated in the usual manner to obtain a 2'-0-acetyl-11, 4"-di-0-silylated compound. A dichloroethane solution of the compound is agitated with large excesses of an acylating agent and a base for two days at 75 −80° C. to obtain a 2'-0-acetyl-11, 4"-di-0-silyl-12-0-acylated compound, which is treated in the usual manner and subjected to methanolysis to obtain the desired compound.

In the following, there will explained the case of introducing an alkyl radical. In case of alkylation at the 4"-position only, a compound of which the 2'-position is acetylated in the above-explained manner is dissolved in dichloromethane, added with an alkylating agent and a base under cooling with ice, and is let to stand for 30 minutes at room temperature to obtain a 2'-0-acetyl-4"-0-alkylated compound. This compound is dissolved in methanol, then is let to stand for one day at room temperature, and the reaction solution is concentrated under a reduced pressure and is purified by silica gel chromatography to obtain the desired compound.

In case of alkylation at the 11-position only, the compound [2] is reacted with excessive amounts of benzyloxycarbonyl chloride and sodium hydrogen carbonate, and the 3'-dimethylamino radical are protected by, in the latter case, by methyl radical of it by the acyl. It is then dissolved in dimethyl formamide and reacted with an alkylating agent and a base under cooling with ice. The product is then dissolved in water and ethanol, then subjected to hydrogenolysis in the presence of a palladium-carbon catalyst, and hydrogenated in the presence of formaldehyde to obtain the desired compound.

In case of alkylation at the 12-position only, a compound, of which the 2'-, 4"- and 11- position are acetylated in the above-explained manner, is dissolved in dimethyl sulfoxide and is let to stand, with a large excess of acetic anhydride, for 96 hours to 1 week at room temperature. The reaction solution is then concentrated under a reduced pressure, and purified by silica gel chromatography, and the obtained compound is dissolved in methanol and heated with lithium hydroxide at 50° C. for 4 hours to obtain the desired compound.

Preferred examples of the protecting radicals are acetyl for the 2'- position, formyl and silyl for the 4'-position, and acetyl and silyl for the 11- position.

A compound [2] having a protective radicals can be prepared in processes similar to that explained above.

If thus prepared compound [1] has a protective radicals, they may be removed if necessary. The removal of the protective radical can be suitably achieved in the usual manner, for example, by a method using a base (alkaline hydrolysis), a method using hydrazine or a reduction method, according to the kind of the protective radicals. In the method using a base, there can be employed, depending on the kind of the protective radicals and other conditions, for example, a hydroxide of an alkaline metal such as sodium, potassium or lithium or an alkali earth metal such as calcium or magnesium, an inorganic base such as a carbonate, a metal alkoxide, an organic amine, an organic base such as quaternary ammonium salt, or a basic ion exchange resin. If the method using a base is conducted in the presence of a solvent, said solvent is usually a hydrophilic organic solvent, water or a mixture thereof.

The reduction method is conducted, for example, in the presence of a reducing metal catalyst, depending on the kind of protective radicals and other conditions, and the examples of such catalyst employable in catalytic reduction include platinum catalysts such as platinum sponge, platinum asbestos, platinum black, platinum oxide and colloidal platinum: palladium catalysts such as palladium sponge, palladium black, palladium oxide, palladium on barium sulfate, palladium on barium carbonate, palladium on activated carbon, colloidal palladium and palladium on silica gel; reduced nickel, nickel oxide, Raney nickel and Urushibara nickel. The reduction method is usually conducted in a solvent, which is usually composed of an alcohol such as methanol, ethanol, propyl alcohol or isopropyl alcohol, or ethyl acetate.

The method using a base or the reduction method is usually conducted under cooling or under heating.

In the reaction in which the compound [3] is treated under acidic conditions to prepare the compound [4], there can be employed, for acidification, an organic acid such as acetic acid, pyridinium chloride or pyridinium paratoluene sulfonate.

The reaction temperature is about 0° C. to 30° C., the reaction time is about 30 minutes to 1 hour, and the range of pH in reaction is 1 to 6. The solvent employable in the reaction is, for example, acetic acid, chloroform, dichloromethane or ether, and the reaction is preferably conducted under agitation.

By subjecting a compound [5'] which corresponds to the compound [5] in which $R^9$ is a formula $-NH-R^b$ (wherein $R^b$ is the same meaning as defined above) to N-alkylation, N-alkenylation or N-alkynylation, a compound [1'] which corresponds to the compound [1] in which $R^a$ is the formula

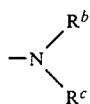

(wherein $R^b$ and $R^c$ have the same meanings as defined above) can be prepared.

The reaction is carried out by reacting a corresponding ketone or aldehyde to the compound [5'] under the reduction conditions. As the reduction conditions, catalytic reduction can be used [see R. K. Clark Jr. and M. Flyfelder, ANTIBIOTICS AND CHEMOTHERAPY, 7, 483 (1957)]. The catalyst usable therefor may be those as described in the previous item of reductive deprotection, particularly preferable being palladium black, palladium carbon, and Raney nickel. The reaction can be preferably carried out in alcohols (such as methanol and ethanol), ethers (such as tetrahydrofuran and dimethoxyethane) and aqueous mixtures thereof, in the presence of hydrogen gas, under ice cooling to about 80°, preferably around room temperature.

As the reduction condition, reduction by use of a metal hydride may also be used. As the metal hydride sodium borohydride, sodium cyanoborohydride are preferred.

The reaction is carried out preferably in a solvent such as alcohols (e.g. methanol and ethanol), ethers (e.g. tetrahydrofuran and dimethoxyethane), nitriles (e.g. acetonitrile) and aqueous mixtures thereof, more preferably while maintaining the pH of the reaction mixture at neutral to weakly acidic (pH about 3 to 6), and it is preferable for control of the pH, to add a buffer solution or mineral acid (such as hydrochloric acid), an organic acid (such as acetic acid) or an aqueous solution thereof.

The amount of the metal hydride used is varied, depending on the carbonyl compound used, but it is a slight excess over to about 100 times the theoretical amount, preferably a slight excess to about 10 times thereof, and it is added suitably with the progress of the reaction.

The reaction is carried out at about −20° C. to 80° C., preferably at about 0° C. to 30° C..

The compound [1'] can also be synthesized by allowing the compound [5'] to react with, for example, corresponding alkyl, alkenyl or alkynyl halide, an ester, trioxonium salt, etc., in the presence of a base.

Examples of the bases include sodium hydroxide, potassium hydroxide, sodium hydrogen carbonate, potassium carbonate, butyl lithium phenyl lithium and sodium hydride.

Examples of the halogen atoms in the halide include chlorine, bromine and iodine, particularly preferably iodine.

Examples of the esters include a sulfate ester and the like.

Typical examples of the trioxonium salts include trimethyloxonium fluoroborate, triethyloxonium fluoroborate, etc.

The reaction reagents are each about 1 to 100 mol equivalent, preferably about 2 to 25 mol equivalent per 1 mol of the starting compound.

Examples of the solvents to be used in the reaction include preferably halogenated hydrocarbons (such as chloroform and dichloromethane), ethers (such as ethyl ether and tetrahydrofuran), esters (such as ethyl acetate), alcohols (such as methanol and ethanol), etc.

The reaction is carried out under ice cooling (about 0° C.) to the boiling point of the solvent (to about 100° C.), preferably at room temperature (about 15° to 25° C.) to about 80° C.

The reaction time is about 2 to 48 hours.

By subjecting the above compound [1'] to N-alkylation, N-alkenylation or N-alkynylation reaction (quarternary ammoniating reaction), a compound [1''] which corresponds to a compound [1] in which $R^a$ is the formula

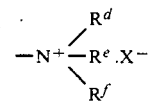

(wherein $R^d$, $R^e$, $R^f$ and $X^-$ have the same meanings as defined above) can be prepared.

Examples of the reagents to be used in the reaction include corresponding alkyl, alkenyl or alkynyl halides, esters, trioxonium salts, etc.

Examples of the halogen atoms in the halides include chlorine, bromine and iodine, particularly preferably iodine.

Examples of the esters include a sulfate ester and the likes.

Typical examples of the trioxonium salts include trimethyyloxonium fluoroborate, triethyloxonium fluorobrate, etc.

The reaction reagent is used in an amount of about 1 to 100 mol equivalent, preferably about 2 to 25 mol equivalent per one mol of the starting compound.

The solvent to be used in the reaction include, for example, haloganated hydrocarbons (such as chloroform and dichloromethane), ethers (such as ethyl ether and tetrahydrofuran), esters (such as ethyl acetate), alcohols (such as methanol and ethanol), etc.

The reaction is carried out under ice cooling (about 0° C.) to the boiling point of the solvent (about 100° C.), preferably at room temperature (about 15° to 25° C.) to about 80° C.

The reaction time is about 2 to 48 hours.

The quaternization can be conducted before or after the foregoing acylation reaction and the like, preferably thereafter.

From the reaction mixture, after carrying out optionally washing with aqueous sodium carbonate, or aqueous sodium chloride, drying or concentration, the product can be isolated by filtration of the precipitate formed by addition of an ether to obtain the desired products as a salt of the anion from the reagent used in quaternization.

When the reaction mixture is subjected to column chromatography with silica gel or ion exchange resin, using, for example, a mixture of chloroform-metanol added with conc. aqueous ammonia, a compound with hydroxide ion ($OH^-$) as the anion can be obtained.

The anions of the compound thus obtained can be exchanged with other anions by a conventional means.

The starting compound [5'] can be prepared by treating, for example, de(N-methyl)erythromycin A or bis [de(N-methyl)] erythromycin A [E. H. Flynn, et al., Journal of the American Chemical Society, 77, 3104 (1955), Japanese Laid-open Patent Application No. 9129/1972] under acidic conditions.

The compound [1] thus obtained can be isolated and purified in per se already known methods, for example concentration, pH alteration, solvent-transformation, solvent extraction, lyophilization, crystallization, recrystallization, distillation, chromatography etc.

The compound [1] may form a salt with an acid. Examples of such acids include organic acids (for example, ethylsuccinic acid, glycopeptonic acid, stearic acid, propionic acid, succinic acid, lactic acid, trifluoroacetic acid, acetic acid, methanesulfonic acid, paratoluenesulfonic acid, and benzenesulfonic acid) and mineral acids (for example, sulfuric acid, hydrochloric acid, hydriodic acid, phosphoric acid, nitric acid).

The raw material for preparing the compound [1] can be prepared, for example, by methods reported by W. Slawinski et al., Journal of the Royal Netherlands Chemical Society, 94 236, 1975; V. C. Stephens et at., Antibiotics Annual, 1958-1959, 346; P. H. Jones et al., Journal of Medicinal Chemistry, 15, 631, 1972; J. Tadanier et al., Journal of Organic Chemistry, 39, 2495, 1974; A. Banaszek et al., Roczniki Chemi, 43, 763, 1969; C. W. Pettinga et al., Journal of the American Chemical Sodiety, 76, 569, 1954; P. F. Wiley et al., Journal of the American Chemical Society, 79, 6074, 1957; J. Majer et al., Journal of the American Chemical Society, 99, 1620, 1977; and J. R. Martin et al., Journal of Antibiotics, 35, 426, 1982 or similar methods, or by subjecting the compounds described in the above-mentioned references to the above-described process or the conventional known means.

On the other hand, the starting compounds anhydroerythromycin A can be prepared according to the methods reported by P. Kurath, et al., Experientia, 27, 362 (1971), K. Krowichki and A. Zamojski, The Journal of Antibiotics, 26, 569 (1973), while 9-dihydroerythromycin A 6,9-epoxide and 9-dihydroerythromycin B 6,9-epoxide can be prepared according to the methods reported in Japanese Laid-open Patent Application No. 1588/1974.

The compound [1] or its salt has an excellent effect on stimulating the gastrointestinal contraction. Also, no lethal case was observed when the compound (55) described later is orally administered to mouse at a dose of 2300 mg/kg. Accordingly, the compound [1] be considered to be low in toxicity.

The compound [1] shows an excellent effect for stimulating the gastrointestinal contraction with a low toxicity, and the preparation of the present invention containing the compound [1] can therefore be utilized as a gastrointestinal contractive motion stimulant for the therapy of digestive malfunctions (nausea, vomiting, want of apetite in gastritis, gastric ulcer, duodenal ulcer, diseases in gallbladder and biliary tract, etc.) in mammals (mouse, rat, dog, cow, pig, man, etc.).

The digestive tract contractive motion stimulant of the present invention can be administered orally or non-orally to the above-mentioned mammals. The daily dose thereof, in case of oral administration, is ca. 0.0001-100 mg/kg in the form of the compound [1], and, in case of non-oral administration, for example, intravenous injection, is ca. 0.00001-10 mg/kg.

For example, a compound (32), to be explained later, induces an extremely strong contraction in the stomach, duodenum and small intestine in dog, by an intravenous administration of a dose of 1.0 mg/kg. The contractile motion is comparable to the strongest one in the gastrointestinal contraction in normal dog. Also a reduced dose in the order of 3 µg/kg induces, instead continuous strong contraction, a contractile motion of an identical pattern with that of the natural contraction inter digestive state.

The digestive tract contractile motion stimulant of the present invention can be formed into various preparations, containing the compound [1] and additional components, such as emulsion, hydrated mixture, tablet, solution, powder, granules, capsule, pill etc. Said additional components include pharmacologically permitted vehicle, disintegrator, lubricant, binder, dispersant, plasticizer etc. As examples of the additional components, the examples of vehicles are lcactose, glucose and white sugar; those of disintegrators are starch, sodium alginate, agar powder and carboxymethyl cellulose calcium; those of lubricants are magnesium stearate, talc and liquid paraffin; those of binders are syrup, gelatin solution, ethanol and polyvinyl alcohol; those of dispersants are methyl cellulose, ethyl cellulose and shellac; and those of plasticizers are glycerin and starch.

These preparations can be obtained by methods usually employed in the field of pharmaceuticals.

The present invention will now be clarified in further detail by reference examples and examples, but the present invention is not limited thereby.

PREFERRED EMBODIMENTS OF THE INVENTION

The gastrointestinal motion was measured in the following manner (Z. Itoh, Nihon Heikatsu-kin Gakkai Zasshi, 13, 33, 1976). A crossbreed adult dog of a weight of 10-15 kg was anesthethized and the abdominal cavity was opened, and force transducers were chronically sutured on the serosa of the gastrointestinal tract such as gastric body, gastric antrum, duodenum, jejunum, etc. in directions capable of recording the contraction of circular muscles. The lead wires were extracted from the back and fixed to the skin. The experiment could be started about 5 days after recovery from such operation, and a dog prepared in this manner can be subjected to experiments for about 6 months. The force transducer, when subjected to a bending stress by the contraction of the gastrointestinal tract where the transducer is sutured, allows to record the wave form corresponding to the applied force, on a pen-recording oscillograph, and this method allows to measure the nature and magnitude of the contraction.

The dog was maintained in an experimental cage, and the wave form of contraction can be immediately recorded by connecting the wires of the transducer to the polygraph. The gastrointestinal contractive motion can be divided, from the pattern of contraction, into the one in a period after food intake and it in an interdigestive period. The experiments were conducted, during the interdigestive period and in an inactive period lacking the contraction in the stomach. The sample was injected through a silicone tube placed in advance in the superior vena cava over 10 seconds.

The sample was dissolved in physiological saline to a total volume of 10 ml. and was slowly injected intravenously for a period of ca. 10 seconds.

The gastrointestinal motor stimulating activity (GMSA) is summarized in Table 1.

TABLE 1

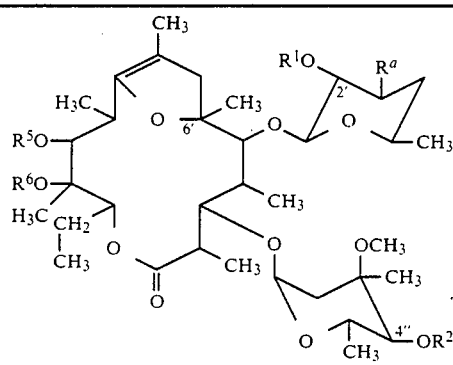

| Compound No.* | $R^1$ | $R^2$ | $R^5$ | $R^6$ | $R^a$ | GMSA |
|---|---|---|---|---|---|---|
| (5) | H | CH$_3$CO | H | H | $-N\begin{smallmatrix}CH_3\\CH_3\end{smallmatrix}$ | + |
| (9) | H | CHO | H | H | " | + + |
| (14) | H | CH$_3$CO | CH$_3$CO | H | " | + |
| (25) | H | CHO | CH$_3$SO$_2$ | H | " | + + + |
| (26) | H | CH$_3$SO$_2$ | CH$_3$SO$_2$ | H | " | + + |
| (28) | CH$_3$CH$_2$CH$_2$CO | H | H | H | " | + + |
| (30) | H | CH$_3$SO$_2$ | H | H | " | + |
| (32) | H | H | CH$_3$CO | CH$_3$CO | " | + + + |
| (33) | H | H | CH$_3$CH$_2$CO | CH$_3$CH$_2$CO | " | + + |
| (36) | H | H | $\rangle{=}S$ |  | $N\begin{smallmatrix}CH_3\\CH_3\end{smallmatrix}$ | + |
| (37) | H | H | $\rangle S{=}O$ |  | " | + |
| (39) | H | H | $\rangle B{-}Ph$ |  | " | + + |
| (47) | H | H | H | CH$_3$SCH$_2$ | " | + |

TABLE 1-continued

| Compound No.* | R¹ | R² | R⁵ | R⁶ | Rᵃ | GMSA |
|---|---|---|---|---|---|---|
| (50) | H | H | $CH_3CO$ | H | " | ++ |
| (51) | H | H | $CH_3CH_2CO$ | H | " | ++ |
| (52) | H | H | $CH_3CH_2CH_2CO$ | H | " | ++ |
| (54) | H | H | $(CH_3)_2C=$ | | " | + |
| (55) | H | H | H | H | $-N^{\oplus}(CH_3)_3 \cdot I^{\ominus}$ | +++ |
| (56) | H | H | $CH_3CO$ | $CH_3CO$ | " | +++ |
| (58) | H | H | $CH_3SO_2$ | H | " | +++ |
| (59) | H | CHO | $CH_3SO_2$ | H | " | +++ |
| (60) | H | H | H | H | $-N^{\oplus}(CH_3)_2(C_2H_5) \cdot I^{\ominus}$ | +++ |
| (62) | $CH_3CO$ | H | H | H | $-N^{\oplus}(CH_3)_3 \cdot I^{\ominus}$ | ++ |
| (73) | H | H | $CH_3(CH_2)_3CO$ | H | $-N(CH_3)_2$ | + |
| (74) | H | H | $CH_3(CH_2)_4CO$ | H | " | ++ |
| (75) | H | H | H | H | $-N(CH_3)H$ | +++ |
| (77) | H | H | H | H | $-N(CH_3)(C_2H_5)$ | +++ |
| (79) | H | H | H | H | $-N^{\oplus}(CH_3)(C_2H_5)_2 \cdot I^{\ominus}$ | +++ |
| (80) | H | H | H | H | pyrrolidin-1-yl | + |

TABLE 1-continued
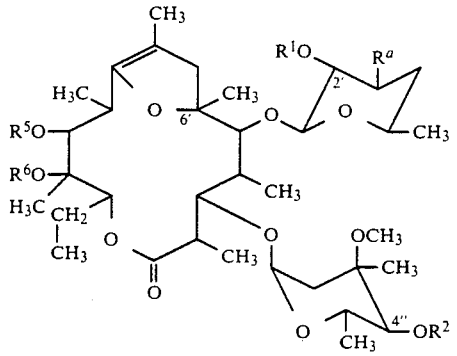
| Compound No.* | R¹ | R² | R⁵ | R⁶ | Rᵃ | GMSA |
|---|---|---|---|---|---|---|
| (81) | H | H | H | H | pyrrolidinium N⁺-CH₃ I⁻ | +++ |
| (82) | H | H | H | H | −N⁺(CH₃)(CH₃)(CH₂CH₂OH)·Br⁻ | +++ |
| (83) | H | H | H | H | −N⁺(CH₃)(CH₃)(CH₂CH=CH₂)·Br⁻ | +++ |
| (89) | H | H | H | H | −N⁺(CH₃)(CH₃)(CH₂Ph)·Cl⁻ | +++ |
| (90) | H | H | SO₂CH₃ | H | −N⁺(CH₃)(CH₃)(C₂H₅)·I⁻ | +++ |
| (91) | H | H | SO₂CH₃ | H | −N⁺(CH₃)(CH₃)(C₃H₇)·I⁻ | +++ |
| (92) (60-4) | H | H | H | H | −N⁺(CH₃)(CH₃)(C₂H₅)·Br⁻ | +++ |
| (97) | H | H | H | H | −N(C₂H₅)(C₂H₅) | ++ |
| (98) | H | H | H | H | −N(H)(C₂H₅) | +++ |
| (99) | H | H | H | H | piperidino | + |

TABLE 1-continued

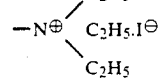

| Compound No.* | R¹ | R² | R⁵ | R⁶ | Rᵃ | GMSA |
|---|---|---|---|---|---|---|
| (100) | H | H | H | H | −N⁺(C₂H₅)₃·I⁻ | ++ |
| (101) | H | H | H | H | N-pyrrolidinyl, ⁺C₂H₅·I⁻ | + |
| (102) | H | H | H | H | N-piperidinyl, ⁺CH₃·I⁻ | +++ |
| (103) | H | H | H | H | N-piperidinyl, ⁺C₂H₅·I⁻ | + |
| (104) | H | H | H | H | −N⁺(CH₃)₂(CH₂C≡CH)·Br⁻ | ++++ |
| (105) | H | H | COCH₃ | COCH₃ | −N⁺(CH₃)₂(CH₂C≡CH)·Br⁻ | +++ |
| (106) | H | H | CH₃ | H | −N(CH₃)₂ | ++ |
| (108) | H | H | COC₂H₅ | COCH₃ | −N(CH₃)₂ | ++ |
| (109) | H | H | COC₃H₇ | COCH₃ | −N(CH₃)₂ | ++ |
| (110) | H | H | COCH₃ | COCH₃ | −N⁺(CH₃)₂(C₂H₅)·Br⁻ | +++ |
| (111) | H | H | H | H | −N⁺(CH₃)₂(CH₂CO₂CH₃)·Br⁻ | ++ |
| (112) | H | H | H | H | −N⁺(CH₃)₂(CH₂CO₂H)·Br⁻ | ++ |

TABLE 1-continued

[Structure diagram of macrolide compound with substituents R¹O, R⁵O, R⁶O, R², Rᵃ, OCH₃, CH₃ groups at positions 2', 4", 6']

| Compound No.* | R¹ | R² | R⁵ | R⁶ | Rᵃ | GMSA |
|---|---|---|---|---|---|---|
| (113) | H | H | H | H | $-\overset{+}{N}(CH_3)(CH_3)(CH_2CH_2F) \cdot Br^-$ | +++ |
| (114) | H | H | H | H | $-\overset{+}{N}(CH_3)(CH_3)(CH_2CN) \cdot Br^-$ | +++ |
| (117) | H | H | H | H | $-N(CH_3)(CH_2CH=CH_2)$ | ++ |
| (119) | H | H | H | H | $-N(CH_3)(CH_2CH_2CH_3)$ | +++ |
| (124) | H | H | H | H | $-N(H)(CH_2CH=CH_2)$ | ++ |
| (128) | H | H | H | H | $-\overset{+}{N}(CH_3)(CH_2CH=CH_2)_2 \cdot Br^-$ | ++ |
| (129) | H | H | H | H | $-\overset{+}{N}(CH_3)(CH_2CH=CH_2)(CH_2C\equiv CH) \cdot Br^-$ | +++ |
| (130) | H | H | H | H | $-\overset{+}{N}(CH_3)(CH_2C\equiv CH)_2 \cdot Br^-$ | +++ |
| (140) | H | H | H | H | $-\overset{+}{N}(CH_3)(CH_3)(CH_2C\equiv CH) \cdot Cl^-$ | ++++ |

TABLE 1'

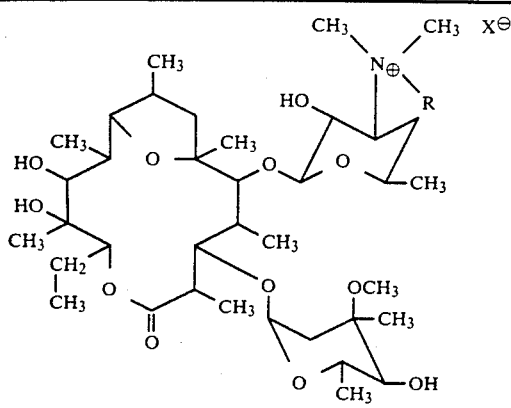

| Compound No. | R | X⊖ | GMSA |
|---|---|---|---|
| (85) | CH₃ | I⊖ | +++ |
| (86) | C₂H₅ | I⊖ | +++ |
| (87) | (CH₂)₂CH₃ | I⊖ | ++ |
| (88) | (CH₂)₃CH₃ | I⊖ | +++ |
| (115) | CH₂CH=CH₂ | Br⊖ | +++ |
| (116) | CH₂C≡CH | Br⊖ | +++ |

TABLE 1''

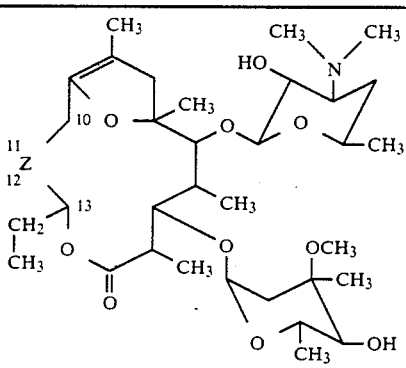

| Compound No. | Z | GMSA |
|---|---|---|
| *4 | ⧹11 12⧸ OH H CH₃ | ++ |
| *5 | ⧹12⧸ OH CH₃ | + |
| *6 | ⧹11 12⧸ O CH₃ | + |

In Tables 1, 1' and 1'', ++++, +++, ++ and + of GMSA respectively indicate that the minimum effective concentration required for inducing a gastrointestinal contractive motion in dog, comparable to the spontaneous one in the interdigestive period is in a range of 0.01–0.1 μg/kg, 0.1–10 μg/kg, 10–30 μg/kg and 30–50 μg/kg, respectively, (*1) The numbers of compounds correspond to those in the reference examples.

The process for preparing the compounds represented by *2, *5 and *6 is described in a reference, J. Tadanier et al., Journal of Organic Chemistry 39, 2495, 1974.

The process for preparing the compounds represented by *3 is described in a reference, W. Slawinski et al., Journal of the Royal Netherlands Chemical Society 94, 236, 1975.

The process for preparing the compounds represented by *4 is described in a reference, P. Kurath, et al., Experientia, 27, 362, 1971.

REFERENCE EXAMPLE 1

250 mg of 2'-0-acetyl-8,9-anhydroerythromycin A 6,9-hemiketal (compound 1) (V. C Stephens et al., Antibiotics Annual, 1958–1959, 346) was dissolved in 2 ml of dry pyridine, and 0.3 ml of acetyl chloride was added at a time at room temperature and under vigorous agitation. After agitation for 15 minutes, 30 ml of ethyl acetate was added. The obtained ethyl acetate solution was washed with the saturated agueous solution of sodium hydrogen carbonate, then with the saturated agueous solution of sodium chloride, then dried with anhydrous sodium sulfate, and the solvent was distilled off to obtain a crude product.

The crude product was purified by silica gel column chromatography (developed with a 50:1:0.01 mixed solvent of chloroform, methanol and concentrated agueous ammonia) to obtain 100 mg (yield 38%) of 2',4''-di-0-acetyl-8,9-anhydroerythromycin A 6,9-hemiketal (compound 2) as white powder.

REFERENCE EXAMPLE 2

303 mg of the compound 1, 0.3 ml of propionyl chloride and 2 ml of dry pyridine were employed in the process of Example 1 to obtain 143 mg (yield 44%) of 2'-0-acetyl-4''-0-propionyl-8,9-anhydroerythromycin A 6,9-hemiketal (compound 3) as white powder.

REFERENCE EXAMPLE 3

303 mg of the compound 1 was dissolved in 1 ml of dry pyridine and agitated overnight with 0.07 ml of benzoyl chloride. Thereafter the same process as in Reference Example 1 was adopted to obtain 127 mg (yield 37%) of 2'-0-acetyl-4''-0-benzoyl-8,9-anhydroerythromycin A 6,9-hemiketal (compound 4) in white powder.

REFERENCE EXAMPLE 4

100 mg of the compound 2 obtained in Reference Example 1 was dissolved in 2 ml of methanol, and agitated overnight at room temperature. A crude product, obtained by distilling off the solvent, was purified by silica gel column chromatography (developed by a 50:1:0.01 mixture of chloroform, methanol and concentrated aqueous ammonia) to obtain 35 mg. (yield 37%) of 4''-0-acetyl-8,9-anhydroerythromycin A 6,9-hemiketal (compound 5) in white powder.

REFERENCE EXAMPLE 5

143 mg of the compound 3 obtained in Reference Example 2 was dissolved in 2 ml of methanol, and processed in the same manner as in Reference Example 4 to obtain 83 mg (yield 61%) of 4''-0-propionyl-8,9-anhydroerythromycin A 6,9-hemiketal (compound 6)in white powder.

REFERENCE EXAMPLE 6

127 mg of the compound 4 obtained in Reference Example 3 was dissolved in 2 ml of methanol, and was processed in the same manner as in Reference Example 4 to obtain 92 mg (yield 77%) of 4''-0-benzoyl-8,9-anhydroerythromycin A 6,9-hemiketal (compound 7) in white powder.

REFERENCE EXAMPLE 7

59 mg of 2'-0-acetyl-4''-0-formyl-8,9-anhydroerythromycin A 6,9-hemiketal (compound 8) (J. Tadanier et al., Journal of Organic Chemistry, 39, 2495, 1974) was dissolved in 1 ml of methanol, and was processed in the same manner as in Reference Example 4 to obtain 29 mg of 4''-0-formyl-8,9-anhydroerythromycin A 6,9-hemiketal (compound 9) in white powder.

REFERENCE EXAMPLE 8

303 mg of the compound 1 was dissolved in 2 ml of dry pyridine, amd 0.3 ml of crotonyl chloride was added at a time under vigorous agitation at room temperature. After agitation for 15 minutes, 30 ml of ethyl acetate was added. The obtained ethyl acetate solution was washed with the saturated aqueous solution of sodium hydrogen carbonate and with the saturated aqueous solution of sodium chloride, then dried with anhydrous sodium sulfate and the solvent was distilled off.

The obtained residue was dissolved in 2 ml of methanol, and agitated overnight at room temperature. A crude product obtained by removing the solvent by distillation was purified by silica gel column chromatography (developed with a 50:1:0.01 mixture of chloroform, methanol and concentrated aqueous ammonia) to ob tain 31 mg (yield 10%) of 4''-0-crotonyl-8,9-anhydroerythromycin A, 6,9-hemiketal (compound 10) in white powder.

REFERENCE EXAMPLE 9

205 mg of the compound 1, 2 ml of dry 0.3 ml of butyryl chloride were processed in the same manner as in Reference Example 8 to obtain 18 mg (yield 8%) of 4''-0-butyryl-8,9-anhydroerythromycin A 6,9-hemiketal (compound 11) in white powder.

REFERENCE EXAMPLE 10

303 mg of the compound 1, 2 ml of dry pyridine and 0.4 ml of isovaleryl chloride were processed in the same manner as in Reference Example 8 to obtain 40 mg (yield 12%) of 4''-0-isovaleryl-8,9-anhydroerythromycin A 6,9-hemiketal (compound 12) in white powder.

REFERENCE EXAMPLE 11

303 mg of the compound 1, 2 ml of dry pyridine, and 0.4 ml. of ethylmalonyl chloride were processed in the same manner as in Reference Example 8 to obtain 40 mg (yield 12%) of 4''-0-ethylmalonyl-8,9-anhydroerythromycin A 6,9-hemiketal (compound 13) in white powder.

REFERENCE EXAMPLE 12

205 mg of the compound 1 was dissolved in 1 ml of dry pyridine, and agitated for 4 days at room temperature with 0.25 ml of acetic anhydride. The mixture was diluted with 30 ml of ethyl acetate, then washed with the saturated aqueous solution of sodium hydrogen carbonate and the saturated aqueous solution of sodium chloride, and dried with anhydrous sodium sulfate. The residue, obtained by distilling off the solvent, was dissolved in 1 ml of methanol and agitated overnight at room temperature. A crude product, obtained by removing the solvent by distillation, was purified with silica gel column chromatography (developed with a 50 : 1 : 0.01 mixture of chloroform, methanol and concentrated aqueous ammonia water to obtain 129 mg (yield 60%) of 11,4''-di-0-acetyl-8,9-anhydroerythromycin A 6,9-hemiketal (compound 14) in white powder.

REFERENCE EXAMPLE 13

205 mg of the compound 1, 1 ml of dry pyridine and 0.25 ml of propionic anhydride were processed in the same manner as in Reference Example 12 to obtaine 105 mg (yield 47%) of 11,4''-di-0-propionyl-8,9-anhydroerythromycin A 6,9-hemiketal (compound 15) in white powder.

REFERENCE EXAMPLE 14

205 mg of the compound 1 was dissolved in 1 ml of dry pyridine, and agitated with 0.5 ml of butyric anhydride for 7 days at room temperature. It was thereafter processed in the same manner as Reference Example 12 to obtain 113 mg (yield 40%) of 11,4''-di-0-butyryl-8,9-anhydroerythromycin A 6,9-hemiketal (compound 16) in white powder.

REFERENCE EXAMPLE 15

205 mg of the compound 1 was dissolved in 1 ml of dry pyridine, and agitated with 0.5 ml of benzoyl chloride for 3 days at room temperature. The mixture was then processed in the same manner as in Example 12 to obtain 107 mg (yield 35%) of 11,4''-di-0-benzoylerythromycin A 6,9-hemiketal (compound 17) in white powder.

REFERENCE EXAMPLE 16

184 mg of the compound 1 was dissolved in 2 ml of dry pyridine, and agitated with 440 mg of benzylsulfonyl chloride for 5 hours at room temperature. The mixture was then diluted with 30 ml of ethyl acetate, washed with the saturated aqueous solution of sodium hydrogen carbonate and with the saturated aqueous solution of sodium chloride, and dried with anhydrous sodium sulfate. The residue obtained by removing the solvent by distillation was dissolved in 2 ml of methanol, and agitated overnight at room temperature. A crude product obtained by removing the solvent by distillation wa purified by silica gel column chromatography (developed by a 50:1:0.01 mixture of chloroform, methanol and concentrated aqueous ammonia) to obtain 127 mg (yield 51%) of 11,4''-di-0-benzylsulfonyl-8,9-anhydroerythromycin A 6,9-hemiketal (compound 18) in white powder.

REFERENCE EXAMPLE 17

227 mg of the compound 1 was dissolved in 2 ml of dry pyridine, and agitated with 527 mg of paratoluenesulfonyl chloride for 2 days at 50° C. The mixture was processed in the same manner as in Reference Example 16 to obtain 81 mg (yield 26%) of 11,4''-di-0-paratoluenesulfonyl-8,9-anhydroerythromycin A 6,9-hemiketal (comp 19) in white powder.

REFERENCE EXAMPLE 18

9 g of 8,9-anhydroerythromycin A 6,9-hemiketal cyclic-11,12 carbonate (compound 20) (W. Slawinski et al., Journal of the Royal Netherlands Chemical Society, 94, 236, 1975) was dissolved in 100 ml of chloroform and agitated with 4 ml of pyridine and 3 ml of acetic anhydride for 45 minutes at room temperature. This reaction solution was washed with the saturated aqueous solution of sodium hydrogen carbonate and with the saturated aqueous solution of sodium chloride, then dried with anhydrous sodium sulfate, and the solven was distilled off to obtain white powder of 2'-0-acetyl-8,9-anhydroerythromycin A 6,9-hemiketal cyclic-11,12-carbonate (compound 21) quantatively in substatially pure state.

REFERENCE EXAMPLE 19

235 mg of the compound 21 obtained in Example 18 was dissolved in 1 ml of dry pyridine, and agitated with 0.5 ml butyric anhydride for 2 days at room temperature. The reaction solution was diluted with 30 ml of ethyl acetate, then washed with the saturated aqueous solution of sodium hydrogen carbonate and with the saturated aqueous solution of sodium chloride, dried with anhydrous sodium sulfate and the solvent was distilled off to obtain a crude product.

The crude product was purified by silica gel column chromatography (developed by a 50:1:−0.01 mixture of chloroform, methanol and concentrated aqueous ammonia) to obtain 78 mg (yield 31%) of 2'-0-acetyl-4''-0-butyryl-8,9-anhydroerythromycin A 6,9-hemiketal-cyclic-11,12-carbonate (compound 22) in white powder.

REFERENCE EXAMPLE 20

59 mg of the compound 22 obtained in Reference Example 19 was dissolved in 1 ml of methanol, and agitated overnight at room temperature. A crude product obtained by removing the solvent by distillation was purified by silica gel column chromatography (developed by a 50:1:0.01 mixture of chloroform, methanol and concentrated aqueous ammonia) to obtain 40 mg (yhield 72%) of 4'''-0-butyryl-8,9-anhydroerythromycin A 6,9-hemiketal-cyclic-11,12-carbonate (compound 23) in white powder.

REFERENCE EXAMPLE 21

79 mg of 11-0-methanesulfonyl-2'-0-acetyl-4''-0-formyl-8,9-anhydroeryth-romycin A 6,9-hemiketal (compound 24) (J. Tadaniel et al., Journal of Organic Chemistry, 39, 2495, 1974) was dissolved in 1 ml of methanol, and agitated overnight at room temperature. A crude product obtained by removing the solvent by distillation was purified by silica gel column chromatography (developed by a 50:1:0.01 mixture of chloroform, methanol and concentrated aqueous ammonia) to obtain 40 mg (yield 52%) of 11-0-methanesulfonyl-4''-0-formyl-8,9-anhydroerythromycin A 6,9-hemiketal (compound 25) in white powder.

REFERENCE EXAMPLE 22

150 mg of the compound 1 was dissolved in 2 ml of dry pyridine, and 46 μl of methanesulfonyl chloride was added thereto under agitation and under cooling with ice. After completion of the addition, agitation was continued for 1 hour under cooling with ice, and then for 2 hours at room temperature. The same process as in Example 16 was thereafter conducted to obtain 123 mg (yield 78%) of 11,4''-di-0-methanesulfonyl-8,9-anhydroerythromycin A 6,9-hemiketal (compound 26) in which powder.

Low mass (SIMS) m/e/ : 872 $(M+H)^+$

The structure, specific rotatory power and NMR spectrum values of the compounds obtained in Reference Example 1 to 22 are summarized in Tables 2 and 3.

TABLE 2

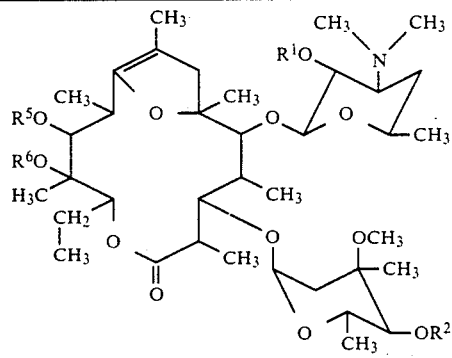

| Compound No. | $R^1$ | $R^2$ | $R^5$ | $R^6$ | $[\alpha]_D^{24}$ (c 1.0.CHCl$_3$) |
|---|---|---|---|---|---|
| 2 | CH$_3$CO | CH$_3$CO | H | H | −44.4° |
| 3 | CH$_3$CO | CH$_3$CH$_2$CO | H | H | −46.0° (c 0.5) |
| 4 | CH$_3$CO | PhCO | H | H | −56.2° |
| 5 | H | CH$_3$CO | H | H | −43.4° |
| 6 | H | CH$_3$CH$_2$CO | H | H | −38.0° |
| 7 | H | PhCO | H | H | −59.2° |
| 9 | H | CHO | H | H | −41.8° |
| 10 | H | CH$_3$−CH=CH−CO− | H | H | −43.4° |
| 11 | H | CH$_3$CH$_2$CH$_2$CO | H | H | −33.4° |
| 12 | H | (CH$_3$)$_2$CH−CH$_2$−CO− | H | H | −35.0° |

TABLE 2-continued

| Compound No. | R¹ | R² | R⁵ | R⁶ | $[\alpha]_D^{24}$ (c1.0,CHCl₃) |
|---|---|---|---|---|---|
| 13 | H | EtO-CO-CH₂-CO-CH₃ (ethyl acetoacetate group) | H | H | −34.8° |
| 14 | H | CH₃CO | CH₃CO | H | −21.4° |
| 15 | H | CH₃CH₂CO | CH₃CH₂CO | H | −25.6° |
| 16 | H | CH₃CH₂CH₂CO | CH₃CH₂CH₂CO | H | −25.4° |
| 17 | H | PhCO | PhCO | H | −50.0° |
| 18 | H | PhCH₂SO₂ | PhCH₂SO₂ | H | −37.6° |
| 19 | H | CH₃-C₆H₄-SO₂ | CH₃-C₆H₄-SO₂ | H | −9.0° |
| 21 | CH₃CO | H | >=O | | −33.6° |
| 22 | CH₃CO | CH₃CH₂CH₂CO | >=O | | −41.2° |
| 23 | H | CH₃CH₂CH₂CO | >=O | | −42.6° |
| 25 | H | CHO | CH₃SO₂ | H | −32.4° |
| 26 | H | CH₃SO₂ | CH₃SO₂ | H | −34.8° |

In Table 2, Ph is phenyl and Et is ethyl.
The numbers of compounds correspond to those in the Reference Examples.

TABLE 3

| | ³H-NMR peak (δ value ppm, solvent CDCl₃) | | | |
|---|---|---|---|---|
| Compound No. | 3″-OMe(s,3H) | 3′-NMe₂(s,6H) | 8-Me(s,3H) | Others |
| 2 | 3.35 | 2.28 | 1.55 | 2′-OAc: 2.05 (s,3H), 4″-OAc 2.10 (s,3H) |
| 3 | 3.35 | 2.28 | 1.55 | Ac: 2.04 (s,3H) |
| 4 | 3.34 | 2.33 | 1.55 | Ac: 2.06 (s,3H) Ph: 7.45(m,3H)  8.00(m,2H) |
| 5 | 3.33 | 2.31 | 1.57 | Ac: 2.10 (s,3H) |
| 6 | 3.32 | 2.32 | 1.57 | |
| 7 | 3.40 | 2.35 | 1.56 | Ph: 7.49 (m,3H)  8.01(m,2H) |
| 9 | 3.33 | 2.30 | 1.56 | CHO: 8.19(s,1H) |
| 10 | 3.33 | 2.31 | 1.56 | CH₃-CO-CH=CH-CH₃: 1.90(d,3H J=7Hz), CH₃-CO-CH=CH-CH₃: 7.00(m, 1H) CH₃-CO-CH=CH-H: 5.85(d,1H J=16Hz) |
| 11 | 3.32 | 2.29 | 1.55 | |
| 12 | 3.33 | 2.31 | 1.57 | |

TABLE 3-continued

| | $^3$H-NMR peak ($\delta$ value ppm, solvent $CDCl_3$) | | | |
|---|---|---|---|---|
| Compound No. | 3''-OMe(s,3H) | 3'-NMe$_2$(s,6H) | 8-Me(s,3H) | Others |
| 13 | 3.32 | 2.30 | 1.57 | $H\underset{\underset{O}{\|}}{\overset{\overset{O}{\|}}{\diagup\!\!\!\diagdown}}H$ OEt: 3.39(s,2H), O$\underline{CH}_2$CH$_3$: 4.19(q,1H J=8Hz) |
| 14 | 3.32 | 2.30 | 1.57 | 4''-OAc: 2.09(s,3H), 11-OAc: 2.12 (s,3H) |
| 15 | 3.31 | 2.28 | 1.57 | |
| 16 | 3.32 | 2.35 | 1.57 | |
| 17 | 3.41 | 2.35 | 1.56 | Ph: 7.49 (m,6H) 8.03(m,4H) |
| 18 | 3.33 | 2.28 | 1.53 | SO$_2$—$\underline{CH}_2$—Ph: 4.34 & 4.52 respectively (S,2H), Ph: 7.40(S, 10H) |
| 19 | 3.30 | 2.29 | 1.52 | —⟨O⟩—$\underline{CH}_3$: 2.44(s,6H), Ph: 7.30 & 7.80 respectively (m, 4H) |
| 21 | 3.46 | 2.36 | 1.58 | Ac: 2.05 (s,3H) |
| 22 | 3.34 | 2.28 | 1.58 | Ac: 2.05 (s,3H) |
| 23 | 3.28 | 2.26 | 1.57 | |
| 25 | 3.34 | 2.33 | 1.58 | SO$_2\underline{CH}_3$: 3.18(s,3H), CHO: 8.19(s,1H) |
| 26 | 3.32 | 2.27 | 1.56 | 4''-SO$_2$CH$_3$: 3.04(s,3H), 11-SO$_2$CH$_3$: 3.15(s,3H) |

In Table 3, Ac is acetyl and Phe is phenyl.

REFERENCE EXAMPLE 23

200 mg of 8,9-anhydroerythromycin A 6,9-hemiketal (compound 27) (V. C. Stephens et al., Antibiotics Annual, 1958–1959, 346) was dissolved in 3.4 ml of CHCl$_3$, then added with 0.22 ml of anhydrous pyridine and 0.34 ml of butyric anhydride, and was allowed to stand for 20 minutes at room temperature. The reaction solution was diluted with 20 ml of CHCl$_3$, and washed with 20 ml of the saturated aqueous solution of sodium hydrogen carbonate and 20 ml of water. The CHCl$_3$ layer was dried with anhydrous sodium sulfate, and concentrated under a reduced pressure to obtain a colorless glas-like substance. Said substance was purified by silica gel column chromatography, utilizing a developing mixed solvent of CHCl$_3$:CH$_3$OH:conc. NH$_4$OH=40:1:0.01, to obtain 209 mg (yield 95.2%) of 2'-0-butyryl-8,9-anhydroerythromycin A 6,9-hemiketal (compound 28) in white powder.

Rf value: 0.36 (CHCl$_3$:CH$_3$OH:conc. NH$_4$OH=10:1:0.01) Carrier:silica gel (Merck, est Germany), High mass: 785.4936 (calcd. for C$_{41}$H$_{71}$NO$_{13}$:785.4921).

The same carrier was employed also in the thin layer chromatography in the following Examples.

REFERENCE EXAMPLE 24

200 mg of 2'-0-acetyl-8,9-anhydroerythromycin A 6,9-hemiketal (compound 29) (V. C. Stephens et al., Antibiotics Annual, 1958–1959, 346) was dissolved in 4 ml of anhydrous pyridine, and added with 0.12 ml of methanesulfonyl chloride under cooling with ice. After 30 minutes, the same process as that for producing the compound 28 was conducted to obtain a colorless glas-like substance. This substance was dissolved, without purification in 8 ml of methanol and was let to stand at room temperature. After one day, the reaction solution was concentrated under reduced pressure to obtain a colorless glass-like substance. This substance was purified by silica gel column chromatography, utilizing a mixed developing solvent of CHCl$_3$:CH$_3$OH:conc. NH$_4$OH=30:1:0.01, to obtain 116 mg (yield 52.3%) of 4''-0-methanesulfonyl-8,9-anhydroerythromycin A 6,9-hemiketal (compound 30) in white powder.

Rf value: 0.20 (CHCl$_3$:CH$_3$OH:conc. NH$_4$OH=10:1:0.01), high mass: 793.427 (calcd. for C$_{38}$H$_{67}$NO$_{14}$S: 793.427).

REFERENCE EXAMPLE 25

300 mg of 2'-0-acetyl-4''-0-formyl-8,9-anhydroerythromycin A 6,9-hemiketal (compound 31) (=compound 8) (Journal of The Chemical Society, 39, 2495, 1974) was dissolved in 8.1 ml of CHCl$_3$, and heated under reflux with 5 mg of 4-dimethylaminopyridine, 15 ml of triethylamine and 1.2 ml of acetic anhydride. The reaction mixture was cooled to room temperature after 3 days, and the same process as that for obtaining the compound 28 was conducted to obtain a pale yellow glass-like substance. This substance was dissolved, without purification, in 12 ml of methanol, and heated under reflux. The solution was cooled to room temperature after 3 days and concentrated under reduced pressure to obtain a pale yellow glass-like substance. This substance was purified by silica gel column chromatography, utilizing a developing solvent system of CHCl$_3$:CH$_3$OH: conc. NH$_4$OH=50:1:0.01, to obtain 136 mg (yield 44.5%) of 11,12-di-0- acetyl-8,9-anhydroerythromycin A 6,9-hemiketal (compound 32) in white powder.

Rf value: 0.15 (CHCl$_3$:CH$_3$:conc. NH$_4$OH=10:1:0.01), low mass: M+799, high mass: 799.4703 (calcd. for C$_{41}$H$_{69}$NO$_{14}$: 799.4713).

REFERENCE EXAMPLE 26

300 mg of the compound 31 was dissolved in 8.1 ml of CHCl$_3$, then added with 5 mg of 4-dimethylaminopyridine, 2.2 ml of triethylamine and 2.2 ml of propionic anhydride, and processed in the same manner as in the preparation of the compound 32 to obtain 68 mg (yield 21.5%) of 11,12-di-0-propionyl-8,9-anhydroerythromycin A 6,9-hemiketal (compound 33) in white powder.

Rf value: 0.16 (CHCl$_3$:CH$_3$OH:conc. NH$_4$OH=10:1:0.01), high mass: 827.502 (calcd. for C$_{43}$H$_{73}$NO$_{14}$: 827.502).

REFERENCE EXAMPLE 27

300 mg of the compound 31 was dissolved in 8.1 ml of CHCl$_3$, then added with 5 mg of 4-dimethylaminopyridine, 2.2 ml of triethylamine and 2.6 ml of butyric anhydride, and processed in the same manner as in the preparation of the compound 32 to obtain 141 mg (yield 43.2%) of 11,12-di-0-butyryl-8,9-anhydroerythromycin A 6,9-hemiketal (compound 34) in white powder.

Rf value: 0.18 (CHCl$_3$:CH$_3$OH:conc. NH$_4$OH=10:1:0.01), low mass: M+855, high mass: 855.5343 (calcd. for C$_{45}$H$_{77}$NO$_{14}$:855.5339).

REFERENCE EXAMPLE 28

1.0 g of the compound 31 was dissolved in 10 ml of toluene, and heated under reflux with 929 mg of thiocarbonyl diimidazole. The solution was cooled to room temperature after 4 hours and processed in the same manner as in the preparation of the compound 28 to obtain a yellow glass-like substance. The obtained glass-like substance was purified by silica gel column chromatography, utilizing a developing solvent system of CHCl$_3$:CH$_3$OH:conc. NH$_4$OH=100:1: 0.01, to obtain 373 mg (yield 36.0%) of 2'-0-acetyl-4"'-0-formyl-8,9-anhydroerythromycin A 6,9-hemiketal-cyclic-11,12-thiocarbonate (compound 35) in white powder.

Rf value: 0.45 (CHCl$_3$:CH$_3$OH:conc. NH$_4$OH=10:1:0.01), high mass: 827.4091 (calcd. for C$_{41}$H$_{65}$NO$_{14}$S: 827.4121).

REFERENCE EXAMPLE 29

100 mg of the compound 35 was dissolved in 4 ml of methanol and heated under reflux. After 3 days, the solution was cooled to room temperature, and concentrated under reduced pressure to obtain a colorless glass-like substance. The obtained glass-like substance was purified by silica gel column chromatography, utilizing a developing solvent system of CHCl$_3$:CH$_3$OH:conc. NH$_4$OH=50:1: 0.01, to obtain 63 mg (yield 68.8%) of 8,9-anhydroerythromycin A 6,9-hemiketal-cyclic-11,12-thiocarbonate (compound 36) in white powder.

Rf value: 0.20 (CHCl$_3$:CH$_3$OH:conc. NH$_4$OH=10:1:0.01), high pass 757.4061 (calcd. for C$_{38}$H$_{63}$NO$_{12}$S: 757.407).

REFERENCE EXAMPLE 30

170 mg of the compound 27 was dissolved in 1.1 ml of methanol, then added with 213 mg of potassium carbonate and 27 μl of ethylene sulfite and agitated at room temperature. After 2 days, the solution was processed in the same manner as in the preparation of the compound 28 to obtain a colorless glass-like substance. The obtained glass-like substance was purified by silica gel column chromatography, utilizing a developing solvent system of CHCl$_3$:CH$_3$OH: conc. NH$_4$OH=10:1:0.01, to obtain 72 mg (yield 39.8%) of 8,9-anhydroerythromycin A 6,9-hemiketal-11,12-sulfite (compound 37) in white powder.

Rf. value: 0.09 (CHCl$_3$:CH$_3$OH:conc. NH$_4$OH=10:1:0.01), high mass: 761.401 (calcd. for C$_{37}$H$_{63}$NO$_{13}$S: 761.401).

REFERENCE EXAMPLE 31

200 mg of the compound 29 was dissolved in 10 ml of benzene, and heated under reflux with 32 mg of phenylboric acid. The solution was cooled to room temperature after 2 hours and processed in the same manner as in the preparation of the compound 28 to obtain 216 mg (yield 97.8%) of 2'-0-acetyl-8,9-anhydroerythromycin A 6,9-hemiketal-11,12-phenylboronate (compound 38) in white powder.

This compound was so pure that it did not require purification.

Rf value: 0.40 (CHCl$_3$:CH$_3$OH:conc. NH$_4$OH=10:1:0.01).

REFERENCE EXAMPLE 32

216 mg of the compound 38 obtained in Reference Example 31 was dissolved in 8.6 ml of methanol and was let to stand at room temperature. After 1 day, the solution was concentrated under a reduced pressure to obtain a colorless glass-like substance. The obtained glasslike substance was purified by silica gel column chromatography, utilizing a developing solvent system of CHCl$_3$:CH$_3$OH:conc. NH$_4$OH=50:1:0.01, to obtain 199 mg (yield 97.0%) of 8,9-anhydroerythromycin A 6,9-hemiketal-11,12-phenylboronate (compound 39) in white powder.

Rf value: 0.40 (CHCl$_3$:CH$_3$OH:conc. NH$_4$OH=10:1:0.01).

REFERENCE EXAMPLE 33

1.40 g of the compound 29 was dissolved in 14 ml of dry pyridine, then added with 1.1 ml of chlorotrimethylsilane and was let to stand at room temperature. After 2 hours, the solution was processed in the same manner as in the preparation of the compound 28 to obtain 1.50 g (yield 90.0%) of 2'-0-acetyl-11,4"-di-0-trimethylsilyl-8,9-anhydroerythromycin A 6,9-hemiketal (compound 40) as acolorless glass-like substance.

Rf value: 0.43 (CHCl$_3$:CH$_3$OH:conc. NH$_4$OH=10:1:0.01).

REFERENCE EXAMPLE 34

750 mg of the compound 40 was dissolved in 3 ml of 1,2-dichloromethane, then added with 2.40 g of tribenzylamine and 0.72 ml of acetayl chloride under cooling, and, after cooling 10 minutes, heated at 75° under agitation. After 3 days, the solution was processed in the same manner as in the preparation of the compound 28 to obtain a pale yellow solid substance. The obtained solid substance was dissolved, without purification, in 30 ml of methanol and heated at 50° C. The solution was cooled to room temperature after 1 day and concentrated under a reduced pressure to obtain a pale yellow solid substance. The obtained solid substance was purified by silica gel column chromatography, utilizing a developing solvent system of CHCl$_3$:CH$_3$OH: conc. NH$_4$OH=50:1:0.01, to obtain 163 mg (yield 25.9%) 25.9%) of 12-0-acetyl-8,9-anhydroerythromycin A 6,9-hemiketal (compound 41) as white powder.

Rf value: 0.15 (CHCl$_3$:CH$_3$OH:conc. NH$_4$OH=10:1:0.01), high mass: 757.460 (calcd. for C$_{39}$H$_{67}$NO$_{13}$: 757.460)

REFERENCE EXAMPLE 35

800 mg of the compound 40 was dissolved in 3.2 ml of 1,2-dichloroehane, then added with 2.56 g of tribenzylamine and 0.85 ml of propionyl chloride under cooling, and, after 10 minutes, heated at 75° C. under agitation. After 3 dayts, the solution was processed in the same manner as in the preparation of the compound 30 to obtain 273 mg (yield 39.(%) of 12-0-propionyl-8,9-anhydroerythromycin A 6,9-hemiketal (compound 42) as white powder.

Rf value: 0.17 (CHCl$_3$:CH$_3$OH:conc. NH$_4$OH=10:1:0.01), high mass: 771.476 (calcd. for C$_{40}$H$_{69}$NO$_{13}$: 771.476).

REFERENCE EXAMPLE 36

400 mg of the compound 29 was dissolved in 0.8 ml of dichloromethane, then added with 0.2 ml of N,N-diisopropylethylamine and 0.22 ml of methoxyethoxy methyl chloride under cooling, and, after 10 minutes, was let to stand at room temperature. After 3 hours, the same process as in the preparation of the compound 28 as conducted to obtain a colorless glass-like substance. The obtained glass-like substance was purified by silica gel column chromatography, utilizing a developing solvent system of CHCl:CH$_3$OH: conc. NH$_4$OH=100:1:0.01, to obtain 250 mg (yield 56.0%) of 2'-10-acetyl-4"-0-methoxyethoxymethyl-8,9-anhydro-erythromycin A 6,9-hemiketal (compound 43) as white powder.

Rf value: 0.43 (CHCl$_3$:CH$_3$OH:conc. NH$_4$OH=10:1:0.01), high mass: 845.513 (calcd. for C$_{43}$H$_{75}$NO$_{15}$: 845.513).

REFERENCE EXAMPLE 37

150 mg of the compound 43 obtained in Example 36 was dissolved in 6 ml of methanol and was let to stand at room temperature. After one day, the reaction solution was concentrated under reduced pressure to obtain a colorless glass-like substance. The obtained glass-like substance was purified by silica gel column chromatography, utilizing a developing solvent system of CHCl$_3$:CH$_3$OH:conc. NH$_4$OH=30:1:0.01, to obtain 85 mg (yield 59.6%) of 4"-0-methoxy-ethoxymetyyl-8,9-anhydroerythromycin A 6,9-hemiketal (compound 44) in white powder.

Rf value: 0.27 (CHCl$_3$:CH$_3$OH:conc. NH$_4$OH=10:1:0.01), high mass: 803.502 (calcd. for C$_{41}$H$_{73}$NO$_{14}$: 803.502).

The structure, speicific rotatory power and NMR spectrum of the compounds obtained in Reference Examples 23 -37 are summarized in Tables 4 and 5.

TABLE 4

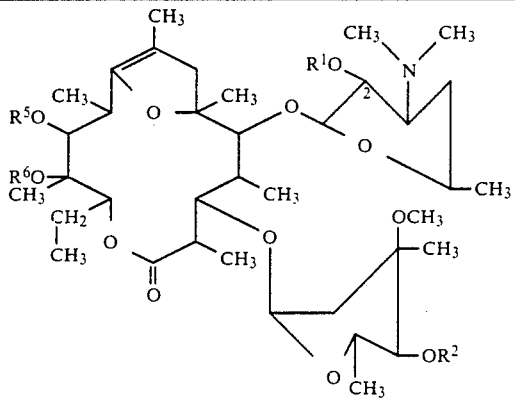

| Compound No. | $R^1$ | $R^2$ | $R^5$ | $R^6$ | $[\alpha]_D^{23}$ (c1.0, CHCl$_3$) |
|---|---|---|---|---|---|
| 28 | CH$_3$CH$_2$CH$_2$CO | H | H | H | −37.4° |
| 30 | H | CH$_3$SO$_2$ | H | H | −44.6° |
| 32 | H | H | CH$_3$CO | CH$_3$CO | −30.0° |
| 33 | H | H | CH$_3$CH$_2$CO | CH$_3$CH$_2$CO | −22.0° |
| 34 | H | H | CH$_3$CH$_2$CH$_2$CO | CH$_3$CH$_2$CH$_2$CO | −19.0° |
| 35 | CH$_3$CO | CHO | \>=S (spans R$^5$, R$^6$) | | +8.6° |
| 36 | H | H | \>=S (spans R$^5$, R$^6$) | | +25.0° |
| 37 | H | H | \>S=O (spans R$^5$, R$^6$) | | −30.2° |
| 38 | CH$_3$CO | H | \>B-Ph (spans R$^5$, R$^6$) | | −54.0° |
| 39 | H | H | \>B-Ph (spans R$^5$, R$^6$) | | −60.2° |
| 40 | CH$_3$CO | (CH$_3$)$_3$Si | (CH$_3$)$_3$Si | H | −35.6° |
| 41 | H | H | H | CH$_3$CO | −37.6° |
| 42 | H | H | H | CH$_3$CH$_2$CO | −65.2° (c 0.5) |
| 43 | CH$_3$CO | CH$_3$OCH$_2$CH$_2$OCH$_2$ | H | H | −30.4° |
| 44 | H | CH$_3$OCH$_2$CH$_2$OCH$_2$ | H | H | −34.0° |

In Table 4 Ph is phenyl. Si is sylyl.
The number of compounds correspond to those in Reference Examples.

TABLE 5

| Compound No. | 1H-NMR peak (δ value ppm. solvent CDCl3) | | | |
|---|---|---|---|---|
| | 8-Me(s,3H) | 3'-NMe2(s,6H) | 3"-OMe(s,3H) | Others |
| 28 | 1.51 | 2.25 | 3.20 | |
| 30 | 1.56 | 2.28 | 3.32 | 4"-SCH3 3.08(s,3H) |
| 32 | 1.53 | 2.20 | 3.34 | 12-COCH3 2.04(s,3H), 11-COCH3, 2.14(s,3H) |
| 33 | 1.52 | 2.28 | 3.34 | |
| 34 | 1.48 | 2.24 | 3.30 | |
| 35 | 1.58 | 2.28 | 3.34 | 2'-COCH3 2.00(s,3H), 4"-CHO 8.28(s,1H) |
| 36 | 1.58 | 2.28 | 3.25 | |
| 37 | 1.57 | 2.29 | 3.20 | |
| 38 | 1.57 | 2.31 | 3.35 | B-Ph 7.4~7.9(m,5H), 2'-COCH3 2.07(s,3H) |
| 39 | 1.63 | 2.33 | 3.39 | B-Ph 7.4~7.9(m,5H) |
| 41 | 1.51 | 2.20 | 3.31 | 12-COCH3 1.98(s,3H) |
| 42 | 1.56 | 2.32 | 3.32 | |
| 43 | 1.55 | 2.26 | 3.38 | 2-COCH3 2.04(s,3H),OCH2OCH2CH2OCH3 3.38(s,3H),4.83(s,2H) |
| 44 | 1.56 | 2.27 | 3.32 | OCH2OCH2CH2OCH3 3.38(s,3H), 4.83(s,2H) |

REFERENCE EXAMPLE 38

300 mg of the compound 27 was dissolved in 3 ml of dry pyridine, amd added with 0.4 ml of acetic anhydride. The reaction mixture was heated at 50° C. for 24 hours. The reaction solution as poured into 10 ml of the cold saturated aqueous solution of sodium hydrogen carbonate, and the resulting product was extracted with chloroform (3×10 ml). The extracting solution was dried with anhydrous sodium sulfate, and the solvent was removed under reduced pressure to obtain a crude product. This product was purified by silica gel column chromatography (Merck Art 7734 silica gel 20 g; eluting solvent chloroform-methanol [50: 1)] to obtain 290 mg of 11,2', 4"-tri-0-acetyl-8,9-anhydroerythromycin A 6,9-hemiketal (compound 45) as white powder.

Rf value: 0.38 (CHCl3:CH3OH=20:1).

REFERENCE EXAMPLE 39

290 mg of the compound 45 obtained in Reference Example 38 was dissolved in 3 ml of dry dimethyl sulfoxide, and added with 1 ml. of acetic anhydride. The reaction mixture was let to stand for 96 hours at room temperature. The reaction solution was concentrated under reduced pressure (<2 mm Hg), and the residue was dissolved in 20 ml of chloroform. The obtained chloroform solution was washed with 10 ml of the saturated aqueous solution of sodium hydrogen carbonate, then dried with anhydrous sodium sulfate, and the solvent was distilled off under reduced pressure. The crude produce was purified by silica gel column chromatography (Merck Art 7734 silica gel 20 g.; eluting solvent chloroform-methanol (50:1)), to obtain 173 mg of 11,2',4"-tri-0-acetyl-12-0-methylthiomethyl-8,9-anhydroerythromycin A 6,9-hemiketal (compound 46) as white powder.

Rf value: 0.39 (CHCl3:CH3OH=20:1).

REFERENCE EXAMPLE 40

173 mg of the compound 46 obtained in Reference Example 39 was dissolved in 5 ml of methanol, and added with 20 mg of lithium hydroxide. The reaction solution was heated at 50° C. for 4 hours under agitation. After concentration under a reduced pressure, the residue was dissolved in 20 ml of chloroform. The chloroform solution was washed with 10 ml of water, then was dried with anhydrous sodium sulfate, and the solvent was distilled off under reduced pressure. The crude product was purified by silica el column chromatography (Merck Art 7734 silica gel 15 g; eluting solvent:chloroform-methanol (30:1)), to obtain 118 mg of 12-0-methylthiomethyl-8,9-anhydroerythromycin A 6,9-hemiketal (compound 47) was white powder.

Rf value: 0.16 (CHCl3:CH3OH=10:1).

REFERENCE EXAMPLE 41

300 mg of the compound 8 was dissolved in 3 ml of dry pyridine, and added with 0.3 ml of acetic anhydride. The mixture was heated at 50° C. for 24 hours. The reaction solution was poured into 10 ml of the cold saturated aqueous solution of sodium hydrogen carbonate, and the resulting product was extracted with chloroform (3×10 ml). The extracting solution was dried with anhydrous sodium sulfate, and the solvent was distilled off under reduced pressure to obtain a crude product. This product was purified by silica gel column chromatography [Merck Art 7734 silica gel 20 g, eluting solvent : chloroform-methanol (50:1)] to obtain 195 mg of 11,2'-di-0-acetyl-4"-0-formyl- 8,9-anhydroerythromycin A 6,9-hemiketal (compound 48) as white powder.

Rf value: 0.37 (CHCl3:CH3=10:1) high mass: 827.4680 (calcd. for $C_{42}H_{69}NO_{15}$:827.4663).

REFERENCE EXAMPLE 42

195 mg of the compound 48 obtained in Example 41 was dissolved in 5 ml of methanol, and the solution was heated under reflux for 1 hour. Then the solvent was distilled off under a reduced pressure to obtain a crude product. This product was purified by silica gel column chromatography (Merck Art 7734 silica gel 20 g, eluting solvent : chloroform-methanol (30 : 1)) to obtain 155 mg of 11-0-acetyl-4"-0-formyl-8,9-anhydroerythromycin A 6,9-hemiketal (compound 49) as white powder.

Rf value: 0.28 (CHCl3:CH3CH3CH=10:1)

REFERENCE EXAMPLE 43

210 mg of the compound 48 obtained in Reference Example 41 was dissolved in 5 ml of methanol, and the solution was heated under reflux for 45 hours. Then the solvent was distilled off under reduced pressure to obtain a crude product. This product was purified by silica gel column chromatography (Merck Art 7734 silica gel 20 g, eluding solvent:chloroform-methanol (30:1)) to obtain 158 mg of 11-0-acetyl-8,9-anhydroerythromycin A 6,9-hemiketal (compound 50) as white powder.

Rf value: 0.21 (CHCl3:CH3OH=10:1).

REFERENCE EXAMPLE 44

155 mg of the compound 49 obtained in Reference Example 42 was processed in the same manner as in Example 43 to obtain 115 mg of 11-0-actyl-8,9-anhydroerythromycin A 6,9-hemiketal (compound 50) as white powder.

REFERENCE EXAMPLE 45

300 mg of the compound 8 was dissolved in 3 ml of dry pyridine, and added with 0.3 ml of acetic anhydride. The reaction mixture was heated at 50° C. for 24 hours. The reaction solution was poured into 10 ml of the cold saturated aqueous solution of sodium hydrogen carbonate, and the resulting product was extracted with chloroform (3×10 ml). The extract was dried with anhydrous sodium sulfate, and the solvent was distilled off under reduced pressure. The residue was dissolved in 5 ml of methanol, and heated under reflux for 45 hours. The solvent was distilled off under reduced pressure, and the residue was purified by silica gel column chromatography to obtain 156 mg of 11-0-acetyl-8,9-anhydroerythromycin A 6,9-hemiketal (compound 50) as white powder.

REFERENCE EXAMPLE 46

300 mg of the compound 8 and 0.3 ml of propionic anhydride were reacted according to the method of Reference Example 45, and the protection was removed with methanol. The crude product was purified by silica gel column chromatography (Merck Art 7734 silica gel 20 g, eluting solvent:chloroform-methanol (30:1 )) to obtain 152 mg of 11-0- propionyl-8,9-anhydroerythromycin A 6,9-hemiketal (compound 51) as white powder.

Rf value: 0.21 (CHCl$_3$:CH$_3$OH)=10:1).

REFERENCE NUMERAL 47

300 mg of the compound 8 and 0.3 ml of butyric anhydride were reacted and after removal of the protection according to the process of Reference Example 45, a crude product was obtained. This product was purified by silica gel column chromatography (Merck Art 7734 silica gel 20 g, eluting solvent:chloroform-methanol (30:1) to obtain 146 mg of 11-0-butyryl-8,9-anhydroerythromycin A 6,9-hemiketal (compound 52) as white powder.

Rf value: 0.21 (CHCl$_3$:CH$_3$OH=10:1)

REFERENCE EXAMPLE 48

300 mg of the compound 8 and 0.3 ml of benzoyl chloride were reacted and after removal of the protection according to the process of Reference Example 45, a crude product was obtained. This product was purified by silica gel column chromatography (Merck Art 7734 silica gel 20 g, eluting solvent:chloroform-methanol (30:1)) to obtain 155 mg of 11-0-benzoyl-8,9-anhydroerythromycin A 6,9-hemiketal (compound 53) as white powder;

Rf value: 0.20 (CHCl$_3$:CH$_3$OH=10:1)

REFERENCE EXAMPLE 49

200 mg of erythromycin A was dissolved in 2 ml of CHCl$_3$, then added with 78 µl of 2-methoxypropene and 64 mg of pyridinium chloride and let to stand at room temperature. After 1 day, the reaction solution was diluted with 20 ml of CHCl$_3$, and washed with 20 ml of the saturated aqueous solution of sodium hydrogen carbonate and 20 ml of water. The CHCl$_3$ layer was dried with anhydrous sodium sulfated and concentrated under a reduced pressure to obtain a colorless glass-like substance. The obtained glass-like substance was purified by silica gel column chromatography, utilizing a developing solvent system of CHCl$_3$:CH$_3$OH:conc. NH$_4$OH=30:1:0.01, to obtain 194 mg (94.0%) of 11,12-0-isopropylidene-8,9-anhydroerythromycin A 6,9-hemiketal (compound 54) as colorless powder.

Rf value: 0.14 (CHCl$_3$:CH$_3$OH:conc. NH$_4$OH=10: 1:0.01), high mass : 755.4856 (calcd. for C$_{40}$H$_{69}$NO$_{12}$:755.4815).

The structure, specific rotatory power and NMR spectrum of the compounds obtained in Examples 38–49 are summarized in Tables 6 and 7.

TABLE 6

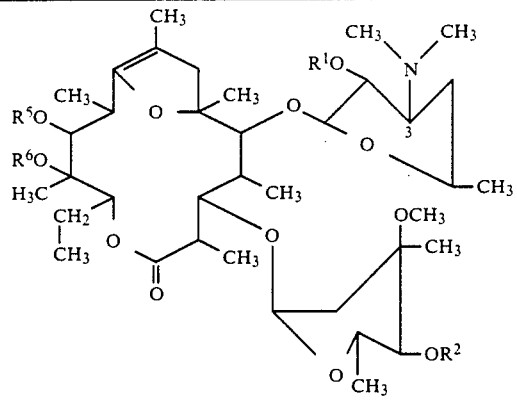

| Compound No. | R$^1$ | R$^2$ | R$^5$ | R$^6$ | $[\alpha]_D^{23}$ (c1.0.CHCl$_3$) |
|---|---|---|---|---|---|
| 45 | CH$_3$CO | CH$_3$CO | CH$_3$CO | H | −30.6° |
| 46 | CH$_3$CO | CH$_3$CO | CH$_3$CO | CH$_3$SCH$_2$ | −31.6° |
| 47 | H | H | H | CH$_3$SCH$_2$ | −28.6° |
| 48 | CH$_3$CO | CHO | CH$_3$CO | H | −25.6° |
| 49 | H | CHO | CH$_3$CO | H | −18.6° |
| 50 | H | H | CH$_3$CO | H | −18.0° |
| 51 | H | H | CH$_3$CH$_2$CO | H | −19.2° |
| 52 | H | H | CH$_3$CH$_2$CH$_2$CO | H | −20.4° |

TABLE 6-continued

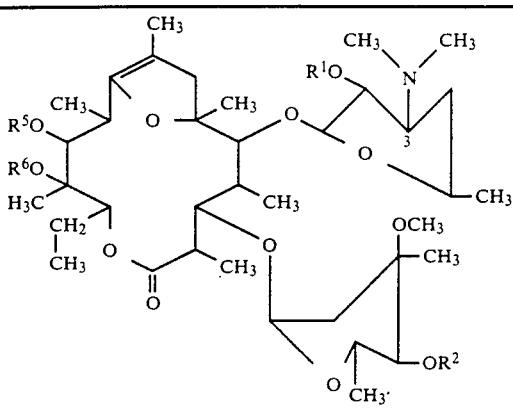

| Compound No. | R¹ | R² | R⁵ | R⁶ | $[\alpha]_D^{23}$ (c1.0,CHCl₃) |
|---|---|---|---|---|---|
| 53 | H | H | PhCO | H | −38.0° |
| 54 | H | H | CH₃\C=/CH₃ | | −24.8° |

In the Table 6, Ph is phenyl.
The numbers of compounds correspond to those in Reference Examples.

TABLE 7

| | ¹H-NMR peak (δ value ppm, solvent CDCl₃) | | | |
|---|---|---|---|---|
| Compound No. | 8-Me(s,3H) | 3'-NMe₂(s,6H) | 3''-OMe(s,3H) | Others |
| 45 | 1.56 | 2.30 | 3.35 | 2'-COCH₃2.06(s,3H),4''-COCH₃2.10(s,3H),11-COCH₃,2.12(s,3H) |
| 46 | 1.57 | 2.29 | 3.35 | 2'-COCH₃2.05(s,3H),4''-COCH₃2.08(s,3H),11-COCH₃, 2.10(s,3H), 12CH₂SCH₃,2.19(s,3H) |
| 47 | 1.54 | 2.30 | 3.29 | 12-CH₂SCH₃ 2.19(s,3H) |
| 48 | 1.57 | 2.28 | 3.37 | 2'-OAc 2.05(s,3H),11-OAc 2.12(s,3H),4''-OCHO 8.20(s,1H) |
| 49 | 1.58 | 2.30 | 3.35 | 11-OAc 2.12(s,3H),4''-OCHO 8.20(s,1H) |
| 50 | 1.58 | 2.31 | 3.36 | 11-OAc 2.13(s,3H) |
| 51 | 1.58 | 2.31 | 3.35 | |
| 52 | 1.58 | 2.31 | 3.35 | |
| 53 | 1.58 | 2.34 | 3.36 | 11-OBz 7.43 (m,3H), 8.05(m,2H) |

In Table 7, Ac is acetyl and Bz is benzoyl.

REFERENCE EXAMPLE 50

100 mg of the compound 27 was dissolved in 1 ml of chloroform and stirred for 2 hours with addition of 40 μl of methyl iodide. After most of the solvent was distilled off, 5 ml of ether was added and the precipitate formed was filtered. The precipitate was washed with ether and dried to obtain 65 mg (yield 54%) of 8,9-anhydroerythromycin A 6,9-hemiketal methyl iodide (compound 55) in white powder.

REFERENCE EXAMPLE 51

By using 30 mg of the compound 32 and 15 μl of methyl iodide, the same processing as in Reference Example 50 was conducted to obtain 18 mg (yield 51%) of 11,12-di0-acetyl-8,9-anhydroerythromycin A 6,9-hemiketal methyl iodide (compound 56) in white powder.

REFERENCE EXAMPLE 52

By using 79 mg of 11,0-methanesulfonyl-8,9-anhydroerythromycin A 6,9-hemiketal (compound 57) and 29 μl of methyl iodide, the same processing as in Reference Example 50 was conducted to obtain in 55 mg (yield 58%) of 11-0-methanesulfonyl-8,9-anhydroerythromycin A 6,9-hemiketal methyl iodide (compound 58) in white powder.

REFERENCE EXAMPLE 53

By using 78 mg of the compound 25 and 59 μl of methyl iodide, the same processing as in Reference Example 50 was conducted to obtain 67 mg (yield 74%) of 11-0-methane-sulfonyl-4''-0-formyl-8,9-anhydroerythromycin A 6,9-hemiketal methyl iodide (compound 59) in pale yellow powder.

REFERENCE EXAMPLE 54

200 mg of the compound 27 was dissolved in 4 μl of chloroform, then 0.5 ml of ethyl iodide was added thereto and the mixture was refluxed for 20 hours. After most of the solvent was distilled off under reduced pressure, 10 ml of ether was added and a precipitate formed was filtered. The precipitate was washed with ether and dried to obtain 145 mg (yield 60%) of 8,9-anhydroerythromycin A 6,9-hemiketal ethyl iodide (compound 60) in white powder.

REFERENCE EXAMPLE 55

200 mg of the compound 27 was dissolved in 4 ml of chloroform, then 0.5 ml of propyl iodide was added thereto and the mixture was refluxed for 48 hours. After the same processing as in Reference Example 54, 120 mg (yield 48%) of 8,9-anhydroerythromycin A 6,9-hemiketal propyl iodide (compound 61) was obtained in white powder.

REFERENCE EXAMPLE 56

200 mg of the compound (1) and 0.2 ml of methyl iodide were employed to carry out the same processing as in Reference Example 50. As the result, 154 mg (yield 65%) of 2'-0-acetyl-8,9-anhydroerythromycin A 6,9-hemiketal methyl iodide (compound 62) was obtained in white powder.

The structural formulae of the compounds obtained Reference 50 to 56 and their physical properties are shown in Table 8 and Table 9, respectively.

REFERENCE EXAMPLE 57

100 mg of the compound 27 was dissolved in 2 ml of dry ether and added with 73 μl of diisopropylethylamine and 33 μl of valeryl chloride at 0°. The mixture was warmed to room temperature, and stirred for 15 minutes at the same temperature, followed by dilution with addition of 25 ml of ethyl acetate. This was washed with the saturated aqueous sodium hydrogen carbonate and saturated aqueous sodium chloride solution, followed by drying over anhydrous sodium sulfate. The crude produce obtained by evaporation of the solvent was purified by silica gel chromatography (developing solvent:chloroform-methanol-conc. aqueous ammonia (20:1:0.01)) to obtain 96 mg (yield 86%) of 2'-0-varelyl-8,9- anhydroerythromycin A 6,9-hemiketal (compound 63) in white powder.

REFERENCE EXAMPLE 58

By using 50 mg of the compound 27, 37 μl of iisopropylethylamine and 20 μl of hexanoyl chloride, the same processing as in Reference Example 57 was con-

TABLE 8

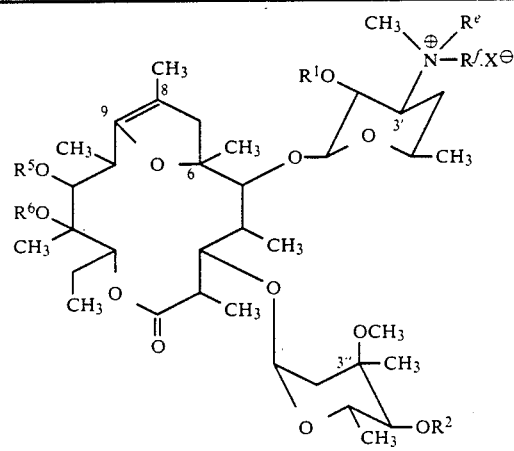

| Compound No. | $R^1$ | $R^2$ | $R^5$ | $R^6$ | $R^e$ | $R^f$ | X |
|---|---|---|---|---|---|---|---|
| 55 | H | H | H | H | $CH_3$ | $CH_3$ | I |
| 56 | H | H | $CH_3CO$ | $CH_3CO$ | $CH_3$ | $CH_3$ | I |
| 58 | H | H | $CH_3SO_2$ | H | $CH_3$ | $CH_3$ | I |
| 59 | H | CHO | $CH_3SO_2$ | H | $CH_3$ | $CH_3$ | I |
| 60 | H | H | H | H | $CH_3CH_2$ | $CH_3$ | I |
| 61 | H | H | H | H | $CH_3CH_2CH_2$ | $CH_3$ | I |
| 62 | $CH_3CO$ | H | H | H | $CH_3$ | $CH_3$ | I |

TABLE 9

| Compound No. | specific rotary power | NMR spectrum δ value ppm | | | |
|---|---|---|---|---|---|
| | | 8-Me(s.3H) | 3'-NMe | 3''-OMe(s,3H) | others(solvent) |
| 55 | $[\alpha]_D^{23}$-28.6° (c = 1.0,$CHCl_3$) | 1.58 | 3.64 (s,9H) | 3.49 | ($CDCl_3$) |
| 56 | $[\alpha]_D^{23}$-25.4° (c = 1.0,$CHCl_3$) | 1.51 | 3.48 (s,9H) | 3.37 | 1.99(11-$COCH_3$,s,3H), 2.03(12-$COCH_3$,s,9H) ($CDCl_3$) |
| 58 | $[\alpha]_D^{23}$-22.2° (c = 1.0,$CH_3OH$) | 1.59 | 3.35 (s,9H) | 3.43 | 3.18($SO_2CH_3$,s,3H) ($CDCl_3$) |
| 59 | $[\alpha]_D^{23}$-24.8° (c = 1.0,$CHCl_3$) | 1.58 | 3.34 (s,9H) | 3.54 | 3.16($SO_2CH_3$,s,3H) 8.28(CHO,s,1H) ($CDCl_3$) |
| 60 | $[\alpha]_D^{23}$-27.8° (c = 1.0,$CH_3OH$) | 1.59 | 3.19 (s.6H) | 3.38 | ($CD_3OD$) |
| 61 | $[\alpha]_D^{23}$-28.4° (c = 1.0,$CH_3OH$) | 1.58 | 3.12 (s,6H) | 3.38 | ($CD_3OD$) |
| 62 | $[\alpha]_D^{23}$-29.2° (c = 1.0,$CH_3OH$) | 1.58 | 3.22 (s,9H) | 3.40 | 2.19(2'-O-$COCH_3$,s.3H) ($CD_3OD$) | ducted to obtain 53 mg (yield 94%) of 2'-0-hexanoyl-8,9-anhydroerythromycin A 6,9-hemiketal (compound 64) in white powder.

REFERENCE EXAMPLE 59

By using 100 mg of the compound 27, 73 μl of diisopropylethylamine and 93 mg of arachidonyl chloride, the same processing as in Reference Example 57 was conducted to obtain 104 mg (yield 73%) of 2'-0-arachidonyl-8,9-anhydroerythromycin A 6,9-hemidetal (compound 65) in white powder.

REFERENCE EXAMPLE 60

By using 100 mg of the compound 27, 73 μl of diisopropylethylamine and 34 ml of isovaleryl chloride, the same processing as in Reference Example 57 was conducted to obtain 100 mg (yield 89%) of 2'-0-isovaleryl-8,9-anhydroery thromycin A 6,9-hemiketal (compound 66) in white powder.

REFERENCE EXAMPLE 61

By using 100 mg of the compound 27, 73 μl of diisopropylethylamine and 27 μl of crotonyl chloride, the same processing as in Reference Example 57 was conducted to obtain 87 mg (yield 79%) of 2'-0-crotonyl-8,9-anhydroery thromycin A 6,9-hemiketal (compound 67) in white powder.

REFERENCE EXAMPLE 62

By using 100 mg of the compound 27, 73 μl of diisopropylethylamine and 33 μl of benzoyl chloride, the same processing as in Reference Example 57 was conducted to obtain 87 mg (yield 75%) of 2'-0-benzoyl-8,9-anhydroerythromycin A 6,9-hemiketal (compound 68) in white powder.

REFERENCE EXAMPLE 63

200 mg of the compound 27 was dissolved in 4 ml of chloroform and 150 μl of diisopropylethylamine was added thereto After the mixture was heated to 50° C., 32 μl of methanesulfonyl chloride was added thereto and the mixture was stirred for 25 minutes, followed further by addition of 20 μl of methanesulfonyl chloride. After stirring for 15 minutes, the mixture was cooled to room temperature and diluted with 30 ml of ethyl acetate. This was washed with saturated aqueous sodium hydrogen carbonate and saturated aqueous sodium chloride solution, and dried over anhydrous sodium sulfate. The residue obtained by evaporation of the solvent was purified by silica gel chromatography (developing solvent: chloroform-methanol-conc. aqueous ammonia (60 : 1 : 0.01)) to obtain 53 mg of 2'-0-methanesulfonyl-8,9-anhydroerythromycin A 6,9-hemiketal (compound 69) (yield 24%) and 52 mg (yield 21%) of 11,2'-di-0-methanesulfony-8,9-anhydroerythromycin A 6,9-hemiketal (compound 70).

REFERENCE EXAMPLE 64

100 mg of the compound 27 was dissolved in 1 ml of dry pyridine, added with 0.3 ml of diphenylchlorophosphate and the mixture was stirred overnight. The mixture was diluted with 20 ml of ethyl acetate and the solution washed with saturated aqueous sodium hydrogen carbonate and saturated aqueous sodium chloride solution and was dried over anhydrous sodium sulfate and the solvent was evaporated. The crude product obtained was purified by silica gel chromatography [developing solvent: chloroformmethanol-conc. aqueous ammonia (10:1:0.01)] to obtain 43 mg (yield 33%) of 2'-0-diphenylphosphoryl-8,9-anhydroerythromycin A 6,9-hemiketal (compound 71) in white powder.

REFERENCE EXAMPLE 65

Using 100 mg of the compound 27, 1 ml of pyridine and 0.2 ml of diethylchlorophosphate, the same processing as in Reference Example 64 was conducted to obtain 25 mg (yield 21%) of 2'-0-diethylphosphoryl-8,9-anhydroerythromycin A 6,9-hemiketal (compound 72) in white powder.

REFERENCE EXAMPLE 66

157 mg of the compound (8) was dissolved in 1 ml of dry pyridine, added with 0.2 ml of valeric acid anhydride and the mixture was stirred at 50° C. for 2 weeks. After the mixture was cooled to room temperature, it was diluted with 30 ml of ethyl acetate and washed with saturated aqueous sodium hydrogen carbonate and saturated aqueous sodium chloride solution and dried over anhydrous sodium sulfate. The solvent was evaporated and the residue obtained was dissolved in 6 ml of methanol, followed by stirring at 50° C. for 3 hours. After cooling to room temperature and addition of 0.4 ml of 5% aqueous sodium hydrogen carbonate solution the mixture was further stirred for 6 hours. After concentration to a volume of about 2 ml, the concentrate was diluted with 30 ml of ethyl acetate and washed with saturated aqueous sodium chloride solution, followed by drying over anhydrous sodium sulfate. The crude product obtained by evaporation of the solvent was purified by silica gel chromatography [developing solvent: chloroform-methanol-conc. aqueous ammonia (10 : 1 : 0.1)]to obtain 91 mg (yield 57%) of 11-0-valeryl-8,9-anhydroerythromycin A 6,9-hemiketal (compound 73) in white powder.

REFERENCE EXAMPLE 67

By using 157 mg of the compound 8,1 ml of dry pyridine and 0.2 ml of hexanoic acid anhydride, the same processing as in Reference Example 66 was conducted to obtain 98 mg (yield 60%) of 11-0-hexanoyl-8,9-anhydroerythromycin A 6,9-hemiketal (compound 74) in white powder.

The structural formulae, specific rotatory powers and NMR spectrum values of the compounds obtained in Reference Examples 57-67 shown in Table 10.

TABLE 10

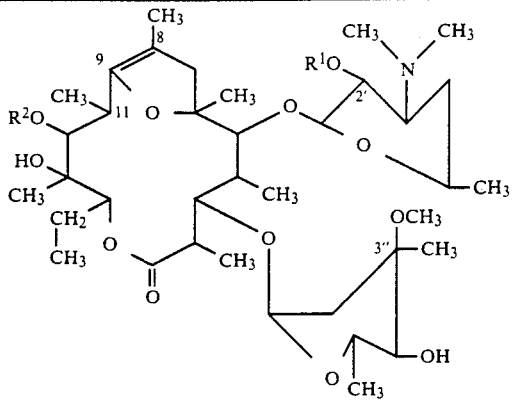

| compound No. | R¹ | R² | $[\alpha]_D^{23}$ (c1.0,CHCl₃) | 8-Me(s,3H) | 3-NMe₂(s,6H) | 3''-OMe(s,3H) | others |
|---|---|---|---|---|---|---|---|
| 63 | CO(CH₂)₃CH₃ | H | −39.2° | 1.55 | 2.25 | 3.38 | |
| 64 | CO(CH₂)₄CH₃ | H | −39.8° | 1.56 | 2.23 | 3.38 | |
| 65 | CO(CH₂)₁₈CH₃ | H | −20.4° | 1.55 | 2.25 | 3.38 | |
| 66 | COCH₂CH(CH₃)₂ | H | −37.2° | 1.55 | 2.24 | 3.37 | |
| 67 | COCH=CHCH₃ | H | −44.6° | 1.54 | 2.28 | 3.39 | 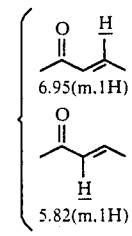 6.95(m,1H) 5.82(m,1H) |
| 68 | COPh | H | −43.6° | 1.52 | 2.30 | 3.46 | Ph: 7.45(m,3H), 8.00(m,2H) |
| 69 | SO₂CH₃ | H | −29.2° | 1.57 | 2.30 | 3.35 | SO₂CH₃: 3.17(s,3H) |
| 70 | SO₂CH₃ | SO₂CH₃ | −24.0° | 1.58 | 2.30 | 3.34 | SO₂CH₃: 3.17(s,3H) |
| 71 | PO(OPh)₂ | H | −42.4° | 1.57 | 2.33 | 3.37 | Ph: 7.23(m,10H) |
| 72 | PO(OEt)₂ | H | −42.4° | 1.56 | 2.28 | 3.32 | |
| 73 | H | CO(CH₂)₃CH₃ | −20.4° | 1.57 | 2.20 | 3.35 | |
| 74 | H | CO(CH₂)₄CH₃ | −17.8° | 1.57 | 2.30 | 3.35 | |

REFERENCE EXAMPLE 68

1.00 g of de(N-methyl) erythromycin A (reference: Japanese Laid-open Patent Application No. 9129/1972) was dissolved in 5 ml of glacial acetic acid and the solution was stirred for 1 hour. The reaction mixture was poured into 20 ml of ice-cooled conc. aqueous ammonia. The mixture was extracted 3 times with 10 ml of chloroform. The chloroform solution was dried over anhydrous sodium sulfate, and the solvent was evaporated under reduced pressure. The residue was purified by silica gel chromatography [developing solvent: chloroformmethanol-conc. aqueous ammonia (10:1:0.1)] to obtain 830 mg (yield 85%) of de(N-methyl)-8,9-anhydroerythromycin A 6,9-hemiketal (compound 75) in white powder.

REFERENCE EXAMPLE 69

930 mg of bis-[de(N-methyl)] erythromycin A (reference: Japanese Laid-open Patent Application No. 9129/1972) was processed in the same manner as in Reference Example 68 to obtain 770 mg (yield 85%) of bis [de(N-methyl)]-8,9-anhydroerythromycin A 6,9-hemiketal (compound 76) in white powder.

REFERENCE EXAMPLE 70

400 mg of ethyl-nor-erythromycin A [reference: R. K. Clark. Jr. et al. Antibiotics and Chemotherapy VII, 483, (1957)] was processed in the same manner as in Reference Example 68 to obtain 327 mg (yield 84%) of ethyl-nor-8,9-anhydroerythromycin A 6,9-hemiketal (compound 77) in white powder.

REFERENCE EXAMPLE 71

168 gm of butyl-nor-erythromycin A [reference: R. K. Clark, Jr. et al. Antibiotics and Chemotherapy VII, 483, (1957)] was processed in the same manner as in Reference Example 68 to obtain 99 mg (yield 60%) of butyl-nor-8,9-anhydroerythromycin A 6,9-hemiketal (compound 78) in white powder.

EXAMPLE EXAMPLE 72

88 mg of the compound 77 was dissolved in 2 ml of chloroform, then 1 ml of ethyl iodide was added thereto and the mixture was stirred at 80° C. for 14 hours. After most of the solvent was evaporated under reduced pressure, 5 ml of ether was added and the precipitate formed was filtered. The precipitate was washed with ether and dried to obtain 72 mg (yield 67%) of ethyl-nor-8,9-anhydroery- thromycin A 6,9-hemiketal ethyl iodide (compound 79) in white powder.

REFERENCE EXAMPLE 73

376 mg of the compound 76 was dissolved in 5 ml of methanol. 138 mg of sodium hydrogen carbonate and 1.0 ml of 1,4-dibromobuthane were added, and the mixture was stirred at 50° C. for 8 hours. The reaction mixture was diluted with 30 ml of ethyl acetate, and washed with water and saturated aqueous sodium chloride solution. The ethyl acetate solution was dried over anhydrous sodium sulfate and the solvent was evaporated under reduced pressure. The residue was purified by silica gel column chromatography [eluant: chloroform-methanol-conc. aqueous ammonia (10:1 :0.1)] to obtain 158 mg (yield 39%) of de(dimethylamino)-3'-pyrrolidino-8,9-anhydroerythromycin A 6,9-hemiketal (compound 80) in white powder.

REFERENCE EXAMPLE 74

By using 63 mg of the compound 80 and 0.1 ml of methyl iodide, the same processing as in Reference Example 50 was conducted to obtain 70 mg (yield 93%) of de(dimethylamino)-3'-pyrrolidino-8,9-anhydroerythromycin A 6,9-hemiketal methyl iodide (compound 81) in white powder.

REFERENCE EXAMPLE 75

120 mg of the compound 27 was dissolved in 1 ml of chloroform, then 0.5 ml of 2-bromoethanol and 0.5 ml of diisopropylethylamine were added thereto and the mixture was stirred for 2 days. After evaporation of the solvent, 5 ml of ether was added and the precipitate formed was filtered. The precipitate was washed with 10 ml of ether and dried to obtain 119 mg (yield 84%) of 8,9-anhydroerythromycin A 6,9-hemiketal 2-hydroxyethyl bromide (compound 82) in white powder.

REFERENCE EXAMPLE 76

150 mg of the compound 27 was dissolved in 1 ml of chloroform, then 0.5 ml of allylbromide and 0.25 ml of diisopropylethylamine were added thereto and the mixture was stirred for 1 day. After evaporation of the solvent, 5 ml of ether was added and a precipitate formed was filtered. The precipitate was washed with 10 ml of ether and dried to obtain 134 mg (yield 76%) of 8,9-anhydroerythromycin A 6,9-hemiketal allyl bromide (compound 83) in white powder.

The structural formulate, specific rotatory powers and NMR spectrum values of the compounds obtained in Reference Examples 68 to 76 are shown in Table 11.

TABLE 11

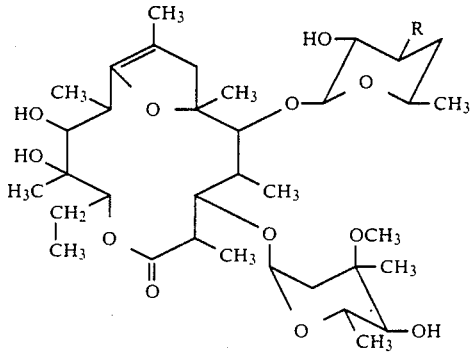

| Compound No. | R | Specific rotary power | NMR spectrum δ value ppm 8-Me(s,3H) | 3''-OMe(s,3H) | others (solvnt) |
|---|---|---|---|---|---|
| 75 | –N(H)(CH₃) | $[\alpha]_D^{23}$ −29.2° (c 1.0, CH₃OH) | 1.57 | 3.35 | 2.42 (NCH₃,s,3H) (CDCl₃) |
| 76 | NH₂ | $[\alpha]_D^{23}$ −43.2° (c 1.0, CHCl₃) | 1.57 | 3.31 | (CDCl₃) |
| 77 | –N(CH₃)(C₂H₅) | $[\alpha]_D^{23}$ −36.4° (c 1.0, CHCl₃) | 1.56 | 3.32 | 2.23 (NCH₃,s,3H) (CDCl₃) |
| 78 | –N(CH₃)(C₄H₉) | $[\alpha]_D^{23}$ −34.0° (c 1.0, CHCl₃) | 1.57 | 3.36 | 2.23 (NCH₃,s,3H) (CDCl₃) |
| 79 | –N⁺(CH₃)(C₂H₅)(C₂H₅)·I⁻ | $[\alpha]_D^{23}$ −27.0° (c 1.0, CH₃OH) | 1.58 | 3.38 | 3.05 (NCH₃,s,3H) (CD₃OD) |
| 80 | –N(pyrrolidino) | $[\alpha]_D^{23}$ −30.8° (c 1.0, CH₃OH) | 1.57 | 3.36 | (CDCl₃) |

TABLE 11-continued

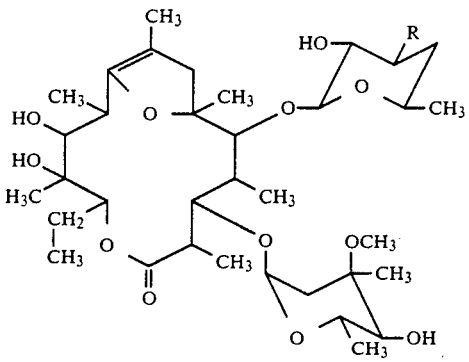

| Compound No. | R | Specific rotary power | NMR spectrum δ value ppm | | |
|---|---|---|---|---|---|
| | | | 8-Me(s,3H) | 3''-OMe(s,3H) | others (solvnt) |
| 81 | ![pyrrolidinium with N-CH3, I⊖] | $[\alpha]_D^{23}$ −27.0° (c 1.0, CH$_3$OH) | 1.58 | 3.37 | 2.98 (NCH$_3$,s,3H) (CD$_3$OD) |
| 82 | N⊕(CH$_3$)(CH$_3$)(CH$_2$CH$_2$OH), Br⊖ | $[\alpha]_D^{23}$ −26.4° (c 1.0, CH$_3$OH) | 1.54 | 3.34 | 3.34 (NMe$_2$,s,6H) (CD$_3$OD) |
| 83 | N⊕(CH$_3$)(CH$_3$)(CH$_2$CH=CH$_2$), Br⊖ | $[\alpha]_D^{23}$ −25.8° (c 1.0, CH$_3$OH) | 1.58 | 3.37 | 3.19 (NMe$_2$,s,6H) (CD$_3$OD) |

REFERENCE EXAMPLE 77

100 mg of 9-dihydroerythromycin A 6,9-epoxide (compound 84) (reference: Japanese Laid-open Patent Publication No. 1588/1972) was dissolved in 1 ml of chloroform, then 0.6 ml of methyl iodide was added thereto and the mixture was heated under reflux for 1.5 hours. After evaporation of the solvent, 5 ml of ether was added and the precipitate formed was filtered. The precipitate was washed with 10 ml of ether and dried to obtain 85 mg (yield 71%) 9-dihydroerythromycin A 6,9-epoxide methyl iodide (compound 85) in white powder.

REFERENCE EXAMPLE 78

100 mg of the compound 84 was dissolved in 1 ml of chloroform, then 0.6 ml of ethyl iodide was added thereto and the mixture was heated under reflux for 2 days. After evaporation of the solvent, 5 ml of ether was added and the precipitate formed was filtered. The precipitate was washed with 10 ml of ether and dried to obtain 90 mg (yield 74%) of 9-dihydroerythromycin A 6,9-epoxide ethyl iodide (compound 86) in white powder.

REFERENCE EXAMPLE 79

100 mg of the compound 84 was dissolved in 1 ml of chloroform, then 0.7 ml of propyl iodide was added thereto, and the mixture was heated under reflux for 2 days. After evaporation of the solvent, 5 ml of ether was added and the precipitate formed was filtered. The precipitate was washed with 10 ml of ether and dried to obtain 87 mg (yield 70%) of 9-dihydroerythromycin A 6,9-epoxide propyl iodide (compound 87) in white powder.

REFERENCE EXAMPLE 80

100 mg of the compound 84 was dissolved in 1 ml of chloroform, then 1.0 ml of butyl iodide was added thereto, and the mixture was heated under reflux for 1 days. After evaporation of the solvent, 5 ml of ether was added and the precipitate formed was filtered. The precipitate was washed with 10 ml of ether and dried to obtain 95 mg (yield 76%) of 9-dihydroerythromycin A 6,9-epoxide propyl iodide (compound 88) in white powder.

The structural formulae, specific rotatory powers and NMR spectrum values of the compound obtained in Reference Examples 77 to 80 are shown in Table 12.

TABLE 12

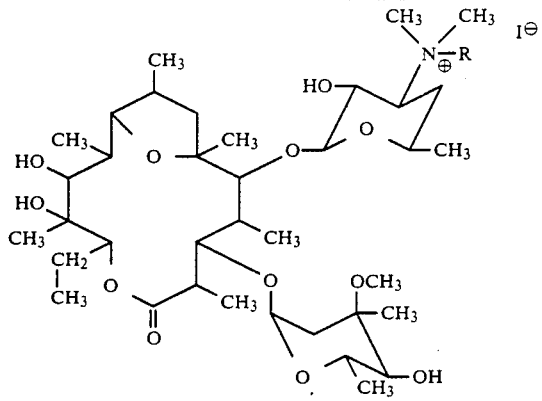

| Compound No. | R | $[\alpha]_D^{23}$ (c 1.0, CH$_3$OH) | NMR spectrum δ value ppm (CD$_3$OD) 3'-NMe(s) | 3''-OMe(s,3H) |
|---|---|---|---|---|
| 85 | CH$_3$ | −38.0° | 3.29(3'-NMe$_3$,9H) | 3.37 |
| 86 | C$_2$H$_5$ | −35.2° | 3.19(3'-NMe$_2$,6H) | 3.36 |
| 87 | CH$_2$CH$_2$CH$_3$ | −40.6° | 3.22(3'-NMe$_2$,6H) | 3.36 |
| 88 | CH$_2$CH$_2$CH$_2$CH$_3$ | −40.6° | 3.20(3'-NMe$_2$,6H) | 3.36 |

REFERENCE EXAMPLE 81

200 mg of the compound 27 was dissolved in 4 ml of chloroform, then 0.3 ml of benzyl chloride was added thereto and the mixture was heated under reflux for 48 hours. Subsequently, the same processing as in Reference Example 54 was conducted to obtain 122 mg (yield 52%) of 8,9-anhydroerythromycin A 6,9-hemiketal benzyl chloride (compound 89) in white powder.

REFERENCE EXAMPLE 82

200 mg of the compound 57 was dissolved in 4 ml of chloroform, then 0.5 ml of ethyl iodide was added thereto and the mixture was heated under reflux for 20 hours. Subsequently, the same processing as in Reference Example 54 was conducted to obtain 134 mg (yield 56%) of 8,9-anhydroerythromycin A 6,9-hemiketal ethyl iodide (compound 90) in pale yellow powder.

REFERENCE EXAMPLE 83

200 mg of the compound 57 was dissolved in 4 ml of chloroform, then 0.5 ml of ethyl iodide was added thereto and the mixture was heated under reflux for 20 hours. Subsequently, the same processing as in Reference Example 54 was conducted to obtain 126 mg (yield 52%) of 11-O-mesyl-8,9-anhydroerythromycin A 6,9-hemiketal ethyl iodide (compound 91) in pale yellow powder.

REFERENCE EXAMPLE 84

200 mg of the compound 27 was dissolved in 4 ml of chloroform, then 0.5 ml of ethyl bromide was added thereto and the mixture was heated under reflux for 48 hours. Subsequently, the same processing as in Reference Example 54 was conducted to obtain 189 mg (yield 82%) of 8,9-anhydroerythromycin A 6,9-hemiketal ethyl bromide (compound 92) in white powder.

The structural formulae, specific rotatory powers and NMR spectrum values of the compounds obtained in Reference Examples 81-84 are shown in Table 13.

TABLE 13

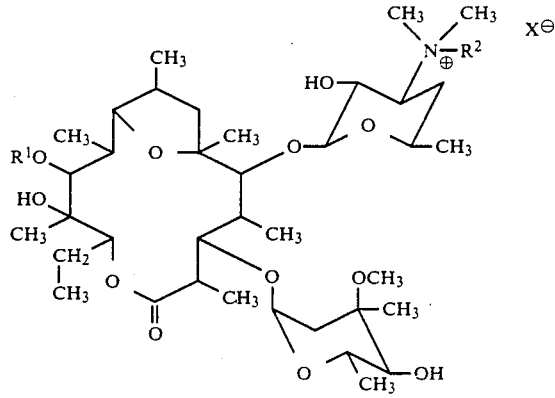

| Compound No. | R$^1$ | R$^2$ | X | $[\alpha]_D^{23}$ (c 1.0, CH$_3$OH) | NMR spectrum δ value ppm (CD$_3$OD) 8-Me(s,3H) | 3-NMe$_2$(s,6H) | 3''-OMe(s,3H) | others |
|---|---|---|---|---|---|---|---|---|
| 89 | H | —CH$_2$Ph | Cl | −39.6° | 1.59 | 3.09 | 3.34 | 7.54 (Ph, broad s,5H) |
| 90 | —SO$_2$CH$_3$ | C$_2$H$_5$ | I | −26.4° | 1.60 | 3.17 | 3.37 | 3.24 (SO$_2$CH$_3$,s,3H) |

TABLE 13-continued

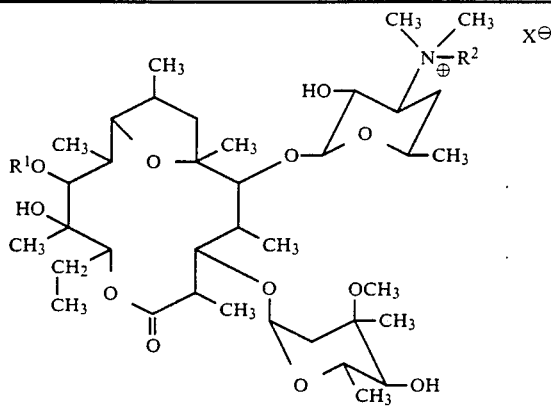

| Compound No. | R¹ | R² | X | $[\alpha]_D^{23}$ (c 1.0, CH₃OH) | NMR spectrum δ value ppm (CD₃OD) | | | |
|---|---|---|---|---|---|---|---|---|
| | | | | | 8-Me(s,3H) | 3-NMe₂(s,6H) | 3″-OMe(s,3H) | others |
| 91 | —SO₂CH₃ | CH₂CH₂CH₃ | I | −27.8° | 1.60 | 3.18 | 3.37 | 3.24 (SO₂CH₃,s,3H) |
| 92 | H | C₂H₅ | Br | −31.2° | 1.59 | 3.19 | 3.38 | |

REFERENCE EXAMPLE 85

By use of 68 mg of anhydroerythromycin A (compound 93) [reference: P. Kurath, et al., Experientia, 27, 362 (1971)] and 0.2 ml of ethyl iodide, the same processing as Reference Example 54 was conducted to obtain 69 mg of anhydroerythromycin A ethyl iodide (compound 94) in white powder (yield 75%).

REFERENCE EXAMPLE 86

By use of 105 mg of the compound (93) and 0.3 ml of propyl iodide, the same processing as Reference Example 55 was conducted to obtain 93 mg of anhydroerythromycin A propyl iodide (compound 95) in pale yellow powder (yield 72%).

REFERENCE EXAMPLE 87

By use of 105 mg of the compound (93) and 0.5 ml of benzyl chloride, the same processing as Reference Example 55 was conducted to obtain anhydroerythromycin A benzyl chloride (compound 96) in a yield of 75%.

The structural formulae, specific rotatory powers and NMR of the compounds obtained in Reference Examples 85 to 87 shown in Table 14.

TABLE 14

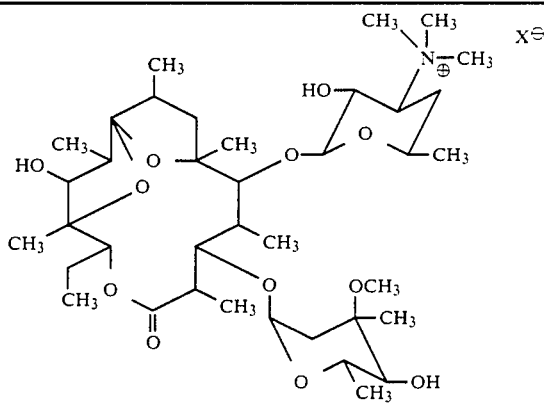

| compound No. | R | X | specific rotary power | NMR spectrum δ value ppm (CD₃OD) | | |
|---|---|---|---|---|---|---|
| | | | | 3″-OMe,S,3H | 3′-NMe₂,S,6H | others |
| 94 | C₂H₅ | I | $[\alpha]$ −35.8° (c 1.0, CH₃OH) | 3.25 | 3.39 | |
| 95 | C₃H₇ | I | $[\alpha]$ −34.0° (c 1.0, CH₃OH) | 3.29 | 3.29 | |
| 96 | CH₂Ph | Cl | $[\alpha]$ −18.6° (c 1.0, CH₃OH) | 3.32 | 3.10 | 7.57 (Ph,m,5H) |

REFERENCE EXAMPLE 88

206 mg of the compound 76 was dissolved in 3 ml of methanol, then 76 mg of sodium hydrogen carbonate and 0.5 ml of ethyl iodide were added thereto, and the mixture was stirred at 50° C. overnight. This reaction mixture was diluted with 30 ml of ethyl acetate, and washed with a saturated aqueous sodium hydrogen carbonate and saturated aqueous sodium chloride solution. The ethyl acetate solution was dried over anhydrous sodium sulfate and the solvent was evaporated under reduced pressure. The residue was purified by silica gel column chromatography (developing solvent: chloroform-methanol-conc. aqueous ammonia (50:1:

0.1)) to obtain 98 mg (yield 44%) of diethyl-dinor-8,9-anhydroerythromycin A 6,9-hemiketal (compound 98).

REFERENCE EXAMPLE 89

By using 550 mg of the compound 76, 1-6 ml of 1,5-dibromopentane and 202 mg of sodium hydrogen carbonate, the same processing as in Reference Example 73 was conducted to obtain 327 mg (yield 54%) of de(dimethylamino)-3'-piperidyl-8,9-anhydroerythromycin A 6,9-hemiketal (compound 99) in white powder.

REFERENCE EXAMPLE 90

By using 78 mg of the compound 97 and 1 ml of ethyl iodide, the same processing as in Reference Example 72 was conducted to obtain 15 mg (yield 16%) of diethyl-dinor-8,9-anhydroerythromycin A 6,9-hemiketal ethyl iodide (compound 100) in pale yellow powder.

REFERENCE EXAMPLE 91

By using 93 mg of the compound 80 and 1 ml of ethyl iodide, the same processing as in Reference Example 72 was conducted to obtain 94 mg (yield 84%) of de(dimethylamino)-3'-pyrrolidino-8,9-anhydroerythromycin A 6,9-hemiketal ethyl iodide (compound 101) in pale yellow powder.

REFERENCE EXAMPLE 92

83 mg of the compound 99 and 0.5 ml of methyl iodide were dissolved in 0.5 ml of chloroform, and stirred at 40° C. for 9 hours. Thereafter, the same processing as in Example 50 was conducted to obtain 84 mg (yield 85%) of de(dimethylamino)-3'-piperidino-8,9-anhydroerythromycin A 6,9-hemiketal methyl iodide (compound 102) in pale yellow powder.

REFERENCE EXAMPLE 93

By using 94 mg of the compound 99 and 1 ml of ethyl iodide, the same processing as in Reference Example 72 was conducted to obtain 33 mg (yield 29%) of de(dimethylamino)-3'-piperidino-8,9-anhydroerythromycin A 6,9-hemiketal ethyl iodide (compound 103) in pale yellow powder.

REFERENCE EXAMPLE 94

By using 50 mg of the compound 27 and 0.6 ml of propargyl bromide, the same processing as in Reference Example 50 was conducted to obtain 52 mg (yield 89%) of 8,9-anhydroerythromycin A 6,9-hemiketal propargyl bromide (compound 104) in white powder.

REFERENCE EXAMPLE 95

By using 111 mg of the compound 32 and 0.12 ml of propargyl bromide, the same processing as in Reference Example 50 was conducted to obtain 111 mg (yield 87%) of 11,12-di-0-acetyl-8,9-anhydroerythromycin A 6,9-hemiketal propargyl bromide (compound 105) in white powder.

The structural formula, specific rotatory powers and NMR spectrum values of the compounds obtained in Reference Examples 88-95 are shown in Table 15.

TABLE 15

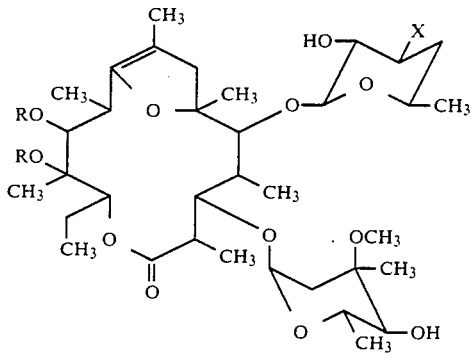

| Compound No. | R | X | Specific rotary power | NMR spectrum δ value ppm | | |
|---|---|---|---|---|---|---|
| | | | | 8-Me(s,3H) | 3'''-OMe(s,3H) | others (solvent) |
| 97 | H | N(C₂H₅)₂ | [α]$_D^{22}$ −27.2° (c 1.0, CHCl₃) | 1.56 | 3.36 | (CDCl₃) |
| 98 | H | NH / C₂H₅ | [α]$_D^{22}$ −34.8° (c 1.0, CHCl₃) | 1.56 | 3.35 | (CDCl₃) |
| 99 | H | N(piperidino) | [α]$_D^{22}$ −33.8° (c 1.0, CHCl₃) | 1.56 | 3.35 | (CDCl₃) |
| 100 | H | N⊕(C₂H₅)₃·I⊖ | [α]$_D^{22}$ −24.2° (c 1.0, CH₃OH) | 1.59 1.59 | 3.37 3.37 | (CD₃OD) (CD₃OD) |
| 101 | H | ⊕N-C₂H₅ (pyrrolidino) I⊖ | [α]$_D^{22}$ −27.0° (c 1.0, CH₃OH) | 1.59 | 3.35 | (CD₃OD) |

TABLE 15-continued

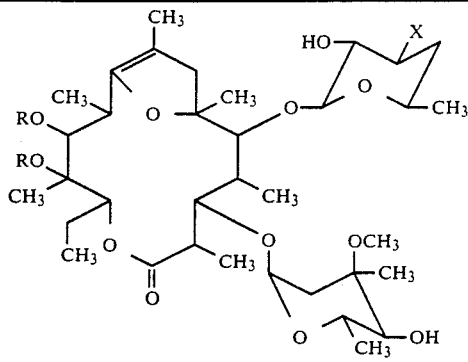

| Compound No. | R | X | Specific rotary power | NMR spectrum δ value ppm 8-Me(s,3H) | 3"-OMe(s,3H) | others (solvent) |
|---|---|---|---|---|---|---|
| 102 | H | ![cyclohexyl-N+(CH3), I−] | $[\alpha]_D^{22}$ −27.0° (c 1.0, CH$_3$OH) | 1.58 | 3.38 | 3.13 (3'-NMe,s,3H) (CD$_3$OD) |
| 103 | H | ![cyclohexyl-N+(C2H5), I−] | $[\alpha]_D^{22}$ −26.6° (c 1.0, CH$_3$OH) | 1.57 | 3.36 | (CD$_3$OD) |
| 104 | H | CH$_3$, N$^\oplus$—CH$_3$ Br$^\ominus$, CH$_2$—C≡CH | $[\alpha]_D^{22}$ −31.0° (c 1.0, CH$_3$OH) | 1.58 | 3.39 | 3.26 (3'-NMe$_2$,s,6H) (CD$_3$OD) |
| 105 | COCH$_3$ | CH$_3$, N$^\oplus$—CH$_3$ Br$^\ominus$, CH$_2$—C≡CH | $[\alpha]_D^{22}$ −20.0° (c 1.0, CH$_3$OH) | 1.51 | 3.39 | 2.01 (11-COCH$_3$,s,3H) 2.04 (12-COCH$_3$,s,3H) 3.27 (3'-NMe$_2$,s,6H) (CD$_3$OD) |

REFERENCE EXAMPLE 96

120 mg of 11-0-methylerythromycin A (reference: Japanese Laid-open Patent Publication No. 192294/1982) was dissolved in 6 ml of glacial acetic acid and the solution was stirred for one and a half hours. The reaction mixture was poured into 15 ml of ice-cooled conc. aqueous ammonia. This mixture was extracted 3 times with 10 ml of chloroform. This chloroform solution was dried over anhydrous sodium sulfate, and the solvent was evaporated under reduced pressure. The residue was purified by silica gel chromatography (developing solvent:chloroform-methanol-conc. aqueous ammonia (20:1:0.01)) to obtain 95 mg (yield 75%) of 11-0-methyl-8,9-anhydroerythromycin A 6,9-hemiketal (compound 106) in white powder.

REFERENCE EXAMPLE 97

125 mg of 11-0-ethylerythromycin A (reference: Japanese Laid-open Patent Publication No. 192294/1982) was treated in the same manner as in Reference Example 96 to obtain 102 mg (yield 84%) of 11-0-ethyl-8,9-anhydroerythromycin A 6,9-hemiketal (compound 107) in white powder.

REFERENCE EXAMPLE 98

120 mg of the compound 48 was dissolved in 3.2 ml of chloroform, then added with 2 mg of 4-dimethyl aminopyridine, 0.86 ml of triethylamine and 0.86 ml of propionic anhydride, and heated under reflux for 3 days. The reaction mixture was cooled to room temperature and the same process as that for obtaining the compound 28 was conducted to obtain a pale yellow glass-like substance. This substance was dissolved, without purification, in 6 ml of methanol, and heated under reflux for 3 days. The solution was cooled to room temperature and concentrated under reduced pressure to obtain a pale yellow glass-like substance. This substance was purified by silica gel column chromatography, utilizing a developing solvent system of chloroform-methanol-conc. aqueous ammonia=50:1:0.01, to obtain 65 mg (yield 55%) of 11-0-propionyl-12-0-acetyl-8,9-anhydroerythromycin A 6,9-hemiketal (compound 108) in white powder.

Rf value: 0.16 (chloroform:methanol:conc. aqueous ammonia=10:1:0.01), low mass: M+813, high mass: 813.486 (calcd, for C$_{42}$H$_{71}$NO$_{14}$: 813.487)

REFERENCE EXAMPLE 99

120 mg of the compound 48 was dissolved in 3.2 ml of chloroform, then added with 2 mg of 4-dimethylaminopyridine, 0.86 ml of triethylamine and 0.86 ml of butyric anhydride, and processed in the same manner as in the preparation of the compound 108 to obtain 75 mg (yield 63%) of 11-0-butyryl-12-0-acetyl-8,9-anhyroery- thromycin A 6,9-hemiketal (compound 109) in white powder.

Rf value: 0.16 (chloroform-methanol-conc. aqueous ammonia=10:1:0.01), low mass: M+827, high mass: 827.502 (calcd. for $C_{43}H_{73}NO_{14}$:827.502).

REFERENCE EXAMPLE 100

100 mg of the compound 32 was dissolved in 1 ml of chloroform and heated under rellux for 2 days with addition of 0.5 ml of ethyl bromide. Thereafter, the same processing as in Reference Example 50 was conducted to obtain 98 mg (yield 86%) of 11,12-di-0-acetryl-8,9-anhydroerythromycin A 6,9-hemiketal ethyl, bromide (compound 110) in white powder.

REFERENCE EXAMPLE 101

150 mg of the compound 27 was dissolved in 1 ml of chloroform, them 1 ml of bromoacetate and 0.5 ml of diisopropylethylamine were added thereto and the mixture was stirred for 6 hours. After evaporation of the solvent, 5 ml of ether was added and the precipitate formed was filtered. The precipitate was washed with 10 ml of ether and dried to obtain 145 mg (yield 80 %) of 8,9- anhydroerythromycin A 6,9-hemiketal methoxycarbonyl methyl bromide (compound 111) in white powder.

REFERENCE EXAMPLE 102

150 mg of the compound 27 was dissolved in 1 ml of chloroform, then 200 mg of bromoacetic acid and 0.5 ml of diisopropylethylamine were added thereto and the mixture was heated under reflux for 6 hours. After evaporation of the solvent 5 ml of ether was added and the precipitate formed was filtered. The precipitate was washed with 10 ml of ether and dried to obtain 127 mg (yield 71%) of 8,9-anhydroerythromycin A 6,9-hemiketal carboxymethyl bromide (compound 112) in white powder.

REFERENCE EXAMPLE 103

150 mg of the compound 27 was dissolved in 1 ml of chloroform, then 0.5 ml of monofluoroethyl bromide was added thereto and the mixture was heated under reflux for 5 days. Subsequently, the same processing as in Reference Example 75 was conducted to obtain 135 mg (yield 76%) of 8,9-anhydroerythromycin A 6,9-hemiketal 2-fluoroethyl bromide (compound 13) in white powder.

REFERENCE EXAMPLE 104

150 mg of the compound 27 was dissolved in 1 ml of chloroform, then 0.5 ml of bromoacetonitrile was added thereto and the mixture was allowed to stand at room temperature for 5 hours. Subsequently, the same processing as in Reference Example 75 was conducted to obtain 165 mg (yield 94 %) of 8,9-anhydroerythromycin A 6,9-hemiketal cyanomethyl bromide (compound 114) in white powder.

The structural formulae, specific rotatory powers and NMR spectrum values of the compounds obtained in Reference Examples 96–104 are shown in Table 16.

TABLE 16

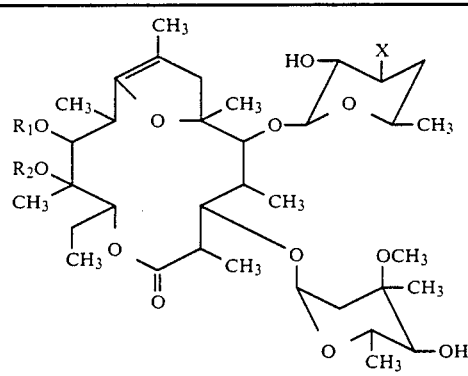

| Compound No. | $R^1$ | $R^2$ | X | Specific rotary power | NMR spectrum δ value ppm | | | |
|---|---|---|---|---|---|---|---|---|
| | | | | | 8-Me(s,3H) | 3'-NMe$_2$ (s,6H) | 3'-OMe(s,3H) | others (solvent) |
| 106 | $CH_3$ | H | $N(CH_3)_2$ | $[\alpha]_D^{24}-39.6°$ (c 1.0,CHCl$_3$) | 1.56 | 2.29 | 3.36 | 11-OMe 3.49 (s,3H) (CDCl$_3$) |
| 107 | $C_2H_5$ | H | $N(CH_3)_2$ | $[\alpha]_D^{24}-29.8°$ (c 1.0,CHCl$_3$) | 1.56 | 2.30 | 3.36 | (CDCl$_3$) |
| 108 | $COC_2H_5$ | $COCH_3$ | $N(CH_3)_2$ | $[\alpha]_D^{24}-20.2°$ (c 1.0,CHCl$_3$) | 1.61 | 2.33 | 3.34 | 12-OAc 2.03 (s,3H) (CDCl$_3$) |
| 109 | $COC_3H_7$ | $COCH_3$ | $N(CH_3)_2$ | $[\alpha]_D^{24}-18.2°$ (c 1.0,CHCl$_3$) | 1.58 | 2.29 | 3.32 | 12-OAc 2.00 (s,3H) (CDCl$_3$) |
| 110 | $COCH_3$ | $COCH_3$ | $\begin{array}{c} CH_3 \\ / \\ N^{\oplus}-C_2H_5.Br^{\ominus} \\ \backslash \\ CH_3 \end{array}$ | $[\alpha]_D^{22}-26.4°$ (c 1.0,CH$_3$OH) | 1.60 | 3.17 | 3.38 | 11-OAc 2.01 (s,3H) 12-OAc 2.05 (CD$_3$OD) |
| 111 | H | H | $\begin{array}{c} CH_3 \\ / \\ N^{\oplus}-CH_2COOCH_3.Br^{\ominus} \\ \backslash \\ CH_3 \end{array}$ | $[\alpha]_D^{22}-30.0°$ (c 1.0,CH$_3$OH) | 1.56 | 3.35 | 3.37 | (CD$_3$OD) |

TABLE 16-continued

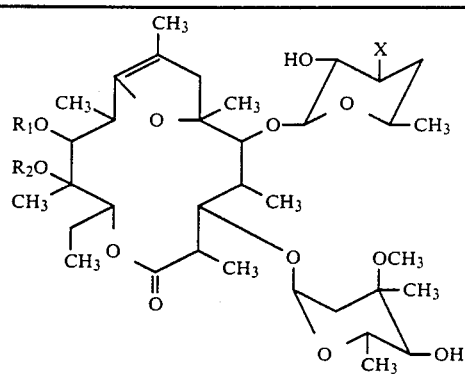

| Compound No. | R¹ | R² | X | Specific rotary power | NMR spectrum δ value ppm | | | |
|---|---|---|---|---|---|---|---|---|
| | | | | | 8-Me(s,3H) | 3'-NMe$_2$ (s,6H) | 3'-OMe(s,3H) | others (solvent) |
| 112 | H | H | $\underset{CH_3}{\overset{CH_3}{N^{\oplus}}}$—CH$_2$COOH.Br$^{\ominus}$ | $[\alpha]_D^{22}$ −31.8° (c 1.0,CH$_3$OH) | 1.58 | 3.38 | 3.38 | (CD$_3$OD) |
| 113 | H | H | $\underset{CH_3}{\overset{CH_3}{N^{\oplus}}}$—CH$_2$CH$_2$F.Br$^{\ominus}$ | $[\alpha]_D^{22}$ −26.0° (c 1.0,CH$_3$OH) | 1.59 | 3.35 | 3.38 | (CD$_3$OD) |
| 114 | H | H | $\underset{CH_3}{\overset{CH_3}{N^{\oplus}}}$—CH$_2$CN.Br$^{\ominus}$ | $[\alpha]_D^{22}$ −40.4° (c 1.0,CH$_3$OH) | 1.58 | 3.35 | 3.38 | (CD$_3$OD) |

REFERENCE EXAMPLE 105

By using 200 mg of 9-dihydroerythromycin A 6,9-epoxide (compound 84) (reference : Japanese Laid-open Patent Publication No. 1588/1972) and 0.5 ml of allyl bromide, the same processing as in Reference Example 50 was conducted to obtain 190 mg of 9-dihydroerythromycin A 6,9-epoxide allyl bromide (compound 115 in white powder.

REFERENCE EXAMPLE 106

By using 200 mg of 9-dihydroerythromycin A 6,9-epoxide (compound 84) and 0.5 ml of propargyl bromide, the same processing as in Reference Example 50 was conducted to obtain 195 mg (yield 84%) of 9-dihydroerythromycin A 6,9-epoxide propargyl bromide (compound 116) in white powder.

The structural formulae, specific rotatory powers and NMR spectrum values of the compounds obtained in Reference Examples 105 and 106 are shown in Table 17.

TABLE 17

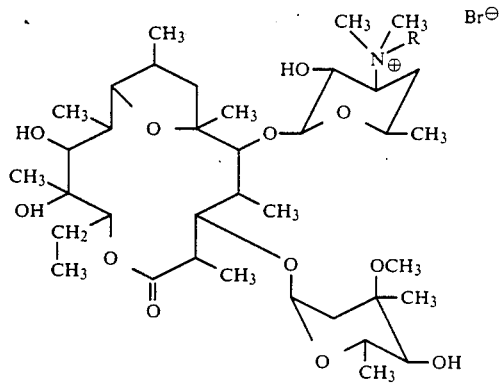

| Compound No. | R | $[\alpha]_D^{22}$(c 1.0, CH$_3$OH) | NMR spectrum δ value ppm (CD$_3$OD) | |
|---|---|---|---|---|
| | | | 3'-NMe(s,6H) | 3''-OMe(s,3H) |
| 115 | CH$_2$CH=CH$_2$ | −38.4° | 3.16 | 3.36 |
| 116 | CH$_2$C≡CH | −41.2° | 3.20 | 3.37 |

REFERENCE EXAMPLE 107

505 mg of the compound 75 was dissolved in 5 ml of methanol, then 121 mg of sodium hydrogen carbonate and 68.5 μl of allyl bromide were added thereto, and the mixture was stirred at 50° C. for two hours. This reaction mixture was diluted with 35 ml of ethyl acetate, and the solution was washed with a saturated aqueous sodium hydrogen carbonate and a saturated aqueous sodium chloride solution. The ethyl acetate solution was dried over anhydrous sodium sulfate and the solvent was evaporated under reduced pressure. The residue was purified by silica gel column chromatography (eluant: chloroform- methanol-conc. aqueous ammonia (10:1:0.1)) to obtain 72 mg (yield 67%) of allyl-nor-8,9-anhydroerythromycin A 6,9-hemiketal (compound 117) in white powder.

REFERENCE EXAMPLE 108

By using 105 mg of the compound 75, 25 mg of sodium hydrogen carbonate and 14.7 μl of propargyl bromide, the same processing as in Reference Example 107 was conducted to obtain 66 mg (yield 60%) of propargyl-nor-8,9-anhydroerythromycin A 6,9-hemiketal (compound 118) in white powder.

REFERENCE EXAMPLE 109

105 mg of the compound 75 was dispersed in 1 ml of methanol, then 0.29 ml of diisopropylethylamine and 0.29 ml of 1-iodopropane were added thereto, and the mixture was stirred at 50° C. for 22 hours. This reaction mixture was diluted with 20 ml of ethyl acetate, and the solution was washed with a saturated aqueous sodium hydrogen carbonate and a saturated aqueous sodium chloride solution. The ethyl acetate solution was dried over anhydrous sodium sulfate and the solvent was evaporated under reduced pressure. The residue was purified by silica gel column chromatography (eluant: chloroform-methanol-conc. aqueous ammonia (50:1:0.1)) to obtain 84 mg (yield 75%) of propyl-nor-8,9-anhydroerythromycin A 6,9-hemiketal (compound 119) in white powder.

REFERENCE EXAMPLE 110

By using 105 mg of the compound 75, 0.26 ml of diisopropylethylamine and 0.21 ml of bromoethanol, the same processing as in Reference Example 109 was conducted to obtain 94 mg (yield 84%) of 2-hydroxyethyl-nor-8,9-anhydroerythromycin A 6,9-hemiketal (compound 120) in white powder.

REFERENCE EXAMPLE 111

By using 351 mg of the compound 75, 0.87 ml of diisopropylethylamine and 2 ml of 2-iodopropane, the same processing as in Reference Example 109 was conducted to obtain 101 mg (yield 27%) of isopropyl-nor-8,9-anhydroerythromycin A 6,9-hemiketal (compound 121) in white powder.

REFERENCE EXAMPLE 112

By using 351 mg of the compound 75, 0.87 ml of diisopropylethylamine and 2.2 ml of isobutyl bromide, the same processing as in Reference Example 109 was conducted to obtain 52 mg (yield 14%) of isobutyl-nor-8,9-anhydroerythromycin A 6,9-hemiketal (compound 122) in white powder.

REFERENCE EXAMPLE 113

1.0 g of the compound 76 was dispersed in 10 ml of methanol, to this 2.5 ml of diisopropylethylamine and 1.3 ml of allyl bromide were added, and the mixture was stirred at 50° C. for 40 minutes. The solvent was removed under reduced pressure, and the residue was purified by silica gel column chromatography (eluant: chloroform- methanol-conc. aqueous ammonia (50:1:0.1)) to obtain 337 mg (yield 30%) of diallyl-dinor-8,9-anhydroerythromycin A 6,9-hemiketal (compound 123) in white powder and 256 mg (yield 24%) of allyl-dinor-8,9-anhydroerythromycin A 6,9-hemiketal (compound 124) in white powder.

REFERENCE EXAMPLE 114

500 mg of the compound 76 was dispersed in 5 ml of methanol, to this were added 0.64 ml of diisopropylethylamine and 0.33 ml of propargyl bromide, and the mixture was stirred at 50° C. for 1 hour. The solvent was removed under reduced pressure, and the residue was purified by silica gel column chromatography (eluant: chloroform-methanol-conc. aqueous ammonia (100:1:0.1)) to obtain 114 mg (yield 21%) of dipropargyl-dinor-8,9-anhydroerythromycin A 6,9-hemiketal (compound 125) in white powder and 252 mg (yield 45%) of propargyl-dinor-8,9- anhydroerythromycin A 6,9-hemiketal (compound 126) in white powder.

REFERENCE EXAMPLE 115

By using 256 mg of the compound 124, 0.61 ml of diisopropylethylamine and 0.31 ml of propargyl bromide, the same processing as in Reference Example 109 was conducted to obtain 207 mg (yield 77%) of N-allyl-N-propargyl-dinor-8,9-anhydroerythromycin A 6,9-hemiketal (compound 127) in white powder.

REFERENCE EXAMPLE 116

By using 100 mg of the compound 117 and 0.1 ml of allyl bromide, the same processing as in Reference Example 50 was conducted to obtain 110 mg (yield 94%) of allyl-nor-8,9- anhydroerythromycin A 6,9-hemiketal allyl bromide (compound 128) in white powder.

REFERENCE EXAMPLE 117

By using 100 mg of the compound 117 and 0.1 ml of propargyl bromide, the same processing as in Reference Example 50 was conducted to obtain 102 mg (yield 85%) of allyl-nor-8,9-anhydroerythromycin A 6,9-hemiketal propargyl bromide (compound 129) in white powder.

REFERENCE EXAMPLE 118

By using 61 mg of the compound 118 and 0.1 ml of propargyl bromide, the same processing as in Reference Example 50 was conducted to obtain 51 mg (yield 72%) of propargyl-nor-8,9-anhydroerythromycin A 6,9-hemiketal propargyl bromide (compound 130) in white powder.

REFERENCE EXAMPLE 119

By using 99 mg of the compound 123 and 0.1 ml of allyl bromide, the same processing as in Reference Example 50 was conducted to obtain 16 mg (yield 14%) of diallyl-dinor-8,9-anhydroerythromycin A 6,9-hemiketal allyl bromide (compound 131) in white powder.

REFERENCE EXAMPLE 120

61 mg of the compound 123 was dissolved 1 ml of methanol, then 12 mg of sodium hydrogen carbonate and 81.9 μl of propargyl bromide were added thereto, and the mixture thereof was stirred at room temperature for 3 days. The same processing as in Reference Example 50 was hereinafter conducted to obtain 32 mg (yield 39%) of diallyl-dinor-8,9-anhydroerythromycin A 6,9-hemiketal propargyl bromide (compound 132) in white powder.

REFERENCE EXAMPLE 121

By using 101 mg of the compound 126, 24 mg of sodium hydrogen carbonate and 0.1 ml of propargyl bromide, the same processing as in Reference Example 120 was conducted to obtain 38 mg (yield 30%) of dipropargyl-dinor-8,9-anhydroerythromycin A 6,9-hemiketal propargyl bromide (compound 133) in white powder.

REFERENCE EXAMPLE 122

By using 50 mg of the compound 121, and 0.1 ml of iodomethane, the same processing as in Reference Example 50 was conducted to obtain 52 mg (yield 86%) of 8,9-anhydroerythromycin A 6,9-hemiketal isopropyl iodide (compound 134) in white powder.

REFERENCE EXAMPLE 123

By using 29 mg of the compound 122, and 0.4 ml of iodomethane, the same processing as in Reference Example 50 was conducted to obtain 30 mg (yield 86%) of 8,9-anhydroerythromycin A 6,9-hemiketal isopropyl iodide (compound 135) in white powder.

REFERENCE EXAMPLE 124

150 mg of the compound 27 was dissolved in 3 ml of chloroform, then 1 ml of butyl iodide was added thereto and the mixture was heated under reflux for 3 days. The same processing as in Reference Example 50 was hereinafter conducted to obtain 121 mg (yield 64%) of 8,9-anhydroerythromycin A 6,9 hemiketal butyl iodide (compound 136) in white powder.

REFERENCE EXAMPLE 125

150 mg of the compound 27 was dissolved in 2 ml of chloroform, then 0.3 ml of cyclopropylmethyl bromide was added thereto and the mixture was heated under reflux for 2 days. The same processing as in Reference Example 50 was hereinafter conducted to obtain 145 mg (yield 81%) of 8,9-anhydroerythromycin A 6,9 hemiketal cyclopropyl-methyl bromide (compound 137) in white powder.

REFERENCE EXAMPLE 126

150 mg of the compound 27 was dissolved in 2 ml of chloroform, then 0.5 ml of crotyl bromide was added thereto and the mixture was allowed to stand at room temperature for 6 hours. The same processing as in Reference Example 50 was hereinafter conducted to obtain 175 mg (yield 98%) of 8,9-anhydroerythromycin A 6,9-hemiketal crotyl bromide (compound 138) in white powder.

REFERENCE EXAMPLE 127

150 mg of the compound 27 was dissolved in 1.5 ml of chloroform, then 0.5 ml of 2,3-dibromopropene was added thereto and the mixture was allowed to stand at room temperature for 1 day. The same processing as in Reference Example 50 was hereinafter conducted to obtain 111 mg (yield 58%) of 8,9-anhydroerythromycin A 6,9-hemiketal 2-bromoallyl bromide (compound 139) in white powder.

REFERENCE EXAMPLE 128

150 mg of the compound 27 was dissolved in 3 ml of chloroform, then 0.5 ml of propargyl chloride was added thereto and the mixture thereof was heated under reflux for 1 day. The same processing as in Reference Example 50 was conducted to obtain 156 mg (yield 94%) of 8,9-anhydroerythromycin A 6,9-hemiketal propargyl chloride (compound 140) in white powder.

The structural formulae, specific rotatory powers and NMR spectrum values of the compounds obtained in Reference Examples 108-129 are shown in Table 18.

TABLE 18

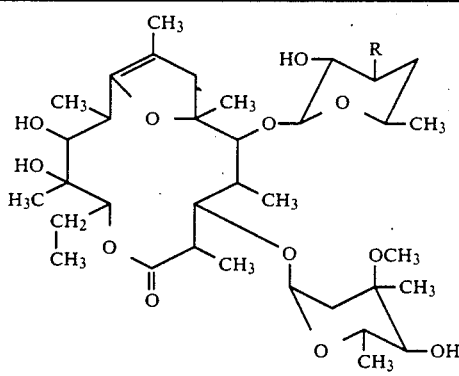

| Compound No. | R | $[\alpha]_D^{24}$(c 1.0) | 8-Me(s,3H) | 3''-OMe(s,3H) | Others (solvent) |
|---|---|---|---|---|---|
| 117 | N(CH₃)(CH₂CH=CH₂) | −40.2° (CHCl₃) | 1.56 | 3.33 | 2.19 (3'-NMe,s,3H) (CDCl₃) |

TABLE 18-continued

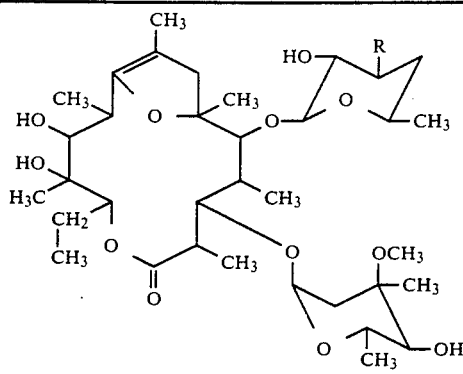

| Compound No. | R | $[\alpha]_D^{24}$(c 1.0) | NMR spectrum δ value ppm | | |
|---|---|---|---|---|---|
| | | | 8-Me(s,3H) | 3''-OMe(s,3H) | Others (solvent) |
| 118 | N(CH₃)(CH₂C≡CH) | −40.2° (CHCl₃) | 1.57 | 3.36 | 2.35 (3'-NMe,s,3H) (CDCl₃) |
| 119 | N(CH₃)(CH₂CH₂CH₃) | −36.2° (CHCl₃) | 1.57 | 3.36 | 2.23 (3'-NMe,s,3H) (CDCl₃) |
| 120 | N(CH₃)(CH₂CH₂OH) | −32.4° (CHCl₃) | 1.57 | 3.35 | 2.34 (3'-NMe,s,3H) (CDCl₃) |
| 121 | N(CH₃)(CH₂(CH₃)₂) | −36.8° (CHCl₃) | 1.56 | 3.36 | 2.21 (3'-NMe,s,3H) (CDCl₃) |
| 122 | N(CH₃)(CH₂CH(CH₃)₂) | −36.6° (CHCl₃) | 1.57 | 3.36 | 2.22 (3'-NMe,s,3H) (CDCl₃) |
| 123 | N—(CH₂CH=CH₂)₂ | −39.6° (CHCl₃) | 1.56 | 3.32 | (CDCl₃) |
| 124 | N(H)(CH₂CH=CH₂) | −31.4° (CHCl₃) | 1.57 | 3.35 | (CDCl₃) |
| 125 | N—(CH₂C≡CH)₂ | −28.4° (CHCl₃) | 1.57 | 3.36 | (CDCl₃) |
| 126 | N(H)(CH₂C≡CH) | −32.2° (CHCl₃) | 1.57 | 3.36 | (CDCl₃) |
| 127 | N(CH₂CH=CH₂)(CH₂C≡CH) | −31.2° (CHCl₃) | 1.57 | 3.36 | (CDCl₃) |
| 128 | ⊕N(CH₃)(CH₂CH=CH₂)₂ Br⊖ | −24.4° (CH₃OH) | 1.59 | 3.36 | 3.07 (3'-NMe,s,3H) (CD₃OD) |
| 129 | ⊕N(CH₃)(CH₂CH=CH₂)(CH₂C≡CH) Br⊖ | −23.8° (CH₃OH) | 1.59 | 3.39 | 3.17 (3'-NMe,s,3H) (CD₃OD) |

TABLE 18-continued

[Structure of macrolide compound with R group substituent]

| Compound No. | R | $[\alpha]_D^{24}$(c 1.0) | NMR spectrum δ value ppm 8-Me(s,3H) | 3''-OMe(s,3H) | Others (solvent) |
|---|---|---|---|---|---|
| 130 | ⊕N(CH₃)(CH₂C≡CH)₂ Br⊖ | −20.5° (CH₃OH) | 1.59 | 3.40 | 3.29 (3'-NMe,s,3H) (CD₃OD) |
| 131 | ⊕N—(CH₂CH=CH₂)₃Br⊖ | −13.3° (CH₃OH) | 1.58 | 3.34 | (CD₃OD) |
| 132 | ⊕N(CH₂C≡CH)(CH₂CH=CH₂)₂ Br⊖ | −18.0° (CH₃OH) | 1.59 | 3.36 | (CD₃OD) |
| 133 | ⊕N—(CH₂C≡CH)₃Br⊖ | −18.4° (CH₃OH) | 1.58 | 3.39 | (CD₃OD) |
| 134 | ⊕N(CH₃)₂CH(CH₃)₂ I⊖ | −26.4° (CH₃OH) | 1.58 | 3.36 | 2.90 (3'-NMe₂,s,6H) (CD₃OD) |
| 135 | ⊕N(CH₃)₂CH₂CH(CH₃)₂ I⊖ | −26.0° (CH₃OH) | 1.59 | 3.38 | 3.19 (3'-NMe₂,s,6H) (CD₃OD) |
| 136 | ⊕N(CH₃)₂CH₂CH₂CH₂CH₃ I⊖ | −29.4° (CH₃OH) | 1.59 | 3.39 | 3.22 (3'-NMe₂,s,6H) (CD₃OD) |
| 137 | ⊕N(CH₃)₂CH₂-cyclopropyl Br⊖ | −24.4° (CH₃OH) | 1.58 | 3.37 | 3.24 (3'-NMe₂,s,6H) (CD₃OD) |
| 138 | ⊕N(CH₃)₂CH₂CH=CHCH₃ Br⊖ | −29.6° (CH₃OH) | 1.58 | 3.38 | 3.13 (3'-NMe₂,s,6H) (CD₃OD) |
| 139 | ⊕N(CH₃)₂CH₂CBr=CH₂ Br⊖ | −26.2° (CH₃OH) | 1.58 | 3.34 | 3.34 (3'-NMe₂,s,6H) (CD₃OD) |
| 140 | ⊕N(CH₃)₂CH₂C≡CH Cl⊖ | −27.8° (CH₃OH) | 1.58 | 3.39 | 3.26 (3'-NMe₂,s,6H) (CD₃OD) |

REFERENCE EXAMPLE 129

73.5 mg of the compound 32 was dissolved in 0.8 ml of methanol, and 0.2 ml of water was added thereto, followed by addition of 66.4 mg of CH₃COONa·3H₂O. The reaction mixture was heated at 50° C., and stirred after 26 mg of iodine was added thereto. In order to maintain the pH of the reaction mixture at 8 to 9, 0.4 ml portions of 1N aqueous sodium hydroxide solution were added thereto after 10 minutes, 30 minutes and 1 hour, respectively, and the stirring was further continued for 1 hour. The solution was thereafter poured into 100 ml of dilute aqueous ammonia and the resultant product was extracted with chloroform. The extract was washed with dilute aqueous ammonia and dried with anhydrous sodium sulfate. Thereafter, the solvent was distilled off under reduced pressure. The residue was purified by silica gel column chromatography [eluant: chloroform-methanol-conc. aqueous ammonia (15:1:0.1)] to obtain 51 mg (yield 70%) of 11,12-di-0-acetyl-de-N-methyl-8,9- anhydroerythromycin A 6,9-hemiketal (compound 141) in white powder.

REFERENCE EXAMPLE 130

By using 79 mg of the compound 141, 0.17 ml of diisopropylethylamine and 0.16 ml of iodomethane, the same processing as in Reference Example 109 was conducted to obtain 30 mg (yield 37%) of 11,12-di-0-acetyl-N-ethyl-nor-8,9-anhydroerythromycin A 6,9-hemiketal (compound 142) in white powder.

REFERENCE EXAMPLE 131

By using 500 mg of the compound 20, 468 mg of $CH_3COONa \cdot 3H_2O$ and 170 mg of iodine, the same processing as in Reference Example 129 was conducted to obtain 413 mg (yield 84%) of de-N-methyl-8,9-anhydroerythromycin A 6,9-hemiketal cyclic 11,12-carbonate (compound 143) in white powder.

REFERENCE EXAMPLE 132

By using 350 mg of the compound 143, 0.84 ml of diisopropylethylamine and 0.77 ml of iodoethane, the same processing as in Reference Example 109 was conducted to obtain 254 mg (yield 69%) of N-ethyl-nor-8,9-anhydroerythromycin A 6,9-hemiketal cyclic 11,12 carbonate(compound 144) in white powder.

REFERENCE EXAMPLE 133

By using 24.8 mg of 8,9-anhydroerythromycin B 6,9-hemiketal (reference: P. Kurath, et al., Experientia, 27, 362,1971) and 0.2 ml of bromoethane, the same processing as in Reference Example 100 was conducted to obtain 20 mg (yield 69%) of 8,9-anhydroerythromycin B 6,9-hemiketal ethyl bromide (compound 145) in white powder.

REFERENCE EXAMPLE 134

By using 24.7 mg of 8,9-anhydroerythromycin B 6,9-hemiketal and 0.05 ml of propargyl bromide, the same processing as in Reference Example 50 was conducted to obtain 24 mg (yield 83%) of 8,9-anhydroerythromycin B 6,9-hemiketal propargyl bromide (compound 146) in white powder.

REFERENCE EXAMPLE 135

By using 50 mg of the compound 54 and 0.3 ml of propargyl bromide, the same processing as in Reference Example 50 was conducted to obtain 54 mg (yield 93%) of 11,12-0-isopropylidene-8,9-anhydroerythromycin A 6,9-hemiketal propargyl bromide (compound 147) in white powder.

REFERENCE EXAMPLE 136

By using 50 mg of the compound 39 and 0.3 ml of propargyl bromide, the same processing as in Reference Example 50 was conducted to obtain 55 mg (yield 96%) of 8,9-anhydroerythromycin A 6,9-hemiketal 11,12-phenylboronate propargyl bromide (compound 148) in white powder.

REFERENCE EXAMPLE 137

By using 100 mg of the compound 20 and 0.3 ml of propargyl bromide, the same processing as in Reference Example 50 was conducted to obtain 108 mg (yield 93%) of 8,9-anhydroerythromycin A 6,9-hemiketal 11,12-cyclic-carbonate propargyl bromide (compound 149) in white powder.

REFERENCE EXAMPLE 138

By using 100 mg of the compound 37 and 0.3 ml of propargyl bromide, the same processing as in Reference Example 50 was conducted to obtain 107 mg (yield 93%) of 8,9-anhydroerythromycin A 6,9-hemiketal 11,12-sulfite propargyl bromide (compound 150) in white powder.

REFERENCE EXAMPLE 139

100 mg of the compound 8 was dissolved in 2 ml of dry dimethyl sulfoxide, and to this, were added 1 ml of acetic anhydride and 0.3 ml of aceticacid. The reaction mixture was allowed to stand for 1 day at room temperature. Thereafter, the same processing as in Reference Example 39 was conducted to obtain 65 mg (yield 56%) of 2'-0-acetyl-4''-0-formyl-11,12-di-0-methylthiomethyl-8,9-anhydroerythromycin A 6,9-hemiketal (compound 151) in white powder.

REFERENCE EXAMPLE 140

150 mg of the compound 151 was dissolved in 6 ml of methanol, and to this, was added 1 ml of conc. aqueous ammonia. The reaction mixture was heated, for 2 days under reflux. Thereafter, the same processing as in Reference Example 40 was conducted to obtain 105 mg (yield 76%) of 11,12-di-0-methylthiomethyl-8,9-anhydroerythromycin A 6,9-hemiketal (compound 152) in white powder.

REFERENCE EXAMPLE 141

By using 100 mg of the compound 152 and 0.2 ml of propargyl bromide, the same processing as in Reference Example 50 was conducted to obtain 98 mg (yield 86%) of 11,12-di-0-methylthiomethyl-8,9-anhydroerythromycin A 6,9-hemiketal propargyl bromide (compound 153) in white powder.

REFERENCE EXAMPLE 142

99 mg of the compound 1 was dissolved in 3 ml of chloroform, then 0.5 ml of propargyl bromide was added thereto and the mixture was allowed to stand at room temperature for 3 hours. The same processing as in Reference Example 50 was hereinafter conducted to obtain 76 mg (yield 66%) of 2'-0-acetyl-8,9-anhydroerythromycin A 6,9-hemiketal (compound 154) in white powder.

The structural formulae, specific rotatory powers and NMR spectrum values of the compounds obtained in Reference Examples 129–142 are shown in Table 19.

TABLE 19(a)

| No. | R¹ | R² | R³ | R⁴ | X | $[\alpha]_D^{24}$ (c 1.0) |
|---|---|---|---|---|---|---|
| 141 | H | H | OAc | OAc | N(H)(CH₃) | −17.0° (CHCl₃) |
| 142 | H | H | OAc | OAc | N(CH₃)(C₂H₅) | −11.8° (CHCl₃) |
| 143 | H | H | —O—C(=O)—O— (R³,R⁴ cyclic carbonate) | | N(H)(CH₃) | −30.0° (CHCl₃) |
| 144 | H | H | —O—C(=O)—O— (R³,R⁴ cyclic carbonate) | | N(CH₃)(C₂H₅) | −30.8° (CHCl₃) |
| 145 | H | H | OH | H | ⊕N(CH₃)(CH₃)(C₂H₅) Br⊖ | −18.8° (CH₃OH) |
| 146 | H | H | OH | H | ⊕N(CH₃)(CH₃)(CH₂C≡CH) Br⊖ | −23.6° (CH₃OH) |
| 147 | H | H | —O—C(CH₃)(CH₃)—O— | | ⊕N(CH₃)(CH₃)(CH₂C≡CH) Br⊖ | −23.2° (CH₃OH) |
| 148 | H | H | —O—B(Ph)—O— | | ⊕N(CH₃)(CH₃)(CH₂C≡CH) Br⊖ | −55.4° (CH₃OH) |
| 149 | H | H | —O—C(=O)—O— | | ⊕N(CH₃)(CH₃)(CH₂C≡CH) Br⊖ | −29.6° (CH₃OH) |
| 150 | H | H | —O—S(=O)—O— | | ⊕N(CH₃)(CH₃)(CH₂C≡CH) Br⊖ | −31.4° C. (CH₃OH) |
| 151 | Ac | CHO | OCH₂SCH₃ | OCH₂SCH₃ | N(CH₃)₂ | −37.2° (CHCl₃) |
| 152 | H | H | OCH₂SCH₃ | OCH₂SCH₃ | N(CH₃)₂ | −34.6° (CHCl₃) |

TABLE 19(a)-continued

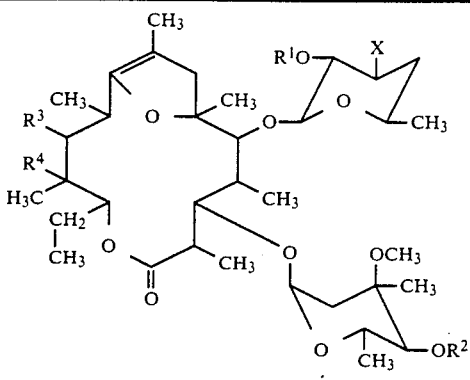

| No. | R¹ | R² | R³ | R⁴ | X | $[\alpha]_D^{24}$(c 1.0) |
|---|---|---|---|---|---|---|
| 153 | H | H | OCH₂SCH₃ | OCH₂SCH₃ | ⊕N(CH₃)(CH₃)(CH₂C≡CH) Br⊖ | −32.2° (CH₃OH) |
| 154 | Ac | H | OH | OH | ⊕N(CH₃)(CH₃)(CH₂C≡CH) Br⊖ | −41.2° (CH₃OH) |

TABLE 19(b)

| Compound No. | 8-Me (s, 3H) | 3″-OMe (s, 3H) | Others (solvent) |
|---|---|---|---|
| 141 | 1.59 | 3.34 | 1.99 (OAc, s, 3H), 2.03 (OAc, s, 3H) 2.42 (3′-NMe, s, 3H) (CDCl₃) |
| 142 | 1.60 | 3.34 | 1.99 (OAc, s, 3H), 2.03 (OAc, s, 3H) 2.23 (3′-NMe, s, 3H) (CDCl₃) |
| 143 | 1.62 | 3.35 | 2.42 (3′-NMe, s, 3H) (CDCl₃) |
| 144 | 1.61 | 3.35 | 2.23 (3′-NMe, s, 3H) (CDCl₃) |
| 145 | 1.58 | 3.38 | 3.14 (3′-NMe₂, s, 6H) (CD₃OD) |
| 146 | 1.58 | 3.39 | 3.25 (3′-NMe₂, s, 6H) (CD₃OD) |
| 147 | 1.62 | 3.39 | 1.38 (C(CH₃)(CH₃), s, 6H) (CD₃OD) 3.27 (3′-NMe₂, s, 6H) |
| 148 | 1.62 | 3.39 | 3.28 (3′-NMe₂, s, 6H) (CD₃OD) 7.3–7.8 (ph, m, 5H) |
| 149 | 1.61 | 3.53 | 3.37 (3′-NMe₂, s, 6H) (CDCl₃) |
| 150 | 1.57 | 3.39 | 3.39 (3′-NMe₂, s, 6H) (CD₃OD) |
| 151 | 1.58 | 3.36 | 2.04 (2′-OAc, s, 3H), (CDCl₃) 2.27 (3′-NMe₂, s, 6H), 8.19 (4″-CHO, s, 1H) |
| 152 | 1.58 | 3.35 | 2.22 (11-SCH₃, s, 3H), (CDCl₃) 2.24 (12-SCH₃, s, 3H), 2.29 (3′-NMe₂, s, 6H) |
| 153 | 1.58 | 3.39 | 2.22 (SCH₃, s, 6H), (CD₃OD) 3.25 (3′-NMe₂, s, 6H) |
| 154 | 1.56 | 3.38 | 2.20 (2′-OAc, s, 3H), (CD₃OD) 3.32 (3′-NMe₂, s, 6H) |

REFERENCE EXAMPLE 143

150 mg of the compound 84 was dissolved in 3 ml of chloroform, then 0.5 ml of propargyl chloride was added thereto and the mixture was heated under reflux for 1 day. Thereafter, the same processing as in Reference Example 50 was conducted to obtain 142 mg (yield 86%) of 9-dihidroerythromycin A 6,9-epoxide propargyl chloride(compound 155) in white powder.

REFERENCE EXAMPLE 144

By using 143 mg of the compound 84, 27 ml of acetic anhydride and 31 μl of pyridine, the same processing as in Reference Example 23 was conducted to obtain 125 mg (yield 83%) of 2′-acetyl-9-dihydroerythromycin A 6,9-epoxide (compound 156) in white powder.

REFERENCE EXAMPLE 145

150 mg of the compound 84 was dissolved in 3 ml of chloroform, then 0.5 ml of benzyl chloride was added thereto and the mixture was heated under reflux for 38 hours. Thereafter, the same processing as in Reference Example 50 was conducted to obtain 155 mg (yield 81%) of 9-dihidroerythromycin A 6,9-epoxide benzyl chloride (compound 157) in white powder.

REFERENCE EXAMPLE 146

150 mg of the compound 84 was dissolved in 3 ml of chloroform, then 0.5 ml of 1-bromo-2-fluoroethane was added thereto and the mixture was heated under reflux for 7 days. Thereafter, the same processing as in Reference Example 50 was conducted to obtain 66 mg (yield 37%) of 9-dihydroerythromycin A 6,9-epoxide 2-fluoroethyl bromide (compound 158) in pale yellow powder.

REFERENCE EXAMPLE 147

150 mg of the compound 84 was dissolved in 3 ml of chloroform, then 0.5 ml of cyclopropylmethyl bromide was added thereto and the mixture was heated under reflux for 38 hours. Thereafter, the same processing as in Reference Example 50 was conducted to obtain 153 mg (yield 86%) of 9-dihidroerythromycin A 6,9-epoxide cyclopropylmethyl bromide (compound 159) in white powder.

REFERENCE EXAMPLE 148

150 mg of the compound 84 was dissolved in 3 ml of chloroform, then 0.5 ml of 3-butenyl bromide was added thereto and the mixture was heated under reflux for 38 hours. Thereafter, the same processing as in Reference Example 50 was conducted to obtain 113 mg (yield 63%) of 9-dihidroerythromycin A 6,9-epoxide 3-butenyl bromide (compound 160) in white powder.

REFERENCE EXAMPLE 149

125 mg of the compound 156 was dissolved in 3 ml of chloroform, then 0.5 ml of propargyl bromide was added thereto and the mixture was allowed to stand at room temperature for 3 hours. Thereafter, the same processing as in Reference Example 50 was conducted to obtain 114 mg (yield 79%) of 2'-0-acetyl-9-dihidroerythromycin A 6,9-epoxide propargyl bromide (compound 161) in white powder.

The structural formulae, specific rotatory powers and NMR spectrum values of the compounds obtained in Reference Examples 143-149 are shown in Table 20.

and 0.1 ml of propargyl bromide, the same processing as in Reference Example 50 was conducted to obtain 73 mg (yield 98%) of 6-0-methylerythromycin A propargyl bromide (compound 162) in white powder.

REFERENCE EXAMPLE 151

200 mg of erythromycin A was dissolved in 3 ml of chloroform, then 0.3 ml of ethyl iodide was added thereto and the mixture was heated under reflux for 20 hours. Thereafter, the same processing as in Reference Example 54 was conducted to obtain 150 mg (yield 62%) of erythromycin A ethyl iodide (compound 163) in pale yellow powder.

REFERENCE EXAMPLE 152

100 mg of erythromycin A was dissolved in 2 ml of chloroform, then 0.2 ml of allyl bromide was added

TABLE 20

[Structural formula of erythromycin derivative with RO and X substituents]

| Compound No. | R | X | $[\alpha]_D^{24}$ (c 1.0, CH$_3$OH) | NMR spectrum δ value ppm (CD$_3$OD) | | |
|---|---|---|---|---|---|---|
| | | | | 3'-NMe$_2$ (s, 6H) | 3''-OMe (s, 3H) | Others |
| 155 | H | $\oplus$N(CH$_3$)$_2$CH$_2$C≡CH  Cl$^\ominus$ | −44.4° | 3.20 | 3.37 | |
| 156 | Ac | N(CH$_3$)$_2$ | −53.6° | 2.28 | 3.35 | 2.07 (2'-OAc, s, 3H) (CDCl$_3$) |
| 157 | H | $\oplus$N(CH$_3$)$_2$CH$_2$Ph  Cl$^\ominus$ | −47.4° | 3.12 | 3.33 | |
| 158 | H | $\oplus$N(CH$_3$)$_2$CH$_2$CH$_2$F  Br$^\ominus$ | −38.4° | 3.25 | 3.36 | |
| 159 | H | $\oplus$N(CH$_3$)$_2$CH$_2$-cyclopropyl  Br$^\ominus$ | −37.0° | 3.23 | 3.36 | |
| 160 | H | $\oplus$N(CH$_3$)$_2$CH$_2$CH$_2$CH=CH$_2$  Br$^\ominus$ | −37.6° | 3.13 | 3.37 | |
| 161 | Ac | $\oplus$N(CH$_3$)$_2$CH$_2$C≡CH  Br$^\ominus$ | −52.0° | 3.23 | 3.36 | 2.21 (2'-OAc, s, 3H) |

REFERENCE EXAMPLE 150

By using 64 mg of 6-0-methylerythromycin A (reference: S. Morimoto, et al., J. Antibiotics, 37, 187, 1984)

thereto and the mixture was stirred at room temperature for 5 hours. Thereafter, the same processing as in Reference Example 50 was conducted to obtain 97 mg (yield 83%) of erythromycin A allyl bromide (compound 164) in white powder.

REFERENCE EXAMPLE 153

200 mg of erythromycin A was dissolved in 3 ml of chloroform, then 0.2 ml of propargyl bromide was added thereto and the mixture was stirred at room temperature for 3 hours. Thereafter, the same processing as in Reference Example 54 was conducted to obtain 202 mg (yield 87%) of erythromycin A propargyl bromide (compound 165) in white powder.

The structural formulae, specific rotatory powers and NMR spectrum values of the compounds obtained in Reference Examples 150–153 are shown in Table 21.

REFERENCE EXAMPLE 157

50 mg of the compound 9 was dissolved in 1 ml of chloroform, 0.2 ml of propargyl bromide was added and the mixture was stirred at room temperature for 3 hours. Subsequently, the same processing as in Reference Example 50 was conducted to obtain 51 mg (yield 87%) of 4''-0-formyl-8,9-anhydroerythromycin A 6,9-hemiketal propargyl bromide (compound 169) in white powder.

REFERENCE EXAMPLE 158

50 mg of the compound 9 was dissolved in 1 ml of chloroform, then 0.2 ml of allyl bromide was added

TABLE 21

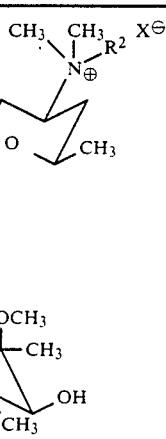

| Compound No. | $R_1$ | $R_2$ | X | $[\alpha]_D^{24}$ (c 1.0, $CH_3OH$) | NMR spectrum δ value ppm ($CD_3OD$) | | |
|---|---|---|---|---|---|---|---|
| | | | | | 3'-$NMe_2$ (s, 6H) | 3'''-OMe (s, 3H) | Others |
| 162 | $CH_3$ | $CH_2C\equiv CH$ | Br | −77.4° | 3.26 | 3.36 | 3.04 (6-OMe, s, 3H) |
| 163 | H | $C_2H_5$ | I | −43.6° | 3.20 | 3.35 | |
| 164 | H | $CH_2CH=CH$ | Br | −50.4° | 3.12 | 3.35 | |
| 165 | H | $CH_2C\equiv CH$ | Br | −54.6° | 3.27 | 3.36 | |

REFERENCE EXAMPLE 154

50 mg of the compound 9 was dissolved in 1 ml of chloroform, then 0.2 ml of methyl iodide was added thereto and the mixture was stirred at room temperature for 3 hours. Thereafter, the same processing as in Reference Example 50 was conducted to obtain 49 mg (yield 83%) of 4''-0-formyl-8,9-anhydroerythromycin A 6,9-hemiketal methyl iodide (compound 166) in pale yellow powder.

REFERENCE EXAMPLE 155

50 mg of the compound 9 was dissolved in 2 ml of chloroform, then 0.5 ml of ethyl iodide was added thereto and the mixture was heated under reflux for 20 hours. Subsequently, the same processing as in Reference Example 50 was conducted to obtain 38 mg (yield 13%) of 4''-0-formyl-8,9-anhydroerythromycin A 6,9-hemiketal ethyl iodide (compound 167) in pale yellow powder.

REFERENCE EXAMPLE 156

50 mg of the compound 9 was dissolved in 2 ml of chloroform, then 0.5 ml of propyl iodide was added thereto and the mixture was heated under reflux for 48 hours. Subsequently, the same processing as in Reference Example 50 was conducted to obtain 34 mg (yield 56%) of 4''-0-formyl-8,9-anhydroerythromycin A 6,9-hemiketal propyl iodide (compound 168) in pale yellow powder.

thereto and the mixture was stirred at room temperature for 5 hours. Subsequently, the same processing as in Reference Example 50 was conducted to obtain 47 mg (yield 80%) of 4''-0-formyl-8,9-anhydroerythro- mycin A 6,9-hemiketal allyl bromide (compound 170) in white powder.

REFERENCE EXAMPLE 159

50 mg of the compound 50 was processed in the same manner as in Reference Example 154 to obtain 50 mg (yield 84%) of 11-0-acetyl-8,9-anhydroerythromycin A 6,9-hemiketal methyl iodide (compound 171) in pale yellow powder.

REFERENCE EXAMPLE 160

50 mg of the compound 50 was processed in the same manner as in Reference Example 155 to obtain 39 mg (yield 65%) of 11-0-acetyl-8,9-anhydroerythromycin A 6,9-hemiketal ethyl iodide (compound 172) in pale yellow powder.

REFERENCE EXAMPLE 161

50 mg of the compound 50 was processed in the same manner as in Reference Example 156 to obtain 33 mg (yield 54%) of 11-0-acetyl-8,9-anhydroerythromycin A 6,9-hemiketal propyl iodide (compound 173) in pale yellow powder.

REFERENCE EXAMPLE 162

50 mg of the compound 50 was processed in the same manner as in Reference Example 157 to obtain 49 mg (yield 84%) of 11-0-acetyl-8,9-anhydroerythromycin A 6,9-hemiketal propargyl bromide (compound 174) in white powder.

REFERENCE EXAMPLE 163

50 mg of the compound 50 was processed in the same manner as in Reference Example 162 to obtain 46 mg (yield 79%) of 11-0-acetyl-8,9-anhydroerythromycin A 6,9-hemiketal allyl bromide (compound 175) in white powder.

REFERENCE EXAMPLE 164

50 mg of the compound 25 was dissolved in 1 ml of chloroform, then 0.2 ml of propargyl bromide was added thereto and the mixture was stirred at room temperature for 3 hours. Thereafter, the same processing as in Reference Example 50 was conducted to obtain 44 mg (yield 77%) of 4''-0-formyl-11-0-mesyl-8,9-anhydroerythromycin A 6,9-hemiketal propargyl bromide (compound 176) in white powder.

REFERENCE EXAMPLE 165

50 mg of the compound 57 was dissolved in 2 ml of chloroform, then 0.3 ml of ethyl iodide was added thereto and the mixture was heated under reflux for 20 hours. Subsequently, the same processing as in Reference Example 50 was conducted to obtain 39 mg (yield 66%) of 11-0-mesyl-8,9-anhydroerythromycin A 6,9-hemiketal ethyl iodide (compound 177) in pale yellow powder.

REFERENCE EXAMPLE 166

50 mg of the compound 57 was dissolved in 2 ml of chloroform, then 0.3 ml of propyl iodide was added thereto and the mixture was heated under reflux for 48 hours. Subsequently, the same processing as in Reference Example 54 was conducted to obtain 34 mg (yield 56%) of 11-0-mesyl-8,9-anhydroerythromycin A 6,9-hemiketal propyl iodide (compound 178) in pale yellow powder.

The structural formulae, specific rotatory powers and NMR spectrum values of the compounds obtained in Reference Examples 154–166 are shown in Table 22.

TABLE 22

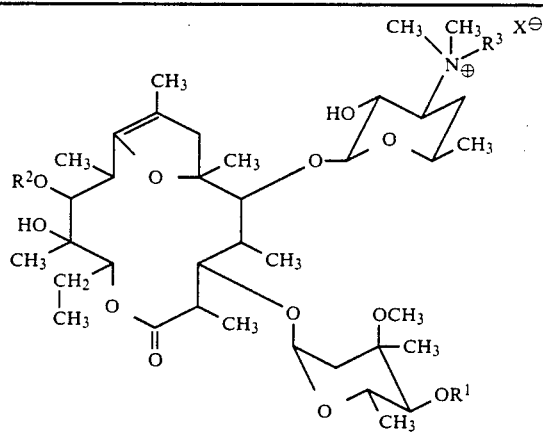

| Compound No. | $R_1$ | $R_2$ | $R_3$ | X | $[\alpha]_D^{24}$ (c 1.0, CH$_3$OH) | 8-CH$_3$ (s, 3H) | 3'-NMe$_2$ (s, 6H) | 3''-OMe (s, 3H) | Others |
|---|---|---|---|---|---|---|---|---|---|
| 166 | -CHO | H | CH$_3$ | I | −31.4° | 1.59 | 3.31 | 3.41 | 8.33 (4''-OCHO, s, 1H) |
| 167 | CHO | H | C$_2$H$_5$ | I | −31.8° | 1.59 | 3.19 | 3.41 | 8.31 (4''-OCHO, s, 1H) |
| 168 | CHO | H | C$_3$H$_7$ | I | −30.4° | 1.59 | 3.20 | 3.40 | 8.31 (4''-OCHO, s, 1H) |
| 169 | CHO | H | CH$_2$C≡CH | Br | −34.4° | 1.59 | 3.31 | 3.41 | 8.31 (4''-OCHO, s, 1H) |
| 170 | CHO | H | CH$_2$CH=CH$_2$ | Br | −32.8° | 1.59 | 3.18 | 3.38 | 8.29 (4''-OCHO, s, 1H) |
| 171 | H | COCH$_3$ | CH$_3$ | I | −12.0° | 1.60 | 3.29 | 3.38 | 2.11 (11-OAc, s, 3H) |
| 172 | H | COCH$_3$ | C$_2$H$_5$ | I | −10.0° | 1.60 | 3.15 | 3.38 | 2.10 (11-OAc, s, 3H) |
| 173 | H | COCH$_3$ | C$_3$H$_7$ | I | −13.4° | 1.60 | 3.19 | 3.38 | 2.10 (11-OAc, s, 3H) |
| 174 | H | COCH$_3$ | CH$_2$C≡CH | Br | −14.6° | 1.60 | 3.27 | 3.39 | 2.11 (11-OAc, s, 3H) |
| 175 | H | COCH$_3$ | CH$_2$CH=CH$_2$ | Br | −12.4° | 1.60 | 3.14 | 3.37 | 2.10 (11-OAc, s, 3H) |
| 176 | CHO | SO$_2$CH$_3$ | CH$_2$C≡CH | Br | −28.8° | 1.61 | 3.25 | 3.41 | 3.30 (10-OMs, s, 3H) 8.30 (4''-OCHO, s, 1H) |
| 177 | H | SO$_2$CH$_3$ | C$_2$H$_5$ | I | −26.4° | 1.60 | 3.17 | 3.37 | 3.24 (11-OMs, s, 3H) |
| 178 | H | SO$_2$CH$_3$ | C$_3$H$_7$ | I | −27.8° | 1.60 | 3.18 | 3.37 | 3.24 (11-OMs, s, 3H) |

EXAMPLE 1

A capsule preparation is formed by sufficiently mixing the following components of the following amounts and filling the same in a No. 3 capsule:

| | |
|---|---|
| 11,12-di-O-acetyl-8,9-anhydroerythromycin A-6,9-hemiketal [Compound (32)] | 1.5 mg |
| Lactobionic acid | 0.75 mg |
| Lactose | 96.25 mg |
| Magnesium stearate | 1 mg |
| per capsule | 99.5 mg |

For an adult, 1 to 2 capsules are given three times a day before each meal.

EXAMPLE 2

The following components of the following amounts are formed as a flat tablet, with slanted edges, of a diameter of 6.5 mm, according to the Japanese Pharmacopoeia, General Rule 14, Tablet Preparation:

| | |
|---|---|
| 11,12-di-O-acetyl-8,9-anhydroerythromycin A-6,9-hemiketal [Compound (32)] | 2.5 mg |
| Lactobionic acid | 1.25 mg |
| Lactose | 72.25 mg |
| Corn starch | 30 mg |
| Hydroxypropyl cellulose | 3 mg |
| Magnesium stearate | 0.5 mg |
| per tablet | 109.5 mg |

For an adult, a tablet is given three times a day before each meal.

EXAMPLE 3

The following components of the following amounts are dissolved in distilled water for injection, then filtered by a Millipore filter, and lyophilized. An intravenous injection preparation is prepared, at use, by dissolving thus lyophilized product in distilled water for injection to a total volume of 5 ml:

| | |
|---|---|
| 11,12-di-O-acetyl-8,9-anhydroerythromycin A-6,9-hemiketal [Compound (32)] | 2 mg |
| Lactobionic acid | 1 mg |
| Mannitol | 150 mg |
| | 153 mg |

For an adult, this preparation is divided into 10 portions, and three administrations are given a day, one portion each time.

EXAMPLE 4

A capsule preparation is formed by sufficiently mixing the following components of the following amounts and filling the same in a No. 3 capsule:

| | |
|---|---|
| 11-O-methanesulfonyl-8,9-anhydroerythromycin A-6,9-hemiketal [Compound (57)] | 1.5 mg |
| Lactobionic acid | 0.75 mg |
| Lactose | 96.25 mg |
| Magnesium stearate | 1 mg |
| per capsule | 99.5 mg |

For an adult, 1 to 2 capsules are given three times a day before each meal.

EXAMPLE 5

The following components of the following amounts are formed as a flat tablet, with slanted edges, of a diameter of 6.5 mm, according to the Japanese Pharmacopoeia, General Rule 14, Tablet Preparation:

| | |
|---|---|
| 11-O-methanesulfonyl-8,9-anhydroerythromycin A-6,9-hemiketal [Compound (57)] | 2.5 mg |
| Lactobionic acid | 1.25 mg |
| Lactose | 72.25 mg |
| Corn starch | 30 mg |
| Hydroxypropyl cellulose | 3 mg |
| Magnesium stearate | 0.5 mg |
| per tablet | 109.5 mg |

For an adult, a tablet is given three times a day before each meal.

EXAMPLE 6

The following components of the following amounts are dissolved in distilled water for injection, then filtered by a Millipore filter, and lyophilized. An intravenous injection preparation is prepared, at use, by dissolving thus lyophilized product in distilled water for injection to a total volume of 5 ml.:

| | |
|---|---|
| 11-O-methanesulfonyl-8,9-anhydroerythromycin A-6,9-hemiketal [Compound (57)] | 2 mg |
| Lactobionic acid | 1 mg |
| Mannitol | 150 mg |
| | 153 mg |

For an adult, this preparation is divided into 10 portions, and three administrations are given a day, one portion each time.

EXAMPLE 7

| | |
|---|---|
| 8,9-anhydroerythromycin A 6,9-hemiketal-methyliodid [Compound (55)] | 0.5 mg |
| Lactose | 96.25 mg |
| Magnesium stearate | 1 mg |
| per capsule | 96.75 mg |

A capsule preparation is formed by sufficiently mixing the above components of the above amounts and filling the same in a No. 3 capsule.

For an adult, 1 to 2 capsules are given three times a day before each meal.

EXAMPLE 8

| | |
|---|---|
| 8,9-anhydroerythromycin A-6,9-hemiketal-ethyliodid [Compound (60)] | 0.2 mg |
| Lactose | 72.25 mg |
| Corn starch | 30 mg |
| lHydroxypropyl cellulose | 3 mg |
| Magnesium stearate | 0.5 mg |
| per capsule | 105.95 mg |

The above components of the above amounts are formed as a flat table, with slated edges, of a diameter of 6.5 mm, according to the Japanese Pharmacopoeia, General Rule 14, Tablet Preparation.

For an adult, a tablet is given three times a day before each meal.

EXAMPLE 9

| | |
|---|---|
| 11-O-methanesulfonyl-4''-O-formyl 8,9-anhydroerythromycin A-6,9-hemiketal [Compound (25)] | 2.5 mg |
| Lactobionic acid | 1.25 mg |
| Lactose | 72.25 mg |
| Corn starch | 30 mg |
| Hydroxypropyl cellulose | 3 mg |
| Magnesium stearate | 0.5 mg |
| per capsule | 109.5 mg |

The above components of the above amounts are formed as a flat table, with slanted edges, of a diameter of 6.5 mm, according to the Japanese Pharmacopoeia, General Rule 14, Tablet Preparation.

For an adult, a tablet is given three times a day before each meal.

As described hereinbefore, the compound [1] has an excellent effect of stimulating the gastrointenstinal contractive motion, and the preparation of the present invention containing this compound can be advantageously used as a digestive tract contractile motion stimulant.

What is claimed is:

1. A therapeutic method of stimulating digestive tract contractile motion in mammals which comprises administering orally or non-orally to mammals in need of such treatment an effective amount of a digestive tract contractile motion stimulant composition comprising a pharmaceutically acceptable carrier and an effective digestive contractile motion stimulating amount of a compound having the formula:

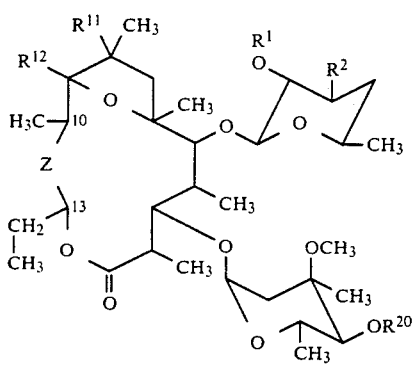

wherein $R^1$ is selected from the group consisting of:
a hydrogen atom,
an acyl radical of $C_{1-5}$ aliphatic carboxylic acid,
a $C_{6-12}$ aroyl radical,
a $C_{1-6}$ alkylsulfonyl radical,
a $C_{2-12}$ dialkyloxyphosphoryl radical, and
a $C_{12-24}$ diaryloxyphosphoryl radical;

$R^2$ is selected from the group consisting of:
a hydrogen atom,
a $C_{1-6}$ alkanoyl radical which may be substituted by $C_{1-3}$ alkoxycarbonyl radical,
a $C_{6-12}$ aroyl radical,
a $C_{1-6}$ alkylsulfonyl radical,
a $C_{6-12}$ arylsulfonyl radical,
a $C_{7-20}$ aralkylsulfonyl radical, and
a $C_{1-3}$ alkyl radical which may be substituted by $C_{2-6}$ alkoxy radical;

wherein Z stands for the formula:

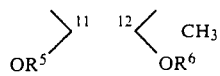

where in $R^5$ is selected from the group consisting of:
a hydrogen atom,
a $C_{1-6}$ alkanoyl radical,
a $C_{6-12}$ aroyl radical,
a $C_{1-6}$ alkylsulfonyl radical,
a $C_{6-12}$ arylsulfonyl radical,
a $C_{7-20}$ aralkylsulfonyl radical, and
a $C_{1-3}$ alkyl radical which may be substituted by $C_{1-4}$ alkylthio radical, and $R^6$ is selected from the group consisting of:
a hydrogen atom,
a $C_{1-6}$ alkanoyl radical; and
a $C_{1-3}$ alkyl radical which may be unsubstituted by $C_{1-4}$ alkylthio radical, or wherein Z stands for the formula:

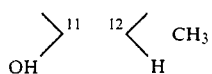

or Z stands for the formula:

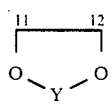

wherein Y stands for the formula B-$R^8$ (wherein $R^8$ stands for $C_{6-12}$ aryl radical)

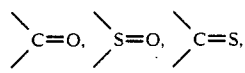

or the formula:

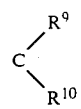

wherein each of $R^9$ and $R^{10}$, which may be the same or different, stands for a hydrogen atom or a $C_{1-6}$ alkyl radical;

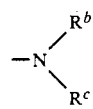

wherein $R^b$ is selected from the group consisting of:
a hydrogen atom and
a $C_{1-6}$ alkyl radical;
and wherein $R^c$ is selected from the group consisting of:
a hydrogen atom,
a $C_{2-6}$ alkyl radical which may be substituted with one or more hydroxyl radicals,
a $C_{2-6}$ alkenyl radical, and a $C_{2-6}$ alkynyl radical;
or together $R^b$ and $R^c$ from a $C_{3-6}$ cyclic alkylamino radical together with the adjacent nitrogen atom;
or
$R^a$ stands for the formula

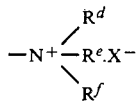

wherein $R^d$ is $C_{1-6}$ alkyl radical, and $R^e$ and $R^f$, which may be the same or different are selected from the group consisting of:
a hydrogen atom,
a $C_{1-6}$ alkyl radical which may be substituted by hydroxyl radical, carboxy radical, cyano radical, or halogen, a $C_{3-5}$ cycloalkyl radical, or a $C_{1-3}$ alkoxycarbonyl radical;
a $C_{7-20}$ aralkyl radical;
a $C_{2-6}$ alkenyl radical; and
a $C_{2-6}$ alkynyl radical; or
together $R^e$ and $R^f$ form a $C_{5-7}$ cyclic alkylamino radical with the adjacent nitrogen atom;
X stands for an anion; and
$R^{11}$ and $R^{12}$ each represent a hydrogen atom or both taken together to form a chemcial bond.

2. The method of claim 1, wherein the digestive tract contractile motion stimulant compound is selected from the group consisting of: 8,9-anhydroerythromycin A 6,9-hemiketal methyl iodide, 8,9-anhydroerythromycin A 6,9-hemiketal 2-hydroxyethyl bromide, 8,9-anhydfroerythromycin A 6,9-hemiketal allyl bromide, 8,9-anhydroerythromycin A 6,9-hemiketal benzyl chloride, 8,9-anhydroerythromycin A 6,9-hemiketal ethyl bromide, diethyl-dinor-anhydroerythromycin A 6,9-hemiketal, 8,9-anhydroerythromycin A propargyl bromide, allyl-nor-8,9-anhydroerythromycin A 6,9-hemiketal and 8,9-anhydroerythromycin A 6,9-hemiketal propargyl chloride.

3. The method of claim 1, wherein $R^1$ in the digestive tract contractile motion stimulant compound is a hydrogen atom or an acyl radical of $C_{1-5}$ aliphatic carboxylic acid.

4. The method of claim 1, wherein $R^2$ in the digestive tract contractile motion stimulant compound is a hydrogen atom, a $C_{1-5}$ alkanoyl radical or $C_{1-5}$ alkylsulfonyl radical.

5. The method of claim 1, wherein Z in the digestive tract contractile motion stimulant compound has the formula:

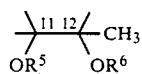

wherein each of $R_5$ and $R_6$ are independently selected from the group consisting of hydrogen atom, and a $C_{1-5}$ alkanoyl radical.

6. The method of claim 1, wherein Y in the digestive tract contractile motion stimulant compound is selected from the group consisting of:

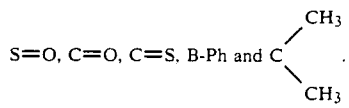

7. The method of claim 1, wherein $R^a$ in the digestive tract contractile motion stimulant compound has the formula:

wherein $R^b$ is a $C_1$ to $C_6$ radical and $R^c$ is a $C_2$ to $C_6$ alkyl radical which may be substituted with one or more hydroxyl radicals.

8. The method of claim 1, wherein $R^a$ in the digestive tract contractile motion stimulant compound is N-methyl-N-ethylamino radical.

9. The method of claim 1, wherein $R^a$ in the digestive tract contractile motion stimulant compound has the formula:

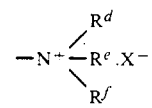

wherein $R^d$ is a $C_{1-6}$ alkyl radical, and $R^e$ and $R^f$, which may be the same or different are selected from the group consisting of:
a hydrogen atom,
a $C_{1-6}$ alkyl radical which may be substituted by hydroxyl radical, carboxy radical, cyano radical, halogen, $C_{3-5}$ cycloalkyl radical, or $C_{1-3}$ alkoxycarbonyl radical;
a $C_{7-20}$ aralkyl radical;
a $C_{2-6}$ alkenyl radical; and
a $C_{2-6}$ alkynyl radical; or
together $R^e$ and $R^f$ form a $C_{5-7}$ cyclic alkylamino radical with the adjacent nitrogen atom;
and X stands for an anion.

10. THe method of claim 1, wherein $R^f$ in the digestive tract contractile motion stimulant compound is $C_{2-6}$ alkenyl or $C_{2-6}$ alkynyl radical.

11. The method of claim 1, wherein $R^e$ and $R^f$ form a $C_{5-7}$ cyclic alkylamino radical with the adjacent nitrogen atom.

12. The method of claim 1, wherein a digestive tract contractile motion stimulant composition additionally comprises one or more of the pharmaceutically acceptable additional components selected from the group consisting of vehicle, disintegrator, lubricant, binder, dispersant and plasticizer.

13. The method of claim 1, wherein the effective amount of the digestive contractile motion stimulating compound of formula (1) for oral administration to a mammal in need of such treatment is in the range of from about 0.0001 to 100 mg/kg in a form diluted or compounded with pharmaceutically acceptable carries or diluents.

14. The method of claim 1, wherein the effective amount of the digestive contractile motion stimulating compound for oral administration to a mammal in need of such treatment is in the range of from about 0.00001 to 10 mg/kg in a form diluted or compounded with pharmaceutically acceptable carriers or diluents.

* * * * *

UNITED STATES PATENT AND TRADEMARK OFFICE
CERTIFICATE OF CORRECTION

PATENT NO. : 5,008,249                          Page 1 of 3
DATED     : April 16, 1991
INVENTOR(S) : Satoshi Omura and Zen Itoh It is certified that error appears in the above-identified patent and that said Letters Patent is hereby corrected as shown below:

Col. 2, L. 13, change "OR"" to --$OR^2$--.

Col. 2, L. 53, change "$R_c$" to --$R^c$--.

Col. 14, L. 27, change "$R^a$" to --$R^g$--.

Col. 16, L. 58, insert break line in structure as follows:

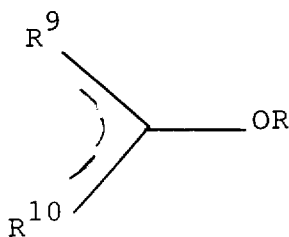

Col. 97, L. 37, change "$R^2$" to --$R^a$--.

Col. 97, L. 48, change "$OR^{20}$" to --$R^2$--.

Col. 98, L. 1-5, change structure as follows:

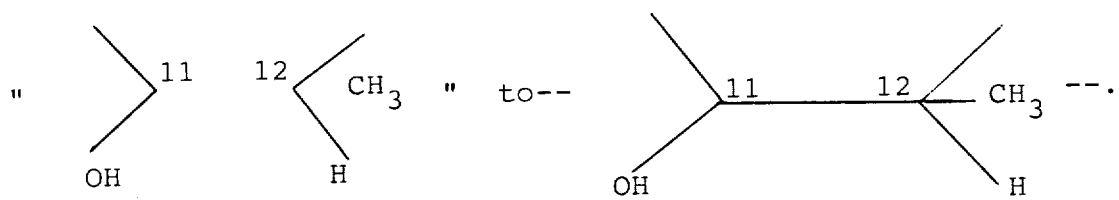

UNITED STATES PATENT AND TRADEMARK OFFICE
CERTIFICATE OF CORRECTION

PATENT NO. : 5,008,249  Page 2 of 3
DATED : April 16, 1991
INVENTOR(S) : Satoshi Omura and Zen Itoh It is certified that error appears in the above-identified patent and that said Letters Patent is hereby corrected as shown below:

Col. 98, L. 24, change structure as follows:

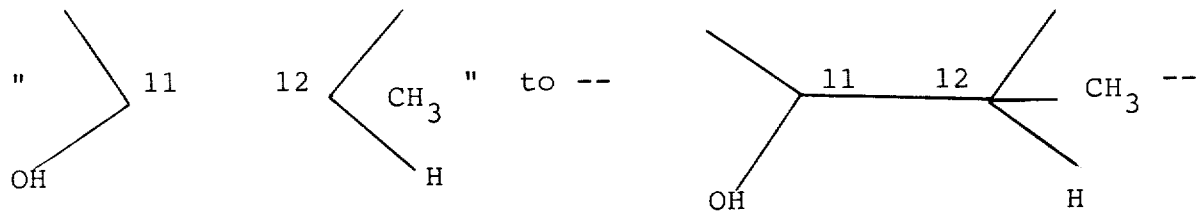

Col. 98, L. 54, insert --$R^a$ stands for the formula-- before "structure".

Col. 99, L. 58, change structure as follows:

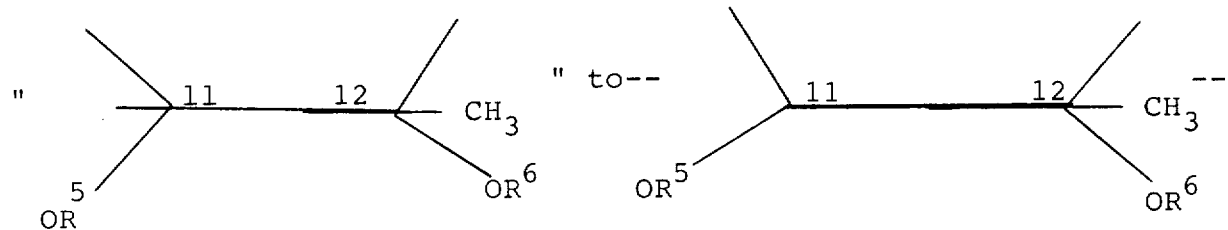

UNITED STATES PATENT AND TRADEMARK OFFICE
CERTIFICATE OF CORRECTION

PATENT NO. : 5,008,249

DATED : April 16, 1991

INVENTOR(S) : Satoshi Omura and Zen Itoh

It is certified that error appears in the above-identified patent and that said Letters Patent is hereby corrected as shown below:

Col. 100, L. 16, insert --alkyl-- before "radical".

Col. 100, L. 44, change "THe" to --The--.

In the Abstract [57], L. 5, change "$R^2O$" to --$R^1O$--.

In the Abstract [57], L. 6, change "$R^4$" to --$R^a$--.

Signed and Sealed this

Thirteenth Day of October, 1992

Attest:

DOUGLAS B. COMER

Attesting Officer

Acting Commissioner of Patents and Trademarks

UNITED STATES PATENT AND TRADEMARK OFFICE
CERTIFICATE OF CORRECTION

PATENT NO. : 5,008,249
DATED : April 16, 1991
INVENTOR(S) : Satoshi Omura and Zen Itoh It is certified that error appears in the above-identified patent and that said Letters Patent is hereby corrected as shown below:

Col. 97, line 48, change "$OR^{20}$" to --$OR^2$--

Col. 98, lines 1-5, change structure to read as follows;

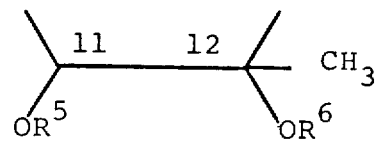

Signed and Sealed this

Eighth Day of February, 1994

Attest:

BRUCE LEHMAN

Attesting Officer    Commissioner of Patents and Trademarks